US012807575B2

(12) United States Patent
Cleary et al.

(10) Patent No.: US 12,807,575 B2
(45) Date of Patent: Nov. 24, 2026

(54) QUINOLINONE DERIVATIVES AS METHIONINE ADENOSYLTRANSFERASE 2A INHIBITORS

(71) Applicant: IDEAYA BIOSCIENCES, INC., South San Francisco, CA (US)

(72) Inventors: Leah Cleary, South San Francisco, CA (US); Melissa Fleury, South San Francisco, CA (US); Zhonghua Pei, South San Francisco, CA (US)

(73) Assignee: IDEAYA BIOSCIENCES, INC., South San Francisco, CA (US)

( * ) Notice: Subject to any disclaimer, the term of this patent is extended or adjusted under 35 U.S.C. 154(b) by 737 days.

(21) Appl. No.: 18/009,206

(22) PCT Filed: Jun. 9, 2021

(86) PCT No.: PCT/US2021/036681

§ 371 (c)(1),
(2) Date: Dec. 8, 2022

(87) PCT Pub. No.: WO2021/252681

PCT Pub. Date: Dec. 16, 2021

(65) Prior Publication Data

US 2023/0227409 A1 Jul. 20, 2023

Related U.S. Application Data

(60) Provisional application No. 63/037,083, filed on Jun. 10, 2020.

(51) Int. Cl.

*C07D 215/22* (2006.01)
*C07D 215/227* (2006.01)
*C07D 215/36* (2006.01)
*C07D 215/38* (2006.01)
*C07D 401/04* (2006.01)
*C07D 417/12* (2006.01)
*C07D 495/04* (2006.01)

(52) U.S. Cl.

CPC ....... *C07D 215/22* (2013.01); *C07D 215/227* (2013.01); *C07D 215/36* (2013.01); *C07D 215/38* (2013.01); *C07D 401/04* (2013.01); *C07D 417/12* (2013.01); *C07D 495/04* (2013.01)

(58) Field of Classification Search

CPC C07D 215/22; C07D 215/227; C07D 215/36; C07D 215/38; C07D 401/04; C07D 417/12; C07D 495/04

USPC ....................................................... 514/260.1

See application file for complete search history.

(56) References Cited

U.S. PATENT DOCUMENTS

| | | | |
|---|---|---|---|
| 3,202,661 A | 8/1965 | Brust et al. | |
| 4,096,144 A | 6/1978 | Yamamoto et al. | |
| 5,892,045 A | 4/1999 | Sit et al. | |
| 5,972,961 A | 10/1999 | Hewawasam et al. | |
| 7,098,332 B2 | 8/2006 | Liu et al. | |
| 7,880,000 B2 | 2/2011 | Geuns-Meyer et al. | |
| 8,338,435 B2 | 12/2012 | Herdewijn et al. | |
| 8,722,580 B2 | 5/2014 | Nagasawa et al. | |
| 10,329,298 B2 | 6/2019 | Konteatis et al. | |
| 10,519,146 B2 | 12/2019 | Lanman et al. | |
| 10,532,042 B2 | 1/2020 | Lanman et al. | |
| 10,800,782 B2 | 10/2020 | Konteatis et al. | |
| 11,046,691 B1 | 6/2021 | Alam et al. | |
| 11,084,798 B1 | 8/2021 | Alam et al. | |
| 11,130,759 B1 | 9/2021 | Alam et al. | |
| 2002/0193377 A1 | 12/2002 | Andrianjara et al. | |
| 2004/0067968 A1* | 4/2004 | Angibaud | A61P 33/06 544/286 |

(Continued)

FOREIGN PATENT DOCUMENTS

| | | |
|---|---|---|
| CA | 3075046 A1 | 3/2019 |
| CA | 3098574 A1 | 11/2019 |

(Continued)

OTHER PUBLICATIONS

R. D. Larsen, Product class 4: quinolinones and related systems, 2005, Science of Synthesis, 15, 551-660 (Year: 2005).*

(Continued)

*Primary Examiner* — Kristin A Vajda
(74) *Attorney, Agent, or Firm* — Mintz Levin Cohn Ferris Glovsky and Popeo, P.C.

(57) ABSTRACT

Disclosed herein are certain quinolinone derivatives of Formula (A) that are methionine adenosyltransferase 2A (MAT2A) inhibitors. Also disclosed are pharmaceutical compositions comprising such compounds and methods of treating diseases treatable by inhibition of MAT2A such as cancer, including cancers characterized by reduced or absence of methylthioadenosine phosphorylase (MTAP) activity.

(A)

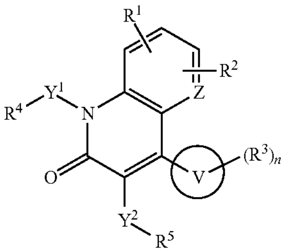

10 Claims, No Drawings

(56) References Cited

U.S. PATENT DOCUMENTS

| | | | |
|---|---|---|---|
| 2005/0176763 | A1 | 8/2005 | Boy et al. |
| 2009/0253696 | A1 | 10/2009 | Herdewijn et al. |
| 2011/0166135 | A1 | 7/2011 | Morimoto et al. |
| 2012/0178915 | A1 | 7/2012 | Xu |
| 2014/0220580 | A1 | 8/2014 | Brown et al. |
| 2018/0079753 | A1 | 3/2018 | Konteatis et al. |
| 2018/0177767 | A1 | 6/2018 | Lanman et al. |
| 2018/0334454 | A1 | 11/2018 | Lanman et al. |
| 2018/0371551 | A1 | 12/2018 | Marjon et al. |
| 2019/0077801 | A1 | 3/2019 | Lanman et al. |
| 2019/0343838 | A1 | 11/2019 | Allen et al. |
| 2019/0374542 | A1 | 12/2019 | Allen et al. |
| 2020/0000821 | A1 | 1/2020 | Basford et al. |
| 2020/0022984 | A1 | 1/2020 | Wang et al. |
| 2022/0106276 | A1 | 4/2022 | Alam et al. |

FOREIGN PATENT DOCUMENTS

| | | | | |
|---|---|---|---|---|
| CN | 102816197 | A | 12/2012 | |
| EP | 0664128 | A1 | 7/1995 | |
| EP | 0885894 | A1 | 12/1998 | |
| EP | 2100507 | A1 | 9/2009 | |
| EP | 2266984 | A1 | 12/2010 | |
| JP | S50105694 | A | 8/1975 | |
| RU | 2345077 | C2 | 1/2009 | |
| WO | WO-1995031469 | A1 | 11/1995 | |
| WO | WO-1995031495 | A1 | 11/1995 | |
| WO | WO-2002012782 | A2 | 12/2002 | |
| WO | 2004065542 | A2 | 8/2004 | |
| WO | 2005020885 | A2 | 3/2005 | |
| WO | WO-2006032470 | A1 * | 3/2006 | ................ A61P 3/06 |
| WO | WO-2008154221 | A2 | 12/2008 | |
| WO | WO-2010149786 | A1 | 12/2010 | |
| WO | 2012103457 | A2 | 8/2012 | |
| WO | WO-2013049352 | A2 | 4/2013 | |
| WO | WO-2014159837 | A1 | 10/2014 | |
| WO | WO-2017096165 | A1 | 6/2017 | |
| WO | WO-2018014802 | A1 | 1/2018 | |
| WO | WO-2018039972 | A1 | 3/2018 | |
| WO | WO-2018045071 | A1 | 3/2018 | |
| WO | WO-2018119183 | A2 | 6/2018 | |
| WO | WO-2018177297 | A1 | 10/2018 | |
| WO | 2018215798 | A1 | 11/2018 | |
| WO | WO-2018221433 | A1 | 12/2018 | |
| WO | WO-2019191470 | A1 | 10/2019 | |
| WO | WO-2019213516 | A1 | 11/2019 | |
| WO | 2020011921 | A1 | 1/2020 | |
| WO | 2020050890 | A2 | 3/2020 | |
| WO | WO-2020113071 | A1 | 6/2020 | |
| WO | WO-2020123395 | A1 | 6/2020 | |
| WO | WO-2020139991 | A1 | 7/2020 | |
| WO | WO-2020139992 | A1 | 7/2020 | |
| WO | WO-2021252678 | A1 | 12/2021 | |
| WO | WO-2021252679 | A1 | 12/2021 | |
| WO | WO-2021252680 | A1 | 12/2021 | |
| WO | WO-2021252681 | A1 | 12/2021 | |
| WO | 2022/036067 | A1 | 2/2022 | |
| WO | 2022/036067 | A4 | 2/2022 | |
| WO | 2022/256806 | A1 | 12/2022 | |
| WO | 2023/086934 | A1 | 5/2023 | |
| WO | 2023/196985 | A1 | 10/2023 | |
| WO | 2023/201338 | A1 | 10/2023 | |
| WO | 2024/118830 | A1 | 6/2024 | |
| WO | 2025/059579 | A1 | 3/2025 | |

OTHER PUBLICATIONS

Angibaud et al., Impact on farnesyltransferase inhibition of 4-chlorophenyl moiety replacement in the Zarnestra® series, European Journal of Medicinal Chemistry, May 1, 2007, vol. 42, No. 5, pp. 702-714.

Barile et al., Supporting information Synthesis and SAR studies of dual AKT/NF-kappaB inhibitors against melanoma, Chemical Biology & Drug Design 2013, Jun. 21, 2013, vol. 82, No. 5, pp. 520-533.

Bhat et al., An Efficient Three-component, One-pot Synthesis of Quinazolines under Solvent-free and Catalyst-free Condition, Journal of Heterocyclic Chemistry, Jul. 1, 2015, vol. 52, No. 4, pp. 1253-1259.

Botros et al., Synthesis of Pyrido [2,3-d] Pyrimidines from 2-Amino-3-Cyanopyridines, Egypt J. Chem, 1986, vol. 29, No. 3, pp. 275-281.

Castellano et al., Synthesis and Biological Evlauation of 4-Phenylquinazoline-2- carboxamides Designed as a Novel Class of Potent Ligands of the Translocator Protein, Journal of Medicinal Chemistry, May 10, 2012, vol. 55, No. 9, pp. 4506-4510.

Castellano et al., Structure-Activity Relationship Refinement and Further Assessment of 4-Phenylquinazoline-2-carboxamide Translocator Protein Ligand as Antiprofiferative Agents in Human Glioblastoma Tumors, Journal of Medical Chemistry, Mar. 27, 2014, vol. 57, No. 6, pp. 2413-2418.

Database Reaxys, Database accession No. JP2086665, abstract, 1963.

Database CAPLUS Chemical Abstracts Service, Teixeira et al., Microwave Assisted Synthesis of 4-Phenylquinazolin-2(1H)-one Derivatives that Inhibit Vasopressor Tonus in Rat Thoracic Aorta, , Database Accession No. 2020:950425, Mar. 24, 2020, abstract.

Database CAPLUS Chemical Abstracts Service, Pham et al., Novel 1,2- dihydroquinazolin-2-ones: Design, synthesis, and biological evaluation against Trypanosoma brucei, Database accession No. 2017:1197666, Aug. 1, 2017, abstract.

Database CAPLUS Chemical Abstracts Serivce, Yong-Goo et al., A facile syntheses of N-arylcyanoformamidoximes, 4-aryl-3-cyano-1,2,4-oxidiazin-5(6H)-ones, 2-cyanoquinazoline-3-oxides, and 2-cyanoquinazolines via 5-arylimino-4-chloro-5H-1,2,3-dithiazoles, Database accession No. 1999:710017, Jan. 1, 1999, abstract.

Database CAPLUS Chemical Abstracts Service, Felix et al., Quinazolines and 1,4-benzodiazepines. XLIII. Oxidations with ruthenium tetroxide, Database accession No. 1969:4080, Oct. 1, 1968.

Database CAPLUS Chemical Abstracts Service, Fryer et al., Quinazolines and 1,4-benzodiazepines. XXXVII. Synthesis and rearrangements of substituted 5-pjhenyl-1H-1,4-benzodiazepine, Database accession No. 1968:21907, Dec. 1, 1967, Abstract.

De Fusco et al., Fragment-Based Design of a Potent MAT2a Inhibitor and in Vivo Evaluation in an MTAP Null Xenograft Model, Journal of Medicinal Chemistry, Apr. 26, 2021, vol. 64, No. 10, pp. 6814-6826.

International Search Report for International Application No. PCT/US2019/065260, mailed Apr. 8, 2020, 6 pages.

International Search Report for International Application No. PCT/US2021/036678, mailed Aug. 18, 2021, 4 pages.

International Search Report for International Application No. PCT/US2021/036679, mailed Aug. 20, 2021, 3 pages.

International Search Report for International Application No. PCT/US2021/036680, mailed Aug. 18, 2021, 11 pages.

International Search Report for International Application No. PCT/US2021/036681, mailed Aug. 27, 2021, 10 pages.

Fryer et al., 590. Synthetical Methods for the Preparation of 3-Amino-2(1H)-quinolones, J. Chem. Soc., 1964, pp. 3097-3101.

Jatangi et al., 12-Catalyzed oxidative synthesis of N,4-disubstituted quinazolines and quinazoline oxides, Organic and Biomolecular Chemistry, Apr. 10, 2019, vol. 17, No. 15, pp. 3714-3717.

Kamal et al., Efficient Enzymatic Cyclization of 2-(Carbmoyloxy)-AND 2-(Sulfamoyloxy)-Benzonitriles by Ultrasonically Stimulated Baker's Yeast, Heterocycles, 1990, vol. 31, No. 4, pp. 577-579.

Kobayashi, A Concise and Versatile Synthesis of Viridicatin Alkaloids from Cyanoacetanilides, Organic Letters, 2009, vol. 11, No. 7, pp. 1603-1606.

Moghadam et al., 2,4-Disubstituted Quinazolin Derivatives Act as Inducers of Tubulin Polymerization: Synthesis and Cytotoxicity, Anti-Cancer Agents in Medicinal Chemistry, Aug. 21, 2019, vo. 19, No. 8, pp. 1048-1057.

Noda et al., Chemical Abstract, vol. 84, No. 59544 (Abstract for JP-50105694, Aug. 20, 1975. (year: 1976).

(56) References Cited

OTHER PUBLICATIONS

Prezent, Camps reaction for the systhesis of 3-RS-4-arylquinolin-2-ones, Russian Chemical Bulletin International Edition, Nov. 2003, vol. 52, pp. 2454-2456.
Rehwald et al., 3-Amino-2(1H)-quinolones by Cyclizaion of N-Acylated Anthranilic Acid Derivatives, Heterocycles, Jan. 1, 1997, vol. 45, Jan. 1, 1997, vol. 45, No. 3, pp. 483-492.
Shaik et al., Evaluation of Anticancer and Anti-Mitotic Properties of Quinazoline and Quinazolino-Benzothiadiazine Derivatives, Anti-Cancer Agents in Medicinal Chemistry, May 28, 2020, vol. 20, No. 5, pp. 599-611.
Tangella et al., Regioselective Ring Expansion of Isatins with In Situ Generated alpha-Aryldiazomethanes: Direct Access to Viridicatin Alkaloids, Organic Letters, 2018, vol. 20, pp. 3639-3642.
Walker et al., Novel synthesis of 1,4-benzodiazepines, isoindolo[2,1-d] [1,4]benzodiazepines, isoindolo[1,2-a] [2] benzazepines, and indolo[2,3-d] [2]benzazepines, Based on Use of the Strecker Reaction, The Journal of Organic Chemistry, Dec. 1, 1972, vol. 37, No. 24, pp. 3755-3770.
Zhao et al., Synthesis of a Complete Janus-type Guanosine-Cystosine Base and Its 2-Deoxyribonucleoside, Chem Lett., 2011, vol. 40, pp. 684-686.
Written Opinion for International Application No. PCT/US2019/065260, mailed Apr. 8, 2020, 7 pages.
Written Opinion for International Application No. PCT/US2021/036678, mailed Aug. 18, 2021, 6 pages.
Written Opinion for International Application No. PCT/US2021/036679, mailed Aug. 20, 2021, 6 pages.
Written Opinion for International Application No. PCT/US2021/036680, mailed Aug. 18, 2021, 10 pages.
Written Opinion for International Application No. PCT/US2021/036681, mailed Aug. 27, 2021, 8 pages.
International Search Report for International Application No. PCT/US2022/051396, mailed Aug. 27, 2021, 12 pages.
International Search Report for International Application No. PCT/US/2023/065780, mailed May 12, 2023, 11 pages.
International Search Report for International Application No. PCT/US/2023/065540, mailed Jul. 21, 2023, 12 pages.
International Search Report for International Application No. PCT/US2023/081672, mailed Apr. 8, 2024, 11 pages.
International Search Report for International Application No. PCT/US2024/046774, mailed Nov. 28, 2024, 15 pages.
CAS Registry No. 119976-96-4; STN Entry Date Apr. 7, 1989; 7-Chloro-1-[3-(trifluoromethyl)phenyl]-2,4(1H,3H)-quinazolinedione; 6 pages.
Database: National Center for Biotechnology Information, Pubchem CID 153608878, Pubchem entry (online), pp. 1-11, Create date Aug. 13, 2020; Retrieved on Feb. 9, 2024 from the Internet: [URL: https://pubchem.ncbi.nim.nih.gov/compound_153608878]; p. 2, see 2D structure.
Dunkel, M. et al. "Nucleosides, XLVIII. Syntheses and Properties of Quinazoline N-1-Ribofuranosides," *Nucleosides and Nucleotides* (1991; Rec'd Aug. 10, 1990, published online Oct. 4, 2006) 10(4):799-817.
Guo, Jiamin et al., "Targeting the Methionine-MAT2A-SAM Axis for Cancer Therapy," *Curr Opin Oncol*. (published in final edited form Sep. 1, 2022) 34(5):546-551.
Ideaya Biosciences: "NCT04794699—Study of IDE397 in Participants with Solid Tumors Harboring MTAP Deletion," ClinicalTrials.gov (Dec. 1, 2022), XP093219291, Retrieved from the Internet: URL:https://clinicaltrials.gov./study/NCT04 794699?tab=history&a=13#versioncontent-panel [retrieved on Oct. 29, 2024]; 18 pages.
Ideaya Biosciences: "IDE397 (MAT2A inhibitor)," *Molecular Sherlock* (May 3, 2023), XP093219523, retrieved from the Internet: URL:https://victoriacyanide.substack.com/p/ide397-mat2a-inhibitor [retrived on Oct. 29, 2024]; 1 page.
Lanman, Brian A. et al., "Addressing Atropisomerism in the Development of Sotorasib, a Covalent Inhibitor of KRAS G12C: Structural, Analytical, and Synthetic Considerations," *Acc. Chem. Res.* (Sep. 30, 2022) 55:2892-2903.
Lima, Lidia Moreira et al., "Bioisosterism: A Useful Strategy for Molecular Modification and Drug Design," *Current Medicinal Chemistry* (Jan. 1, 2005) 12(1):23-49(27).
Marjon, Katya et al., "MTAP Deletions in Cancer Create Vulnerability to Targeting of the MAT2A/PRMT5/RIOKI Axis," *Cell Reports* (Apr. 1, 2016) 15(3):574-587.
Naik, B. et al., "Synthesis of 1-(2-methyl-4-quinolinyl)-2(1H)-quinazolinones as antibacterial agents," *Journal of the Institute of Chemists* (Jan. 1, 1998) 79(3):106-107.
Yang, Hao-Zhe et al., "Synthesis of Janus type nucleoside analogues and their preliminary bioactivity," Org. Biomol. Chem., (2011; accepted Nov. 11, 2010) 9:1516-1522.
Yang, Li-Jun et al., "Bisphosphine-Triggered One-Pot Sequential [3 + 2]/[3 + 2] Annulation of Allenoates with Cyclic Ketimines," Organic Letters (Oct. 18, 2013) 15(20):5214-5217.
Lafferty et al., The preparation and properties of certain pyridylpyrimidines and bidiazines as potential chelating agents for iron (II), J. Org. Chem., 32, pp. 1591-1596 (year: 1967).

* cited by examiner

QUINOLINONE DERIVATIVES AS METHIONINE ADENOSYLTRANSFERASE 2A INHIBITORS

CROSS-REFERENCES TO RELATED APPLICATIONS

This application claims the benefit under 35 U.S.C. 119(e) of U.S. Provisional Application No. 63/037,083, filed on Jun. 10, 2020, the contents of which is hereby incorporated by reference in its entirety for all purposes.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Cancer is a leading cause of death throughout the world. A limitation of prevailing therapeutic approaches, e.g. chemotherapy and immunotherapy is that their cytotoxic effects are not restricted to cancer cells and adverse side effects can occur within normal tissues. Consequently, novel strategies are needed to better target cancer cells.

Synthetic lethality arises when a combination of deficiencies in the expression of two or more genes leads to cell death, whereas a deficiency in only one of these genes does not. The concept of synthetic lethality originates from studies in *drosophila* model systems in which a combination of mutations in two or more separate genes leads to cell death (in contrast to viability, which occurs when only one of the genes is mutated or deleted). More recently, a multitude of studies have explored maladaptive genetic changes in cancer cells that render them vulnerable to synthetic-lethality approaches. These tumor-specific genetic defects lead to the use of targeted agents that induce the death of tumor cells while sparing normal cells.

Methionine adenosyltransferase 2A (MAT2A) is an enzyme that utilizes methionine (Met) and adenosine triphosphate (ATP) to generate s-adenosyl methionine (SAM). SAM is a primary methyl donor in cells used to methylate several substrates including DNA, RNA and proteins. One methylase that utilizes SAM as a methyl donor, is protein arginine N-methyltransferase 5 (PRMT5). While SAM is required for PRMT5 activity, PRMT5 iscompetitively inhibited by 5'methylthioadenosine (MTA). Since MTA is part of the methionine salvage pathway, cellular MTA levels stay low in a process initiated by methylthioadenosine phosphorylase (MTAP).

MTAP is in a locus on chromosome 9 that is often deleted in cells of patients with cancers from several tissues of origin including central nervous system, pancreas, esophageal, bladder and lung (cBioPortal database). Loss of MTAP results in the accumulation of MTA making MTAP-deleted cells more dependent on SAM production, and thus MAT2A activity, compared to cells that express MTAP. In an shRNA cell-line screen across approximately 400 cancer cell lines, MAT2A knockdown resulted in the loss of viability in a larger percentage of MTAP-deleted cells compare to MTAP WT cells (see McDonald et. al. 2017 *Cell* 170, 577-592). Furthermore, inducible knockdown of MAT2A protein decreased tumor growth in vivo (see Marjon et. al., 2016 *Cell Reports* 15(3), 574-587). These results indicate that MAT2A inhibitors may provide a novel therapy for cancer patients including those with MTAP-deleted tumors.

SUMMARY

Disclosed herein are certain quinolinone derivatives that are methionine adenosyltransferase 2A (MAT2A) inhibitors. Also disclosed are pharmaceutical compositions comprising such compounds and methods of treating diseases treatable by inhibition of MAT2A such as cancer, including cancers characterized by reduced or absence of methylthioadenosine phosphorylase (MTAP) activity.

In a first aspect, provided herein is a compound of Formula (A)

(A)

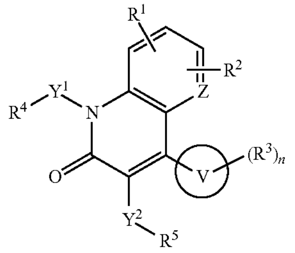

or a pharmaceutically acceptable salt thereof, wherein Z, $R^1$, $R^2$, $Y^1$, $R^4$, $Y^2$, $R^5$, $R^3$, n and ring V are as defined herein.

In a second aspect, provided is a compound of Formula (I):

(I)

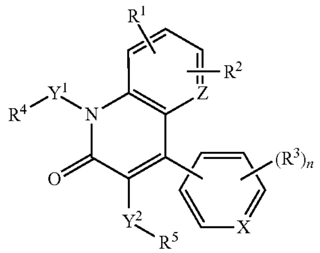

or a pharmaceutically acceptable salt thereof, wherein

Z is selected from the group consisting of CH and N;

$R^1$ and $R^2$ are each independently selected from the group consisting of H, $C_{1-6}$ alkyl, $C_{1-6}$ haloalkyl, $C_{1-6}$ alkoxy, cyano, halo and $C_{3-8}$ cycloalkyl, wherein the cycloalkyl group is substituted with from 0 to 2 groups independently selected from the group consisting of $C_{1-4}$ alkyl and halo;

X is CH, $CR^3$, or N;

each $R^3$ is independently selected from the group consisting of halo, $C_{1-4}$ alkyl, $C_{1-4}$ haloalkyl, —$OR^z$, and —$X^4$—$OR^z$, wherein each $R^z$ is selected from the group consisting of H, $C_{1-4}$ alkyl, and $C_{1-4}$ haloalkyl, and each $X^4$ is $C_{1-3}$ alkylene;

the subscript n is 0, 1 or 2;

$Y^1$ is selected from the group consisting of a bond and $C_{1-4}$ alkylene;

$R^4$ is selected from the group consisting of H, halo, $C_{1-6}$ alkyl, $C_{1-6}$ haloalkyl, $C_{6-10}$ aryl, —$NR^aR^b$, —$C(O)R^d$, —$C(O)OR^d$, —$C(O)NR^aR^b$, and a 6- to 10-membered heteroaryl ring having 1 to 3 heteroatom ring vertices independently selected from the group consisting of N, O, and S; wherein $R^a$ and $R^b$ are each independently selected from the group consisting of H, $C_{1-6}$ alkyl, $C_{1-6}$ haloalkyl, and phenyl; wherein the phenyl is substituted with 0 to 2 moieties independently selected from the group consisting of $C_{1-4}$ alkyl, —$OR^x$, and —$X^2$—$OR^x$, and wherein each $R^x$ is selected from the group consisting of H, $C_{1-4}$ alkyl, and $C_{1-4}$ haloalkyl, and each $X^2$ is $C_{1-3}$ alkylene;

$R^d$ is selected from the group consisting of H, $C_{1-6}$ alkyl, and $C_{1-6}$ haloalkyl;

$Y^2$ is selected from the group consisting of a bond and $C_{1-4}$ alkylene;

$R^5$ is selected from the group consisting of H, halo, cyano, $C_{1-6}$ alkyl; $C_{1-6}$ haloalkyl, —$OR^c$, —O—$X^1$—$R^c$, —$SR^c$, —S—$X^1$—$R^c$, —$NR^fR^g$, —$S(O)_2R^c$, —$S(O)_2$—$X^1$—$R^c$, —$S(O)_2$—$NR^h$—$R^c$, —$S(O)_2$—$NR^h$—$X^1$—$R^c$, —$NR^h$—$S(O)_2$—$R^c$, —$NR^h$—$S(O)_2$—$X^1$—$R^c$, and a 3- to 6-membered heterocycloalkyl having 1 to 3 heteroatom ring vertices independently selected from the group consisting of N, O, and S;

$X^1$ is selected from the group consisting of a bond and $C_{1-4}$ alkylene;

$R^c$ is selected from the group consisting of H, $C_{1-6}$ alkyl, $C_{1-6}$ haloalkyl, $C_{3-8}$ cycloalkyl, $C_{6-10}$ aryl, a 3- to 6-membered heterocycloalkyl having 1 to 3 heteroatom ring vertices independently selected from N, O, and S, and a 5- to 10-membered heteroaryl having 1 to 4 heteroatom ring vertices independently selected from the group consisting of N, O, and S, wherein the $C_{3-8}$ cycloalkyl, the $C_{6-10}$ aryl, the 3- to 6-membered heterocycloalkyl, and the 5- to 10-membered heteroaryl are substituted with 0 to 2 moieties independently selected from the group consisting of $C_{1-4}$ alkyl, —$OR^y$, —$X^3$—$OR^y$, —$C(O)R^y$, —$X^3$—$C(O)R^y$, —$C(O)OR^y$, and —$X^3$—$C(O)OR^y$, wherein each $R^y$ is selected from the group consisting of H, $C_{1-6}$ alkyl, and $C_{1-6}$ haloalkyl, and each $X^3$ is $C_{1-3}$ alkylene;

$R^f$ and $R^g$ are each independently selected from the group consisting of H, $C_{1-6}$ alkyl, $C_{1-6}$ haloalkyl, and phenyl; or $R^f$ and $R^g$ together with the nitrogen to which they are attached combine to form a 4- to 6-membered heterocycloalkyl ring comprising 0 to 2 additional heteroatoms independently selected from the group consisting of N, O, and S, wherein the phenyl and the 4- to 6-membered heterocycloalkyl are substituted with 0 to 2 moieties independently selected from the group consisting of $C_{1-4}$ alkyl, —$OR^x$, and —$X^2$—$OR^x$, wherein each $R^x$ is selected from the group consisting of H, $C_{1-4}$ alkyl, and $C_{1-4}$ haloalkyl, and each $X^2$ is $C_1$-3 alkylene;

$R^h$ is selected from the group consisting of H, $C_{1-6}$ alkyl, $C_{1-6}$ haloalkyl.

In some embodiments, the compound of Formula (A) and Formula (I) is other than a compound selected from the group consisting of

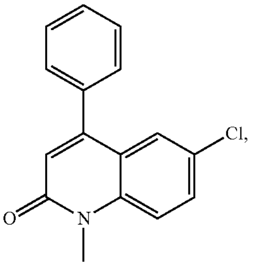

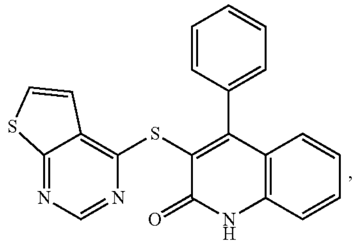

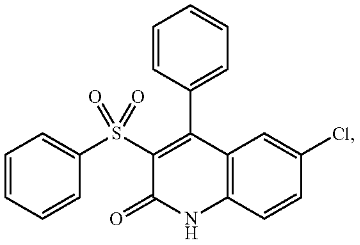

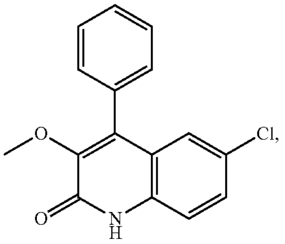

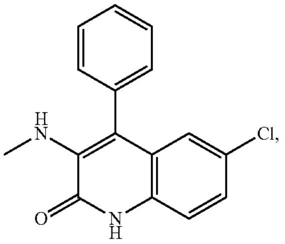

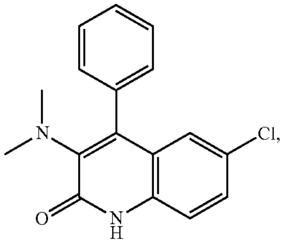

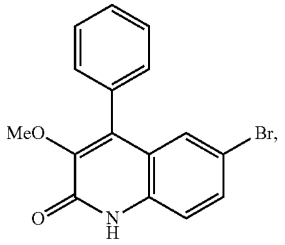

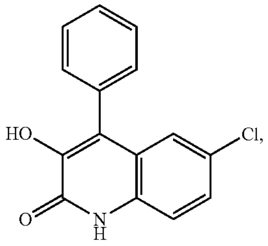 [SMILES: O=c1[nH]c2ccc(Cl)cc2c(-c2ccccc2)c1S]

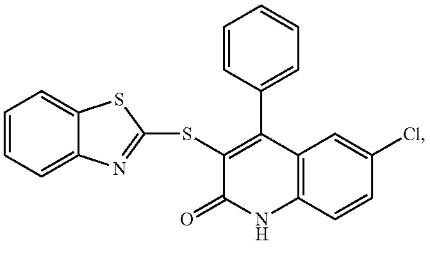

and

-continued

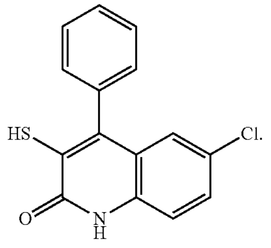

In a third aspect, provided is a pharmaceutical composition comprising a compound of Formula (A), Formula (I), a subembodiment described herein, or a pharmaceutically acceptable salt thereof and at least one pharmaceutically acceptable excipient.

In a fourth aspect, provided is a method for treating a disease mediated by MAT2A in a patient comprising administering to the patient a therapeutically effective amount of a compound of Formula (A), Formula (I), a subembodiment described herein, or a pharmaceutically acceptable salt thereof. In first embodiment of the third aspect, the patient is in recognized need of such treatment. In second embodiment of the third aspect and first embodiment contained therein, the compound of Formula (A), Formula (I), a subembodiment described herein, or a pharmaceutically acceptable salt thereof is administered in a pharmaceutical composition. In a third embodiment of the third aspect and first and second embodiments contained therein, the disease is mediated by overexpression of MAT2A. In fourth embodiment of the third aspect and first, second, and third embodiments contained therein, the disease is cancer.

In a fifth aspect, provided is a method of treating a MTAP null cancer in a patient comprising administering to the patient a therapeutically effective amount of a compound of Formula (A), Formula (I), a subembodiment described herein, or a pharmaceutically acceptable salt thereof. In first embodiment of the fourth aspect, the patient is in recognized need of such treatment. In second embodiment of the fourth aspect and first embodiment contained therein, the compound of Formula (A), Formula (I), a subembodiment described herein, or a pharmaceutically acceptable salt thereof is administered in a pharmaceutical composition.

In a sixth aspect, provided is a method for inhibiting the synthesis of S-adenosyl methionine (SAM) from methionine and ATP by MAT2A in a cell comprising contacting the cell with an effective amount of a compound of Formula (A), Formula (I), a subembodiment described herein, or a pharmaceutically acceptable salt thereof.

In a seventh aspect, provided is a method for treating a cancer in a patient, wherein the cancer is characterized by a reduction or absence of methylthioadenosine phosphorylase (MTAP) gene expression, the absence of the MTAP gene, or reduced function of MTAP protein, comprising administering to the subject a therapeutically effective amount of a compound of Formula (A), Formula (I), a subembodiment described herein, or a pharmaceutically acceptable salt thereof optionally in a pharmaceutical composition.

In a eighth aspect, provided is a compound of Formula (A), Formula (I) a subembodiment described herein, or a pharmaceutically acceptable salt thereof for inhibiting the synthesis of S-adenosyl methionine (SAM) from methionine and ATP by MAT2A in a cell.

In an ninth aspect, provided a compound of Formula (A), Formula (I), a subembodiment described herein, or a pharmaceutically acceptable salt thereof for use in the treatment of a disease in a patient, wherein the disease is mediated by the overexpression of MAT2A.

In a tenth aspect, provided a compound of Formula (A), Formula (I), a subembodiment described herein, or a pharmaceutically acceptable salt thereof for use in the treatment a cancer in a patient, wherein the cancer is characterized by a reduction or absence of methylthioadenosine phosphorylase (MTAP) gene expression, the absence of the MTAP gene, or reduced function of MTAP protein.

In an eleventh aspect, provided is a method for treating a cancer in a patient, wherein the cancer is characterized by a reduction or absence of methylthioadenosine phosphorylase (MTAP) gene expression, the absence of the MTAP gene, reduced level of MTAP protein, or reduced function of MTAP protein, comprising administering to the subject a therapeutically effective amount of a compound of Formula (A), Formula (I), a subembodiment described herein, or a pharmaceutically acceptable salt thereof optionally in a pharmaceutical composition.

In a twelfth aspect, provided a compound of Formula (A), Formula (I), a subembodiment described herein, or a pharmaceutically acceptable salt thereof for use in the treatment a cancer in a patient, wherein the cancer is characterized by a reduction or absence of methylthioadenosine phosphorylase (MTAP) gene expression, the absence of the MTAP gene, reduced level of MTAP protein or reduced function of MTAP protein.

DETAILED DESCRIPTION

Before the present invention is further described, it is to be understood that the invention is not limited to the particular embodiments set forth herein, and it is also to be understood that the terminology used herein is for the purpose of describing particular embodiments only, and is not intended to be limiting.

The singular forms "a," "an," and "the" as used herein and in the appended claims include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

The publications discussed herein are provided solely for their disclosure prior to the filing date of the present application. Further, the dates of publication provided may be different from the actual publication dates, which may need to be independently confirmed.

Definitions

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like. It will be recognized by a person skilled in the art that the term "alkyl" may include "alkylene" groups.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkoxy" means a —OR radical where R is alkyl as defined above, e.g., methoxy, ethoxy, propoxy, or 2-propoxy, n-, iso-, or tert-butoxy, and the like.

"Haloalkoxy" means an alkoxy radical, as defined above, which is substituted with one to five halogen atoms, such as fluorine or chlorine, including those substituted with different halogens, e.g., $—OCH_2Cl$, $—OCF_3$, $—OCHF_2$, $—OCH_2CF_3$, $—OCF_2CF_3$, $—OCF(CH_3)_2$, and the like.

"Aryl" means a monovalent monocyclic or bicyclic aromatic hydrocarbon radical of 6 to 10 ring atoms e.g., phenyl or naphthyl.

"Cycloalkyl" means a monocyclic monovalent hydrocarbon radical of three to eight carbon atoms which may be saturated or contains one double bond. Cycloalkyl may be unsubstituted or substituted with one or two substituents independently selected from alkyl, halo, alkoxy, hydroxy, or cyano. Examples include, but are not limited to, cyclopropyl, cyclobutyl, cyclopentyl, cyclohexyl, 1-cyanocycloprop-1-yl, 1-cyanomethylcycloprop-1-yl, 3-fluorocyclohexyl, and the like. When cycloalkyl contains a double bond, it may be referred to herein as cycloalkenyl.

"Halo" means fluoro, chloro, bromo, or iodo, preferably fluoro or chloro.

"Haloalkyl" means alkyl radical as defined above, which is substituted with one to five halogen atoms, such as fluorine or chlorine, including those substituted with different halogens, e.g., $—CH_2Cl$, $—CF_3$, $—CHF_2$, $—CH_2CF_3$, $—CF_2CF_3$, $—CF(CH_3)_2$, and the like. When the alkyl is substituted with only fluoro, it can be referred to in this Application as fluoroalkyl.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O, or S, the remaining ring atoms being carbon. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl, and the like. As defined herein, the terms "heteroaryl" and "aryl" are mutually exclusive. When the heteroaryl ring contains 5- or 6 ring atoms it is also referred to herein as 5- or 6-membered heteroaryl.

"Heterocycloalkyl" means a saturated or unsaturated monovalent monocyclic group of 4 to 8 ring atoms in which one or two ring atoms are heteroatom selected from N, O, or $S(O)_n$, where n is an integer from 0 to 2, the remaining ring atoms being C. Additionally, one or two ring carbon atoms in the heterocycloalkyl ring can optionally be replaced by a —CO— group. More specifically the term heterocycloalkyl includes, but is not limited to, azetidinyl, oxetanyl, pyrrolidino, piperidino, homopiperidino, 2-oxopyrrolidinyl, 2-oxopiperidinyl, morpholino, piperazino, tetrahydro-pyranyl, thiomorpholino, and the like. When the heterocycloalkyl ring is unsaturated it can contain one or two ring double bonds provided that the ring is not aromatic.

"Oxo," as used herein, alone or in combination, refers to =(0).

"Pharmaceutically acceptable salts" as used herein is meant to include salts of the active compounds which are prepared with relatively nontoxic acids or bases, depending on the particular substituents found on the compounds described herein. When compounds disclosed herein contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogen carbonic, phosphoric, monohydrogen phosphoric, dihydrogen phosphoric, sulfuric, monohydrogen sulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The present disclosure also includes protected derivatives of compounds of the present disclosure. For example, when compounds of the present disclosure contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis,* 5$^{th}$ Ed., John Wiley & Sons, Inc. (2014), the disclosure of which is incorporated herein by reference in its entirety. The protected derivatives of compounds of the present disclosure can be prepared by methods well known in the art.

The present disclosure also includes prodrugs of the compound of Formula (A), Formula (I), a subembodiment described herein, or a pharmaceutically acceptable salt thereof. Prodrugs of the compounds described herein are those compounds that readily undergo chemical changes under physiological conditions to provide the compounds of the present invention. An example, without limitation, of a prodrug would be a compound which is administered as an ester (the "prodrug"), but then is metabolically hydrolyzed to the carboxylic acid, the active entity. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of Formula (A), Formula (I) or a subembodiment described herein can exist in unsolvated forms as well as solvated forms, including hydrated forms. In general, the solvated forms are equivalent to unsolvated forms and are intended to be encompassed within the scope of the present invention. Certain compounds of Formula (A), Formula (I) or a subembodiment described herein may exist in multiple crystalline or amorphous forms. In general, all physical forms are equivalent for the uses contemplated by the present disclosure and are intended to be within the scope of the present disclosure.

Certain compounds of Formula (A), Formula (I) or a subembodiment described herein possess asymmetric carbon atoms (optical centers) or double bonds; the racemates, diastereomers, geometric isomers, regioisomers and individual isomers (e.g., separate enantiomers) are all intended to be encompassed within the scope of the present invention. Also within the scope of the present disclosure are atropisomers (isomers based on axial chirality resulting from restricted rotation in the molecule) of Formula (A), Formula (I) or a subembodiment described herein. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of Formula (A), Formula (I) or a subembodiment described herein may also contain unnatural amounts of isotopes at one or more of the atoms that constitute such compounds. Unnatural amounts of an isotope may be defined as ranging from the amount found in nature to an amount 100% of the atom in question. that differ only in the presence of one or more isotopically enriched atoms. Exemplary isotopes that can be incorporated into compounds of the present invention, such as a compound of Formula (A), Formula (I), a subembodiment described herein (including specific compounds) include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, in compounds disclosed herein, including in Table 1 below one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{15}F$ are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

"Pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"About," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass ±10%, preferably ±5%, the recited value and the range is included.

"Disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

"Patient" is generally synonymous with the term "subject" and as used herein includes all mammals including humans. Examples of patients include humans, livestock such as cows, goats, sheep, pigs, and rabbits, and companion animals such as dogs, cats, rabbits, and horses. Preferably, the patient is a human.

"In need of treatment" as used herein refers to a judgment made by a physician or other caregiver that a subject requires or will benefit from treatment. This judgment is made based on a variety of factors that are in the realm of the physician's or caregiver's expertise.

"Administration", "administer" and the like, as they apply to, for example, a patient, cell, tissue, organ, or biological fluid, refer to contact of, for example, a compound of Formula (A), Formula (I), a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

"Therapeutically effective amount" as used herein means the amount of a compound of Formula (A), Formula (I) or a subembodiment described herein and/or a pharmaceutically acceptable salt thereof that, when administered to a patient for treating a disease either alone or as part of a pharmaceutical composition and either in a single dose or as part of a series of doses, is sufficient to affect such treatment for the disease. The "therapeutically effective amount" will vary depending on the compound, the disease and its severity and the age, weight, etc., of the mammal to be treated. The therapeutically effective amount can be ascertained by measuring relevant physiological effects, and it can be adjusted in connection with the dosing regimen and diagnostic analysis of the subject's condition, and the like. By way of example, measurement of the serum level of a compound of Formula (A), Formula (I) or a subembodiment described herein (or, e.g., a metabolite thereof) at a particular time post-administration may be indicative of whether a therapeutically effective amount has been used.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

"Inhibiting", "reducing," or any variation of these terms in relation of MAT2A, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of MAT2A activity compared to its normal activity.

Compounds of Formula (I)

In some aspects, provided herein are compound having the Formula (A)

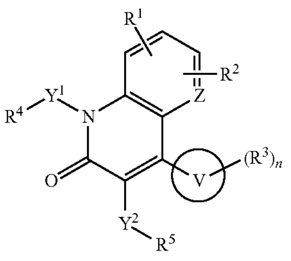

(A)

or a pharmaceutically acceptable salt thereof, wherein

Z is selected from the group consisting of CH and N;

$R^1$ and $R^2$ are each independently selected from the group consisting of H, $C_{1-6}$ alkyl, $C_{1-6}$ haloalkyl, $C_{1-6}$ alkoxy, $C_{1-6}$ haloalkoxy, cyano, halo and $C_{3-8}$ cycloalkyl, wherein the cycloalkyl group is substituted with from 0 to 2 groups independently selected from the group consisting of $C_{1-4}$ alkyl and halo;

ring V is a phenyl or a 5- to 6-membered heteroaryl comprising 1 to 3 heteroatom ring vertices independently selected from the group consisting of N, O, and S;

each $R^3$ is independently selected from the group consisting of halo, $C_{1-4}$ alkyl, $C_{1-4}$ haloalkyl, —$OR^z$, and —$X^4$—$OR^z$, wherein each $R^z$ is selected from the group consisting of H, $C_{1-4}$ alkyl, and $C_{1-4}$ haloalkyl, and each $X^4$ is $C_{1-3}$ alkylene;

the subscript n is 0, 1 or 2;

$Y^1$ is selected from the group consisting of a bond and $C_{1-4}$ alkylene;

$R^4$ is selected from the group consisting of H, halo, $C_{1-6}$ alkyl, $C_{1-6}$ haloalkyl, $C_{6-10}$ aryl, —$NR^aR^b$, —$C(O)R^d$, —$C(O)OR^d$, —$C(O)NR^aR^b$, and a 6- to 10-membered heteroaryl ring having 1 to 3 heteroatom ring vertices independently selected from the group consisting of N, O, and S; wherein $R^a$ and $R^b$ are each independently selected from the group consisting of H, $C_{1-6}$ alkyl, $C_{1-6}$ haloalkyl, and phenyl; wherein the phenyl is substituted with 0 to 2 moieties independently selected from the group consisting of $C_{1-4}$ alkyl, —$OR^x$, and —$X^2$—$OR^x$, and wherein each $R^x$ is selected from the group consisting of H, $C_{1-4}$ alkyl, and $C_{1-4}$ haloalkyl, and each $X^2$ is $C_{1-3}$ alkylene;

$R^d$ is selected from the group consisting of H, $C_{1-6}$ alkyl, and $C_{1-6}$ haloalkyl;

$Y^2$ is selected from the group consisting of a bond and $C_{1-4}$ alkylene;

$R^5$ is selected from the group consisting of H, halo, cyano, $C_{1-6}$ alkyl, $C_{1-6}$ haloalkyl, —$OR^c$, —O—$X^1$—$R^c$, —$SR^c$, —S—$X^1$—$R^c$, —$NR^fR^g$, —$S(O)_2R^c$, —$S(O)_2$—$X^1$—$R^c$, —$S(O)_2$—$NR^h$—$R^c$, —$S(O)_2$—$NR^h$—$X^1$—$R^c$, —$NR^h$—$S(O)_2$—$R^c$, —$NR^h$—$S(O)_2$—$X^1$—$R^c$, and a 3- to 6-membered heterocycloalkyl having 1 to 3 heteroatom ring vertices independently selected from the group consisting of N, O, and S;

$X^1$ is selected from the group consisting of a bond and $C_{1-4}$ alkylene;

$R^c$ is selected from the group consisting of H, $C_{1-6}$ alkyl, $C_{1-6}$ haloalkyl, $C_{3-8}$ cycloalkyl, $C_{6-10}$ aryl, a 3- to 6-membered heterocycloalkyl having 1 to 3 heteroatom ring vertices independently selected from N, O, and S, and a 5- to 10-membered heteroaryl having 1 to 4 heteroatom ring vertices independently selected from the group consisting of N, O, and S, wherein the $C_{3-8}$ cycloalkyl, the $C_6$_o aryl, the 3- to 6-membered heterocycloalkyl, and the 5- to 10-membered heteroaryl are substituted with 0 to 2 moieties independently selected from the group consisting of $C_{1-4}$ alkyl, —$OR^y$, —$X^3$—$OR^y$, —$C(O)R^y$, —$X^3$—$C(O)R^y$, —$C(O)OR^y$, and —$X^3$—$C(O)OR^y$, wherein each $R^y$ is selected from the group consisting of H, $C_{1-6}$ alkyl, and $C_{1-6}$ haloalkyl, and each $X^3$ is $C_{1-3}$ alkylene;

$R^f$ and $R^g$ are each independently selected from the group consisting of H, $C_{1-6}$ alkyl, $C_{1-6}$ haloalkyl, and phenyl; or $R^f$ and $R^g$ together with the nitrogen to which they are attached combine to form a 4- to 6-membered heterocycloalkyl ring comprising 0 to 2 additional heteroatoms independently selected from the group consisting of N, O, and S, wherein the phenyl and the 4- to 6-membered heterocycloalkyl are substituted with 0 to 2 moieties independently selected from the group consisting of $C_{1-4}$ alkyl, —$OR^x$, and —$X^2$—$OR^x$, wherein each $R^x$ is selected from the group consisting of H, $C_{1-4}$ alkyl, and $C_{1-4}$ haloalkyl, and each $X^2$ is $C_{1-3}$ alkylene;

$R^h$ is selected from the group consisting of H, $C_{1-6}$ alkyl and $C_{1-6}$ haloalkyl.

In some embodiments, ring V in Formula (A) is phenyl.

In some embodiments ring V in Formula (A) is a 5 membered heteroaryl comprising 1 to 3 heteroatom ring vertices independently selected from the group consisting of N, O, and S. In some embodiments, ring V in Formula (A) is a 6 membered heteroaryl comprising 1 to 3 heteroatom ring vertices independently selected from the group consisting of N, O, and S.

In some embodiments, ring V in Formula (A) is selected from the group consisting of pyrroylyl, pyrazolyl, and triazolyl. In some embodiments ring V in Formula (A) is pyrazolyl.

In some embodiments, ring V in Formula (A) is selected from the group consisting of pyridyl, pyridazinyl, pyrazinyl, pyrimindinyl, and triazinyl. In some embodiments, ring V in Formula (A) is pyridyl. In some embodiments, ring V in Formula (A) is pyrazinyl.

In some aspects, provided herein are compounds having the Formula (I)

(I)

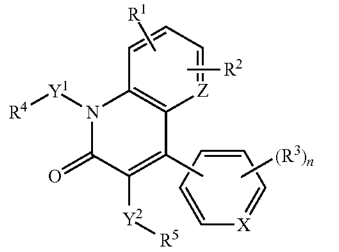

or a pharmaceutically acceptable salt thereof, wherein

Z is selected from the group consisting of CH and N;

$R^1$ and $R^2$ are each independently selected from the group consisting of H, $C_{1-6}$ alkyl, $C_{1-6}$ haloalkyl, $C_{1-6}$ alkoxy, cyano, halo and $C_{3-8}$ cycloalkyl, wherein the cycloalkyl group is substituted with from 0 to 2 groups independently selected from the group consisting of $C_{1-4}$ alkyl and halo;

X is CH, $CR^3$, or N;

each $R^3$ is independently selected from the group consisting of halo, $C_{1-4}$ alkyl, $C_{1-4}$ haloalkyl, —$OR^z$, and —$X^4$—$OR^z$, wherein each $R^z$ is selected from the group consisting of H, $C_{1-4}$ alkyl, and $C_{1-4}$ haloalkyl, and each $X^4$ is $C_{1-3}$ alkylene;

the subscript n is 0, 1 or 2;

$Y^1$ is selected from the group consisting of a bond and $C_{1-4}$ alkylene;

$R^4$ is selected from the group consisting of H, halo, $C_{1-6}$ alkyl, $C_{1-6}$ haloalkyl, $C_{6-10}$ aryl, —$NR^aR^b$, —C(O)$R^d$, —C(O)$OR^d$, —C(O)$NR^aR^b$, and a 6- to 10-membered heteroaryl ring having 1 to 3 heteroatom ring vertices independently selected from the group consisting of N, O, and S; wherein $R^a$ and $R^b$ are each independently selected from the group consisting of H, $C_{1-6}$ alkyl, $C_{1-6}$ haloalkyl, and phenyl; wherein the phenyl is substituted with 0 to 2 moieties independently selected from the group consisting of $C_{1-4}$ alkyl, —$OR^x$, and —$X^2$—$OR^x$, and wherein each $R^x$ is selected from the group consisting of H, $C_{1-4}$ alkyl, and $C_{1-4}$ haloalkyl, and each $X^2$ is $C_{1-3}$ alkylene;

$R^d$ is selected from the group consisting of H, $C_{1-6}$ alkyl, and $C_{1-6}$ haloalkyl;

$Y^2$ is selected from the group consisting of a bond and $C_{1-4}$ alkylene;

$R^5$ is selected from the group consisting of H, halo, cyano, $C_{1-6}$ alkyl, $C_{1-6}$ haloalkyl, —$OR^c$, —O—$X^1$—$R^c$, —$SR^c$, —S—$X^1$—$R^c$, —$NR^fR^g$, —$S(O)_2R^c$, —$S(O)_2$—$X^1$—$R^c$, —$S(O)_2$—$NR^h$—$R^c$, —$S(O)_2$—$NR^h$—$X^1$—$R^c$, —$NR^h$—$S(O)_2$—$R^c$, —$NR^h$—$S(O)_2$—$X^1$—$R^c$, and a 3- to 6-membered heterocycloalkyl having 1 to 3 heteroatom ring vertices independently selected from the group consisting of N, O, and S;

$X^1$ is selected from the group consisting of a bond and $C_{1-4}$ alkylene;

$R^c$ is selected from the group consisting of H, $C_{1-6}$ alkyl, $C_{1-6}$ haloalkyl, $C_{3-8}$ cycloalkyl, $C_{6-10}$ aryl, a 3- to 6-membered heterocycloalkyl having 1 to 3 heteroatom ring vertices independently selected from N, O, and S, and a 5- to 10-membered heteroaryl having 1 to 4 heteroatom ring vertices independently selected from the group consisting of N, O, and S, wherein the $C_{3-8}$ cycloalkyl, the $C_{6-10}$ aryl, the 3- to 6-membered heterocycloalkyl, and the 5- to 10-membered heteroaryl are substituted with 0 to 2 moieties independently selected from the group consisting of $C_{1-4}$ alkyl, —$OR^y$, —$X^3$—$OR^y$, —C(O)$R^y$, —$X^3$—C(O)$R^y$, —C(O)$OR^y$, and —$X^3$—C(O)$OR^y$, wherein each $R^y$ is selected from the group consisting of H, $C_{1-6}$ alkyl, and $C_{1-6}$ haloalkyl, and each $X^3$ is $C_{1-3}$ alkylene;

$R^f$ and $R^g$ are each independently selected from the group consisting of H, $C_{1-6}$ alkyl, $C_{1-6}$ haloalkyl, and phenyl; or $R^f$ and $R^g$ together with the nitrogen to which they are attached combine to form a 4- to 6-membered heterocycloalkyl ring comprising 0 to 2 additional heteroatoms independently selected from the group consisting of N, O, and S, wherein the phenyl and the 4- to 6-membered heterocycloalkyl are substituted with 0 to 2 moieties independently selected from the group consisting of $C_{1-4}$ alkyl, —$OR^x$, and —$X^2$—$OR^x$, wherein each $R^x$ is selected from the group consisting of H, $C_{1-4}$ alkyl, and $C_{1-4}$ haloalkyl, and each $X^2$ is $C_{1-3}$ alkylene;

$R^h$ is selected from the group consisting of H, $C_{1-6}$ alkyl and $C_{1-6}$ haloalkyl.

In some embodiments, the compound of Formula (A), Formula (I), or a subembodiment thereof is other than a compound selected from the group consisting of

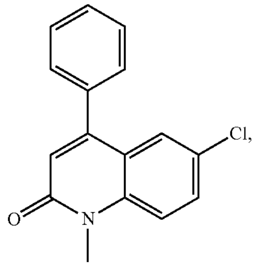

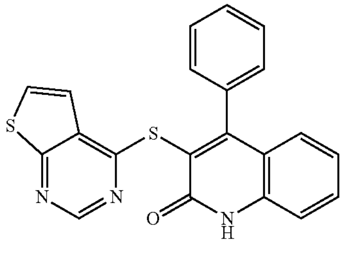

,

-continued

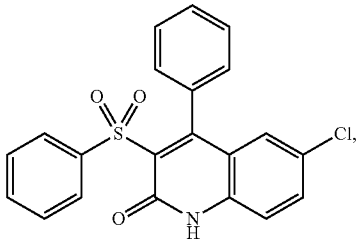

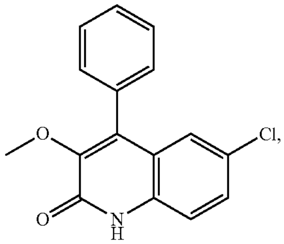

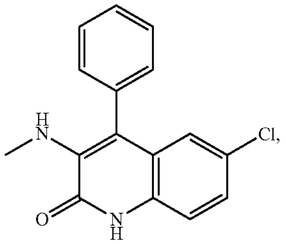

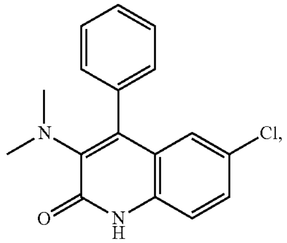

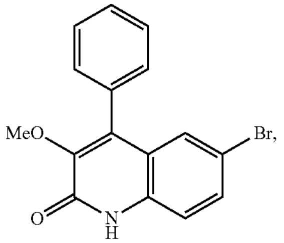

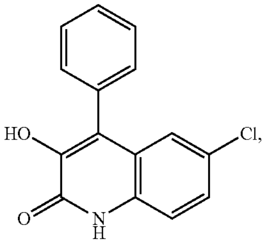 [SMILES: O=c1[nH]c2ccc(Cl)cc2c(-c2ccccc2)c1S]

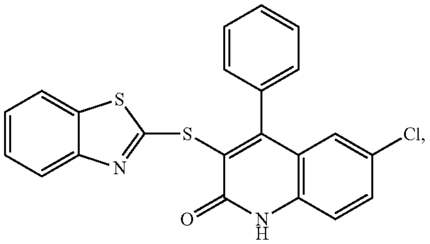

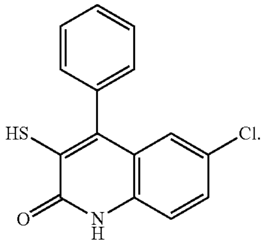

In some embodiments, the compounds described herein are represented by Formula (Ia)

(Ia)

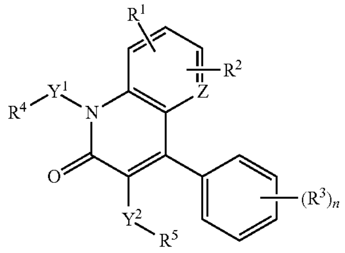

or a pharmaceutically acceptable salt thereof.

In some embodiments, the compounds described herein are represented by Formula (Ib)

(Ib)

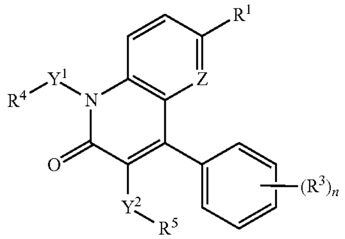

or a pharmaceutically acceptable salt thereof.

In some embodiments, the compounds described herein are represented by Formula (Ic)

(Ic)

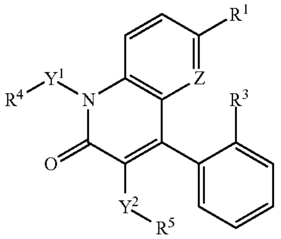

or a pharmaceutically acceptable salt thereof.

In some embodiments, the compounds described herein are represented by Formula (Id)

(Id)

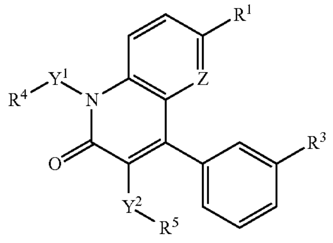

or a pharmaceutically acceptable salt thereof.

In some embodiments, the compounds described herein are represented by Formula (Ie)

(Ie)

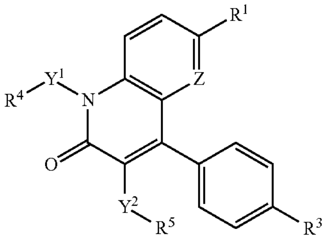

or a pharmaceutically acceptable salt thereof.

In some embodiments, the compounds described herein are represented by Formula (If)

(If)

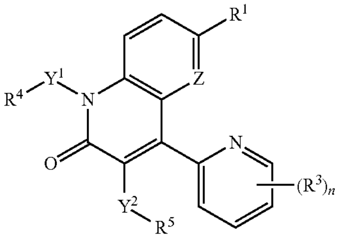

or a pharmaceutically acceptable salt thereof.

In some embodiments, the compounds described herein are represented by Formula (Ig)

(Ig)

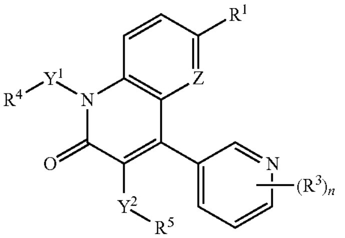

or a pharmaceutically acceptable salt thereof.

In some embodiments, the compounds described herein are represented by Formula (Ih)

(Ih)

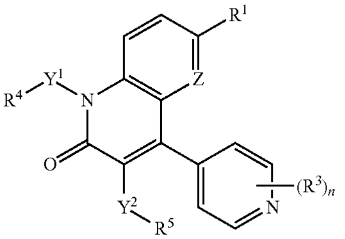

or a pharmaceutically acceptable salt thereof.

In some embodiments of Formula (A), Formula (I) and relevant subembodiments thereof, Z is CH. In some embodiments of Formula (A), Formula (I) and relevant subembodiments thereof, Z is N.

In some embodiments of Formula (A), Formula (I) and relevant subembodiments thereof, $R^1$ is selected from the group consisting of $C_{1-6}$ alkyl, $C_{1-6}$ haloalkyl, halo, $C_{1-6}$ alkoxy, $C_{1-6}$ haloalkoxy, and $C_{3-8}$ cycloalkyl, wherein the cycloalkyl group is substituted with from 0 to 2 groups selected from the group consisting of $C_{1-4}$ alkyl and halo. In some embodiments of Formula (A), Formula (I) and relevant subembodiments thereof, $R^1$ is selected from the group consisting of $C_{1-6}$ alkyl, $C_{1-6}$ haloalkyl, halo, and $C_{3-8}$ cycloalkyl, wherein the cycloalkyl group substituted with from 0 to 2 groups independently selected from the group consisting of $C_{1-4}$ alkyl and halo. In some embodiments of Formula (A), Formula (I) and relevant subembodiments thereof, $R^1$ is selected from the group consisting of $C_{1-2}$ alkyl, $C_{1-2}$ haloalkyl, and halo. In some embodiments of Formula (A), Formula (I) and relevant subembodiments thereof, $R^1$ is selected from the group consisting of methyl, trifluoromethyl, chloro, bromo, fluoro, and cyclopropyl.

In some embodiments of Formula (A), Formula (I) and relevant subembodiments thereof, $R^1$ is methyl. In some embodiments of Formula (A), Formula (I) and relevant subembodiments thereof, $R^1$ is trifluoromethyl. In some embodiments of Formula (A), Formula (I) and relevant subembodiments thereof, $R^1$ is chloro. In some embodiments of Formula (A), Formula (I) and relevant subembodiments thereof, $R^1$ is fluoro. In some embodiments of Formula (A), Formula (I) and relevant subembodiments thereof, $R^1$ is bromo. In some embodiments of Formula (A), Formula (I) and relevant subembodiments thereof, $R^1$ is cyclopropyl.

In some embodiments of Formula (A), Formula (I) and relevant subembodiments thereof, $R^2$ is selected from the group consisting of H, $C_{1-2}$ alkyl, halo, and $C_{1-2}$ alkoxy. In some embodiments of Formula (A), Formula (I) and relevant subembodiments thereof, $R^2$ is selected from the group consisting of H and methoxy.

In some embodiments of Formula (A), Formula (I) and relevant subembodiments thereof, $R^2$ is H. In some embodiments of Formula (A), Formula (I) and relevant subembodiments thereof, $R^2$ is methoxy.

In some embodiments of Formula (A), Formula (I) and relevant subembodiments thereof, each $R^3$ is independently selected from the group consisting of halo, $C_{1-4}$ alkyl, $C_{1-4}$ haloalkyl.

In some embodiments of Formula (A), Formula (I) and relevant subembodiments thereof, each $R^3$ is independently selected from the group consisting of $—OR^z$, and $—X^4—OR^z$.

In some embodiments, $R^z$ is H. In some embodiments, $R^z$ is $C_{1-4}$ alkyl.

In some embodiments of Formula (A), Formula (I) and relevant subembodiments thereof, each $R^3$ is independently selected from the group consisting of chloro, bromo, and methyl.

In some embodiments of Formula (A), Formula (I) and relevant subembodiments thereof, each $R^3$ is chloro. In some embodiments of Formula (A), Formula (I) and relevant subembodiments thereof, each $R^3$ is bromo. In some embodiments of Formula (A), Formula (I) and relevant subembodiments thereof, each $R^3$ is methyl.

In some embodiments of Formula (A), Formula (I) and relevant subembodiments thereof, the subscript n is 1. In some embodiments of Formula (A), Formula (I) and relevant subembodiments thereof, the subscript n is 0.

In some embodiments of Formula (A), Formula (I) and relevant subembodiments thereof, $Y^1$ is a bond. In some embodiments of Formula (A), Formula (I) and relevant subembodiments thereof, $Y^1$ is $C_{1-4}$ alkylene. In some embodiments of Formula (A), Formula (I) and relevant subembodiments thereof, $Y^1$ is methylene.

In some embodiments of Formula (A), Formula (I) and relevant subembodiments thereof, $R^4$ is selected from the group consisting of H, $C_{1-6}$ alkyl, $C_{1-6}$ haloalkyl, $C_{6-10}$ aryl, —$NR^aR^b$, —$C(O)NR^aR^b$, and a 6- to 10-membered heteroaryl ring having 1 to 3 heteroatom ring vertices independently selected from the group consisting of N, O, and S.

In some embodiments of Formula (A), Formula (I) and relevant subembodiments thereof, $R^4$ is H.

In some embodiments of Formula (A), Formula (I) and relevant subembodiments thereof, $R^4$ is selected from the group consisting of $C_{1-6}$ alkyl, $C_{1-6}$ haloalkyl, and phenyl.

In some embodiments of Formula (A), Formula (I) and relevant subembodiments thereof, $R^4$ is a 6- to 10-membered heteroaryl ring having 1 to 3 heteroatom ring vertices independently selected from the group consisting of N, O, and S. In some embodiments of Formula (A), Formula (I) and relevant subembodiments thereof, $R^4$ is pyrrole, pyrazole, imidazolyl, triazole, pyridinyl, pyrimidinyl, pyridazinyl, and pyrazinyl. In some embodiments of Formula (A), Formula (I) and relevant subembodiments thereof, $R^4$ is selected from the group consisting of pyridinyl and imidazolyl.

In some embodiments of Formula (A), Formula (I) and relevant subembodiments thereof, $R^4$ is selected from the group consisting of —$NR^aR^b$ and —$C(O)NR^aR^b$. In some embodiments of Formula (A), Formula (I) and relevant subembodiments thereof, $R^a$ and $R^b$ are each independently selected from the group consisting of H, methyl, phenyl, and toluenyl.

In some embodiments of Formula (A), Formula (I) and relevant subembodiments thereof, $R^a$ and $R^b$ are each H. In some embodiments of Formula (A), Formula (I) and relevant subembodiments thereof, $R^a$ and $R^b$ are each methyl. In some embodiments of Formula (A), Formula (I) and relevant subembodiments thereof, $R^a$ is H; and $R^b$ is methyl. In some embodiments of Formula (A), Formula (I) and relevant subembodiments thereof, $R^a$ is H; and $R^b$ is phenyl. In some embodiments of Formula (A), Formula (I) and relevant subembodiments thereof, $R^a$ is H; and $R^b$ is toluenyl.

In some embodiments of Formula (A), Formula (I) and relevant subembodiments thereof, $Y^2$ is a bond. In some embodiments of Formula (A), Formula (I) and relevant subembodiments thereof, $Y^2$ is $C_{1-4}$ alkylene. In some embodiments of Formula (A), Formula (I) and relevant subembodiments thereof, $Y^2$ is methylene.

In some embodiments of Formula (A), Formula (I) and relevant subembodiments thereof, $R^5$ is selected from the group consisting of H, halo, cyano, $C_{1-6}$ alkyl, and $C_{1-6}$ haloalkyl. In some embodiments of Formula (A), Formula (I) and relevant subembodiments thereof, $R^5$ is H. In some embodiments of Formula (A), Formula (I) and relevant subembodiments thereof, $R^5$ is selected from the group consisting of bromo, chloro, and iodo.

In some embodiments of Formula (A), Formula (I) and relevant subembodiments thereof, $R^5$ is cyano.

In some embodiments of Formula (A), Formula (I) and relevant subembodiments thereof, $R^5$ is —$NR^fR^g$. In some embodiments, $R^f$ and $R^g$ are each independently selected from the group consisting of H, $C_{1-6}$ alkyl, and $C_{1-6}$ haloalkyl.

In some embodiments of Formula (A), Formula (I) and relevant subembodiments thereof, $R^5$ is a 3- to 6-membered heterocycloalkyl having 1 to 3 heteroatom ring vertices independently selected from the group consisting of N, O, and S. In some embodiments, the 3- to 6-membered heterocycloalkyl is selected from the group consisting of pyrrolidinyl piperidinyl, tetrahydrofuranyl, and tetrahydropyranyl, and morpholinyl. In some embodiments, the 3- to 6-membered heterocycloalkyl is morpholinyl.

In some embodiments of Formula (A), Formula (I) and relevant subembodiments thereof, $R^5$ is selected from the group consisting of —$OR^c$, —O—$X^1$—$R^c$, —$SR^c$, —S—$X^1$—$R^c$, —$NR^fR^g$, —$S(O)_2R^c$, —$S(O)_2$—$X^1$—$R^c$, —$S(O)_2$—$NR^h$—$R^c$, and —$S(O)_2$—$NR^h$—$X^1$—$R^c$. In some embodiments of Formula (A), Formula (I) and relevant subembodiments thereof, $R^5$ is selected from the group consisting of —$OR^c$, —O—$X^1$—$R^c$, —$SR^c$, —S—$X^1$—$R^c$, —$S(O)_2R^c$, —$S(O)_2$—$X^1$—$R^c$, and —$S(O)_2$—NH—$R^c$. In some embodiments of Formula (A), Formula (I) and relevant subembodiments thereof, $R^5$ is selected from the group consisting of —$OR^c$ and —O—$X^1$—$R^c$. In some embodiments of Formula (A), Formula (I) and relevant subembodiments thereof, $R^5$ is selected from the group consisting of —$SR^c$, —S—$X^1$—$R^c$, and —$S(O)_2R^c$. In some embodiments of Formula (A), Formula (I) and relevant subembodiments thereof, $R^5$ is selected from the group consisting of —$S(O)_2R^c$, —$S(O)_2$—$X^1$—$R^c$, and —$S(O)_2$—NH—$R^c$.

In some embodiments of Formula (A), Formula (I) and relevant subembodiments thereof, $R^c$ is selected from the group consisting of H, $C_{1-6}$ alkyl, $C_{1-6}$ haloalkyl, $C_{3-8}$ cycloalkyl, $C_{6-10}$ aryl, a 3- to 6-membered heterocycloalkyl having 1 to 3 heteroatom ring vertices independently selected from N, O, and S, and a 5- to 10-membered heteroaryl having 1 to 4 heteroatom ring vertices independently selected from the group consisting of N, O, and S. In some embodiments, $R^c$ is H. In some embodiments, $R^c$ is selected from the group consisting of $C_{1-6}$ alkyl and $C_{1-6}$ haloalkyl. In some embodiments, $R^c$ is selected from the group consisting of $C_{3-6}$ cycloalkyl. In some embodiments, $R^c$ is phenyl. In some embodiments, $R^c$ is a 5- to 10-membered heteroaryl having 1 to 4 heteroatom ring vertices independently selected from the group consisting of N, O, and S. In some embodiments, the 5- to 10-membered heteroaryl is selected from the group consisting of thieno[3,2-d]pyrimidinyl, furo[3,2-d]pyrimidinyl, thio[3,2-b]pyridinyl furo[3,2-b]pyridinyl, benzo[b]thiophenyl, benzo benzothiazolyl, benzothiazolyl, pyrrole, pyrazole, imidazolyl, triazole, pyridinyl, pyrimidinyl, pyridazinyl, and pyrazinyl. In some embodiments, the 5- to 10-membered heteroaryl is selected from the group consisting of thieno[3,2-d]pyrimidinyl, benzothiazolyl, and triazole.

In some embodiments of Formula (A), Formula (I) and relevant subembodiments thereof, $R^c$ is a 3- to 6-membered heterocycloalkyl having 1 to 3 heteroatom ring vertices independently selected from the group consisting of N, O, and S. In some embodiments, the 3- to 6-membered heterocycloalkyl is selected from the group consisting of pyrrolidinyl piperidinyl, tetrahydrofuranyl, and tetrahydropyranyl, and morpholinyl. In some embodiments, the 3- to 6-membered heterocycloalkyl is tetrahydrofuranyl.

In some embodiments of Formula (A), Formula (I) and relevant subembodiments thereof, the compound is selected from a compound in Table 1 or a pharmaceutically acceptable salt thereof.

Representative Compounds are provided in Table 1 below:
TABLE 1
| Cpd. No. | Structure | $^1$H NMR | Mass Spec. [M + H]$^+$ |
|---|---|---|---|
| 1.001 | 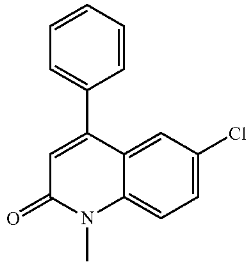 [SMILES: Cn1c(=O)cc(-c2ccccc2)c2cc(Cl)ccc21] | $^1$HNMR (400 MHz, DMSO-$d_6$) δ 7.73-7.65 (m, 2H), 7.59-7.55 (m, 3H), 7.47 (dd, J = 10.0, 3.0 Hz, 1H), 7.32 (d, J = 8.5 Hz, 1H), 6.58 (s, 1H), 3.67 (s, 3H). | 270.18 |
| 1.002 | 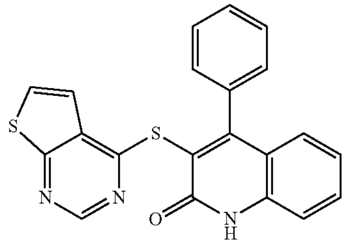 [SMILES: O=c1[nH]c2ccccc2c(-c2ccccc2)c1Sc1ncnc2sccc12] | $^1$HNMR (500 MHz, DMSO-$d_6$) δ 12.28 (br s, 1H), 8.74 (s, 1H), 7.93 (d, J = 6.0 Hz, 1H), 7.63-7.59 (m, 1H), 7.49-7.41 (m, 5H), 7.30-7.28 (m, 2H), 7.17-7.14 (m, 1H), 7.01 (dd, J = 8.5, 1.0 Hz, 1H). | 388.31 |
| 1.003 | 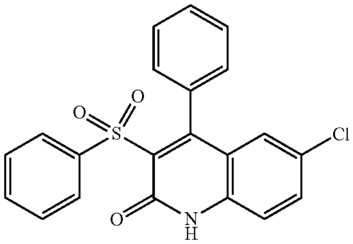 [SMILES: O=c1[nH]c2ccc(Cl)cc2c(-c2ccccc2)c1S(=O)(=O)c1ccccc1] | $^1$HNMR (500 MHz, DMSO-$d_6$) δ 12.44 (br s, 1H), 7.88-7.86 (m, 2H), 7.72-7.62 (m, 2H), 7.60-7.50 (m, 5H), 7.45-7.41 (m, 2H), 7.38 (d, J = 8.8 Hz, 1H), 6.74 (d, J = 2.4 Hz, 1H); LC-MS (ESI, m/z). | 396.37 |
| 1.004 | 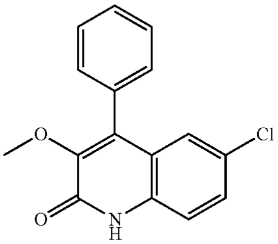 [SMILES: COc1c(-c2ccccc2)c2cc(Cl)ccc2[nH]c1=O] | $^1$HNMR (500 MHz, DMSO-$d_6$) δ 12.25 (s, 1H), 7.57-7.47 (m, 4H), 7.39-7.33 (m, 3H), 6.87 (d, J = 2.5 Hz, 1H), 3.71 (s, 3H). | 286.20 |
| 1.005 | 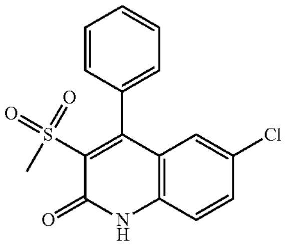 [SMILES: CS(=O)(=O)c1c(-c2ccccc2)c2cc(Cl)ccc2[nH]c1=O] | $^1$HNMR (500 MHz, DMSO-$d_6$) δ 12.70 (s, 1H), 7.72 (dd, J = 9.0, 2.5 Hz, 1H), 7.49-7.44 (m, 4H), 7.29-7.27 (m, 2H), 6.74 (d, J = 2.0 Hz, 1H), 3.47 (d, J = 11.0 Hz, 3H). | 334.18 |

TABLE 1-continued

| Cpd. No. | Structure | $^1$H NMR | Mass Spec. $[M + H]^+$ |
|---|---|---|---|
| 1.006 | 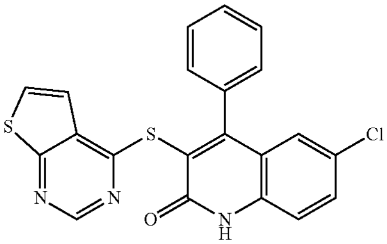 [SMILES: O=c1[nH]c2ccc(Cl)cc2c(-c2ccccc2)c1Sc1ncnc2sccc12] | $^1$HNMR (500 MHz, DMSO-$d_6$) δ 12.44 (s, 1H), 8.75 (s, 1H), 7.95 (d, J = 6 Hz, 1H), 7.70-7.68 (m, 1H), 7.50-7.46 (m, 5H), 7.33-7.31 (m, 2H), 6.92 (d, J = 2.5 Hz, 1H). | 422.24 |
| 1.007 | 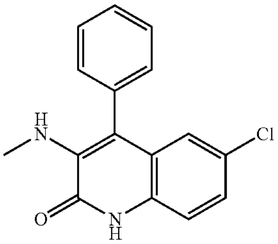 [SMILES: CNc1c(-c2ccccc2)c2cc(Cl)ccc2[nH]c1=O] | $^1$HNMR (500 MHz, DMSO-$d_6$) δ 12.15 (s, 1H), 7.52-7.44 (m, 3H), 7.37-7.35 (m, 2H), 7.25 (d, J = 8.5 Hz, 1H), 7.17 (dd, J = 8.5, 2.0 Hz, 1H), 6.65 (d, J = 2.0 Hz, 1H), 5.89 (q, J = 11.0 Hz, 1H), 2.19 (d, J = 6.0 Hz, 3H). | 285.21 |
| 1.008 | 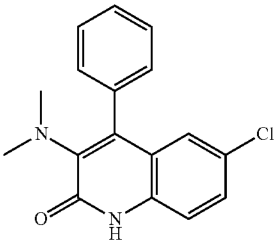 [SMILES: CN(C)c1c(-c2ccccc2)c2cc(Cl)ccc2[nH]c1=O] | $^1$HNMR (500 MHz, DMSO-$d_6$) δ 11.94 (s, 1H), 7.56-7.52 (m, 2H), 7.47-7.45 (m, 1H), 7.39-7.37 (m, 1H), 7.32-7.29 (m, 3H), 6.87 (d, J = 2.5 Hz, 1H), 2.50-2.48 (m, 6H). | 299.2 |
| 1.009 | 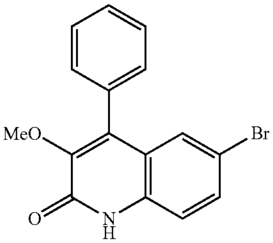 [SMILES: COc1c(-c2ccccc2)c2cc(Br)ccc2[nH]c1=O] | $^1$HNMR (500 MHz, DMSO-$d_6$) δ 12.25 (s, 1H), 7.60-7.54 (m, 3H), 7.51-7.48 (m, 1H), 7.35-7.32 (m, 3H), 7.01 (d, J = 2.0 Hz, 1H), 3.71 (s, 3H). | 330.25 |
| 1.010 | 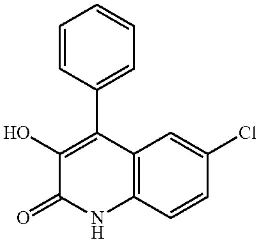 | $^1$HNMR (500 MHz, DMSO-$d_6$) δ 12.41 (s, 1H), 9.56 (s, 1H), 7.54-7.51 (m, 2H), 7.44-7.46 (m, 1H), 7.38-7.33 (m, 4H), 6.93 (t, J = 1.5 Hz, 1H). | 272.24 |
| 1.011 | 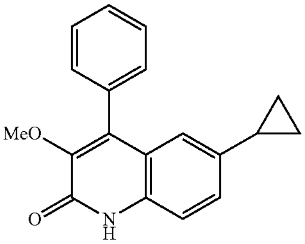 [SMILES: COc1c(-c2ccccc2)c2cc(C3CC3)ccc2[nH]c1=O] | $^1$HNMR (500 MHz, DMSO-$d_6$) δ 12.01 (s, 1H), 7.55-7.52 (m, 2H), 7.49-7.46 (m, 1H), 7.33-7.30 (m, 2H), 7.26 (d, J = 8.5 Hz, 1H), 7.10 (dd, J = 8.5, 2.0 Hz, 1H), 6.72 (d, J = 2.0 Hz, 1H), 3.67 (s, 3H), 1.82-1.77 (m, 1H), 0.85-0.81 (m, 2H), 0.47-0.46 (m, 2H). | 292.42 |

TABLE 1-continued

| Cpd. No. | Structure | $^1$H NMR | Mass Spec. $[M + H]^+$ |
|---|---|---|---|
| 1.012 | 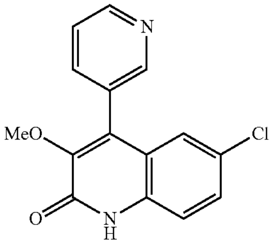 [SMILES: COc1c(-c2cccnc2)c2cc(Cl)ccc2[nH]c1=O] | $^1$HNMR (500 MHz, DMSO-$d_6$) δ 12.35 (s, 1H), 8.70 (dd, J = 5.0, 1.5 Hz, 1H), 8.57 (d, J = 1.5 Hz, 1H), 7.85-7.82 (m, 1H), 7.60-7.58 (m, 1H), 7.51 (dd, J = 9.0, 2.5 Hz, 1H), 7.41 (d, J = 9.0 Hz, 1H), 6.88 (d, J = 2.5 Hz, 1H), 3.76 (s, 3H). | 287.36 |
| 1.013 | 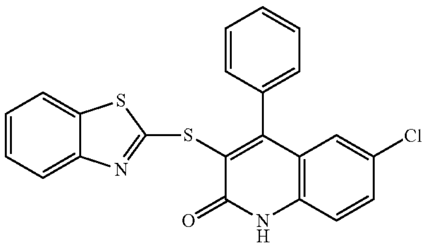 [SMILES: O=c1[nH]c2ccc(Cl)cc2c(-c2ccccc2)c1Sc1nc2ccccc2s1] | $^1$HNMR (500 MHz, DMSO-$d_6$) δ 12.85-12.51 (m, 1H), 7.93 (d, J = 0.5 Hz, 1H), 7.91 (d, J = 0.5 Hz, 1H), 7.80-7.70 (m, 1H), 7.56-7.50 (m, 4H), 7.49-7.42 (m, 1H), 7.42-7.30 (m, 3H), 6.92 (d, 2.0 Hz, 1H). | 421.36 |
| 1.014 | 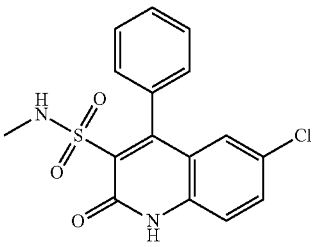 [SMILES: CNS(=O)(=O)c1c(-c2ccccc2)c2cc(Cl)ccc2[nH]c1=O] | $^1$HNMR (500 MHz, DMSO-$d_6$) δ 12.68 (br s, 1H), 7.69 (dd, J = 9.0, 2.5 Hz, 1H), 7.51-7.44 (m, 4H), 7.26-7.24 (m, 2H), 6.88-6.86 (m, 1H), 6.72 (d, J = 2.5 Hz, 1H), 2.44 (d, J = 5.0 Hz, 1H). | 349.35 |
| 1.015 | 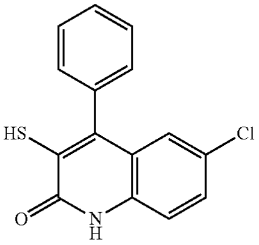 [SMILES: O=c1[nH]c2ccc(Cl)cc2c(-c2ccccc2)c1S] | $^1$HNMR (500 MHz, DMSO-$d_6$) δ 12.48 (s, 1H), 7.68-7.55 (m, 2H), 7.55-7.50 (m, 1H), 7.50-7.44 (m, 1H), 7.41 (d, J = 8.5 Hz, 1H), 7.33 (dd, J = 8.5, 1.5 Hz, 2H), 6.77 (d, J = 2.0 Hz, 1H). | 288.32 |
| 1.016 | 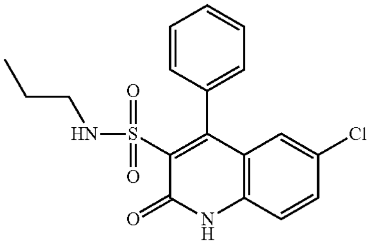 [SMILES: CCCNS(=O)(=O)c1c(-c2ccccc2)c2cc(Cl)ccc2[nH]c1=O] | $^1$HNMR (500 MHz, DMSO-$d_6$) δ 12.69 (s, 1H), 7.67 (dd, J = 9.0, 2.0 Hz, 1H), 7.52-7.43 (m, 4H), 7.23 (dd, J = 7.5, 1.5 Hz, 2H), 7.07 (br s, 1H), 6.72 (d, J = 2.5 Hz, 1H), 2.77-2.73 (m, 2H), 1.40-1.34 (m, 2H), 0.78 (t, J = 7.0 Hz, 3H). | 377.38 |
| 1.017 | 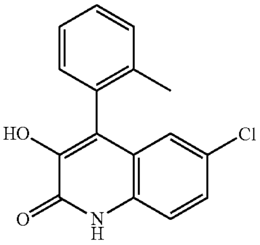 [SMILES: Cc1ccccc1-c1c(O)c(=O)[nH]c2ccc(Cl)cc12] | $^1$HNMR (500 MHz, DMSO-$d_6$) δ 12.39 (s, 1H), 9.56 (s, 1H), 7.40-7.31 (m, 5H), 7.13 (d, J = 7.5 Hz, 1H), 6.67 (s, 1H), 2.02(s, 3H). | 286.16 |

TABLE 1-continued

| Cpd. No. | Structure | $^1$H NMR | Mass Spec. $[M + H]^+$ |
|---|---|---|---|
| 1.018 | 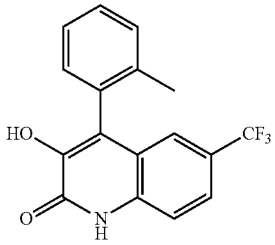 [SMILES: Cc1ccccc1-c1c(O)c(=O)[nH]c2ccc(C(F)(F)F)cc12] | $^1$HNMR (500 MHz, DMSO-$d_6$) δ 12.57 (s, 1H), 9.68 (s, 1H), 7.66-7.64 (m, 1H) 7.41-7.40 (m, 1H), 7.38-7.33 (m, 3H), 7.16 (d, J = 7.5 Hz, 1H), 7.00 (s, 1H), 2.02 (s, 3H). | 320.30 |
| 1.019 | 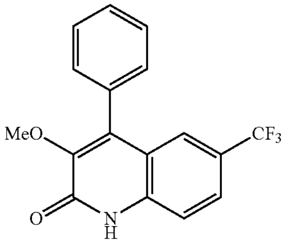 [SMILES: COc1c(-c2ccccc2)c2cc(C(F)(F)F)ccc2[nH]c1=O] | $^1$HNMR (500 MHz, DMSO-$d_6$) δ 12.473 (s, 1H), 7.77 (d, J = 1.5 Hz, 1H), 7.58-7.50 (m, 4H), 7.380-7.36 (m, 2H), 7.2 (s, 1H), 3.73 (s, 3H). | 320.30 |
| 1.020 | 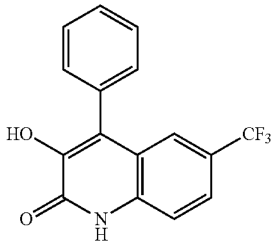 [SMILES: O=c1[nH]c2ccc(C(F)(F)F)cc2c(-c2ccccc2)c1O] | $^1$HNMR (500 MHz, DMSO-$d_6$) δ 12.80-12.41 (m, 1H), 9.89-9.45 (m, 1H), 7.66 (d, J = 9.0, 2.0 Hz, 1H), 7.56-7.45(m, 4H), 7.37-7.35 (m, 2H), 7.27 (d, J = 1.5 Hz, 1H). | 306.23 |
| 1.021 | 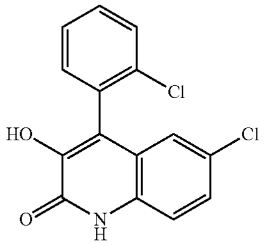 [SMILES: O=c1[nH]c2ccc(Cl)cc2c(-c2ccccc2Cl)c1O] | $^1$HNMR (500 MHz, DMSO-d6) δ 12.42-12.41 (m, 1H), 9.85-9.83 (m, 1H), 7.66-7.64 (m, 1H), 7.53-7.48 (m, 2H), 7.38-7.36 (m, 3H), 6.65(d, J = 1.5 Hz, 1H). | 306.17 |
| 1.022 | 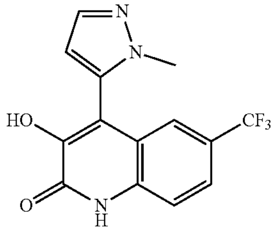 [SMILES: Cn1nccc1-c1c(O)c(=O)[nH]c2ccc(C(F)(F)F)cc12] | $^1$HNMR (500 MHz, DMSO-$d_6$) δ 12.65 (s, 1H), 10.47 (br s, 1H), 7.68 (d, J = 8.5 Hz, 1H), 7.61 (d, J = 2.0 Hz, 1H), 7.52 (d, J = 8.5 Hz, 1H), 7.35 (s, 1H), 6.42 (d, J = 1.5 Hz, 1H), 3.32 (s, 3H). | 310.0 |
| 1.023 | 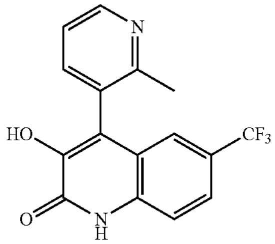 [SMILES: Cc1ncccc1-c1c(O)c(=O)[nH]c2ccc(C(F)(F)F)cc12] | $^1$HNMR (400 MHz, DMSO-$d_6$) δ 12.64 (s, 1H), 9.98 (br s, 1H), 8.57 (d, J = 3.6 Hz, 1H), 8.14 (s, 1H), 7.68 (d, J = 8.4 Hz, 1H), 7.63 (d, J = 7.6 Hz, 1H), 7.54 (d, J = 8.4 Hz, 1H), 7.40-7.35 (m, 1H), 6.98 (s, 1H), 2.23 (s, 3H). | 321.1 |

TABLE 1-continued

| Cpd. No. | Structure | $^1$H NMR | Mass Spec. [M + H]$^+$ |
|---|---|---|---|
| 1.024 | 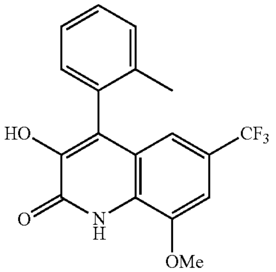 [SMILES: COc1cc(C(F)(F)F)cc2c(-c3ccccc3C)c(O)c(=O)[nH]c12] | $^1$HNMR (400 MHz, DMSO-$d_6$) δ 11.82 (s, 1H), 9.66 (s, 1H), 7.39-7.29 (m, 3H), 7.22-7.20 (m, 1H), 7.13 (d, J = 8 Hz, 1H), 6.62 (s, 1H), 3.98 (s, 3H), 1.99 (s, 3H). | 350.1 |
| 1.025 | 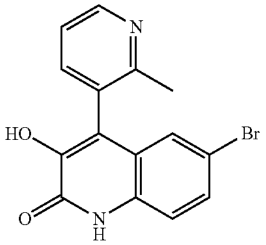 [SMILES: Cc1ncccc1-c1c(O)c(=O)[nH]c2ccc(Br)cc12] | $^1$HNMR (400 MHz, DMSO-$d_6$) δ 12.38 (br s, 1H), 9.90 (br s, 1H), 8.54 (dd, J = 4.8, 1.6 Hz, 1H), 7.58 (dd, J = 7.6 Hz, 1.6 Hz, 1H), 7.47 (d, J = 8.0 Hz, 1H), 7.36 (dd, J = 7.6, 4.8 Hz, 1H), 7.30 (d, J = 8.0 Hz, 1H), 6.79 (d, J = 2 Hz, 1H), 2.23 (s, 3H). | 331.0 |
| 1.026 | 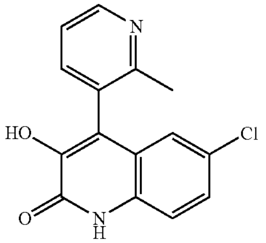 [SMILES: Cc1ncccc1-c1c(O)c(=O)[nH]c2ccc(Cl)cc12] | $^1$HNMR (400 MHz, DMSO-$d_6$) δ 12.42 (s, 1H), 9.84 (br s, 1H), 8.55 (dd, J = 4.8, 1.6 Hz, 1H), 7.60 (dd, J = 7.6, 1.6 Hz, 1H), 7.42-7.35 (m, 3H), 6.67 (s, 1H), 2.23 (s, 3H). | 287.1 |
| 1.027 | 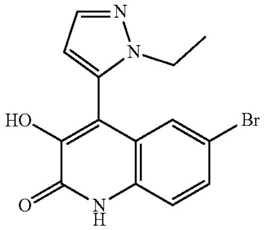 [SMILES: CCn1nccc1-c1c(O)c(=O)[nH]c2ccc(Br)cc12] | $^1$HNMR (400 MHz, DMSO-$d_6$) δ 12.32 (br s, 1H), 7.61 (s, 1H), 7.43 (dd, J = 8.4 Hz, 1H), 7.25 (d, J = 8.4 Hz, 1H), 7.03 (s, 1H), 6.30 (s, 1H), 3.87 (q, J = 7.2 Hz, 2H), 1.19 (t, J = 7.2 Hz, 3H). | 334.1 |
| 1.028 | 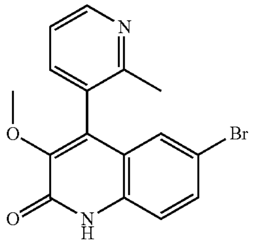 [SMILES: COc1c(-c2cccnc2C)c2cc(Br)ccc2[nH]c1=O] | $^1$HNMR (400 MHz, DMSO-$d_6$) δ 12.3 (br s, 1H), 8.59 (d, J = 4.8, 1.6 Hz, 1H), 7.65-7.58 (m, 2H), 7.42-7.32 (m, 2H), 7.79 (s, 1H), 3.73 (s, 3H), 2.22 (s, 3H). | 345.2 |

General Synthesis

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art reading this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C.

Compounds of Formula (I) and the subembodiments described herein where $R^1$, $R^2$, $R^3$, $R^4$ and $R^5$ and other groups are as defined in the Summary can be prepared the method illustrated and described in Scheme 1 below

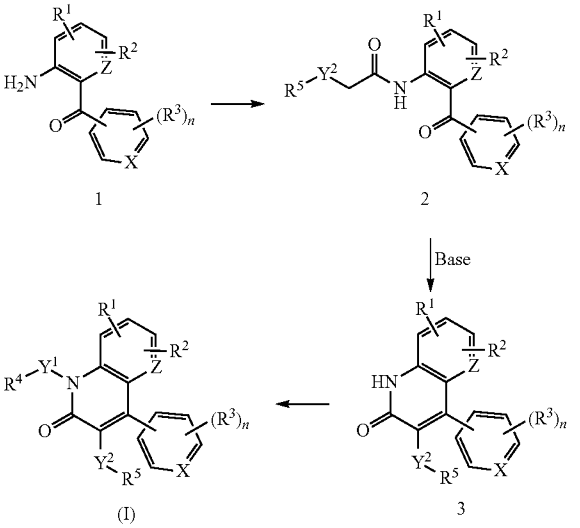

Compound for Formula (I), where $R^1$, $R^2$ and $R^3$ are as described in Summary or a precursor group thereof, can be readily converted to a compound of Formula (2) by methods well known in the art. For example, treatment of compound 1 with acetyl chloride in the presence of an organic base such as triethylamine in an inert organic solvent provides a compound of Formula (2), which can then be converted to compounds of Formula (3) by methods well known in the art such as adding a base. Compounds of Formula (I) can be prepared by treating corresponding compound of Formula (3) in the presence of a based and a electrophile. It is understood that replacement of the six membered cyclic moiety comprising ring vertex "X" with a five or six membered heteroaryl comprising 1 to 3 heteroatom ring vertices independently selected from the group consisting of N, O, and S can provide compounds of Formula (A).

Utility

Overexpression of the enzyme MAT2A has been demonstrated to mediate certain cancers. In an embodiment, the cancer is neuroblastoma, intestine carcinoma (such as rectum carcinoma, colon carcinoma, familiarly adenomatous polyposis carcinoma and hereditary non-polyposis colorectal cancer), esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors (such as glioblastoma, astrocytoma, meningioma, medulloblastoma and peripheral neuroectodermal tumors), Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma.

In another embodiment, the cancer is lung cancer, non-small cell lung (NSLC) cancer, bronchioloalveolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the vagina, carcinoma of the vulva, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including refractory versions of any of the above cancers, or a combination of one or more of the above cancers.

Methylthioadenosine phosphorylase (MTAP) is an enzyme found in all normal tissues that catalyzes the conversion of methylthioadenosine (MTA) into adenine and 5-methylthio-ribose-1-phosphate. The adenine is salvaged to generate adenosine monophosphate, and the 5-methylthioribose-1-phosphate is converted to methionine and formate. Because of this salvage pathway, MTA can serve as an alternative purine source when de novo purine synthesis is blocked, e.g., with antimetabolites, such as L-alanosine.

Many human and murine malignant cells lack MTAP activity. MTAP deficiency is not only found in tissue culture cells but the deficiency is also present in primary leukemias, gliomas, melanomas, pancreatic cancers, non-small cell lung cancers (NSLC), bladder cancers, astrocytomas, osteosarcomas, head and neck cancers, myxoid chondrosarcomas, ovarian cancers, endometrial cancers, breast cancers, soft tissue sarcomas, non-Hodgkin lymphomas, and mesotheliomas. It has been reported by K. Marjon et al., Cell Reports 15 (2016) 574-587, incorporated herein by reference, that proliferation of cancer cells that are MTAP null is inhibited by knocking down MAT2A expression with shRNA. An MTAP null cancer is a cancer in which the MTAP gene has been deleted or lost or otherwise deactivated or a cancer in which the MTAP protein has a reduced or impaired function.

Accordingly, in an embodiment of the present disclosure there is provided a method for treating an MTAP null cancer in a patient wherein said cancer is characterized by a reduction or absence of MTAP expression or absence of the MTAP gene or reduced function of MTAP protein as compared to cancers where the MTAP gene is present and fully functioning, said method comprising administering to the patient in need thereof a therapeutically effective amount of a compound of Formula (A), Formula (I) or a subembodiment described herein or a pharmaceutically acceptable salt thereof. In an embodiment of the present disclosure there is provided a method for treating an MTAP null cancer in a patient wherein said cancer is characterized by a reduction or absence of MTAP expression or absence of the MTAP gene, reduced level of MTAP protein, or reduced function of MTAP protein as compared to cancers where the MTAP gene is present and fully functioning, said method comprising administering to the patient in need thereof a therapeutically effective amount of a compound of Formula (A), Formula (I) or a subembodiment described herein or a pharmaceutically acceptable salt thereof. In another embodiment, provided is a method of treating an MTAP null cancer in a patient comprising administering to the patient in need thereof an effective amount of a compound of Formula (A), Formula (I) or a subembodiment described herein or a pharmaceutically acceptable salt thereof. In an embodiment, the MTAP null cancer is leukemia, glioma, melanoma, pancreatic, non-small cell lung cancer (NSLC), bladder cancer, astrocytoma, osteosarcoma, head and neck cancer, myxoid chondrosarcoma, ovarian cancer, endometrial cancer, breast cancer, soft tissue sarcoma, non-Hodgkin lymphoma or mesothelioma. In another embodiment, the MTAP null cancer is pancreatic cancer. In yet another embodiment, the MTAP null cancer is bladder cancer, melanoma, brain cancer, lung cancer, pancreatic cancer, breast cancer, esophageal cancer, head and neck cancer, kidney cancer, colon cancer, diffuse large B cell lymphoma (DLBCL), acute lymphoblastic leukemia (ALL) or mantle cell lymphoma (MCL). In yet another embodiment, the MTAP null cancer is gastric cancer. In yet another embodiment, the cancer is colon cancer. In yet another embodiment, the MTAP null cancer is liver cancer. In yet another embodiment, the MTAP null cancer is glioblastoma multiforme (GBM). In yet another embodiment, the MTAP null cancer is bladder cancer. In yet another embodiment, the MTAP null cancer is esophageal cancer. In yet another embodiment, the MTAP null cancer is breast cancer. In yet another embodiment, the MTAP null cancer is NSLCC. In yet another embodiment, the MTAP null cancer is MCL. In yet another embodiment, the MTAP null cancer is DLBCL. In yet another embodiment, the MTAP null cancer is ALL.

In another embodiment, the MTAP null cancer is solid tumor. In another embodiment, the MTAP null cancer is malignant solid tumor.

Genomic analysis of MTAP null cell lines has shown that cell lines that also incorporate a KRAS mutation or a p53 mutation were sensitive to MAT2A inhibition.

Accordingly, also provided is a method for treating a cancer in a patient wherein said cancer is characterized by reduction or absence of MTAP expression or absence of the MTAP gene or reduced function of MTAP protein (i.e., MTAP null) and further characterized by the presence of mutant KRAS and/or mutant p53, said method comprising administering to the patient a therapeutically effective amount of a compound of Formula (A), Formula (I) or a subembodiment described herein. In one embodiment, the cancer is MTAP null and KRAS mutant. In another embodiment, the cancer is MTAP null and p53 mutant. In yet another embodiment, the cancer is MTAP null, KRAS mutant and p53 mutant.

The term "mutant KRAS" or "KRAS mutation" refers to KRAS protein (or gene encoding said protein) incorporating an activating mutation that alters its normal function. For example, a mutant KRAS protein may incorporate a single amino acid substitution at position 12 or 13. In a particular embodiment, the KRAS mutant incorporates a G12X or G13X substitution, wherein X represents any amino acid change at the indicated position. In a particular embodiment, the substitution is G12V, G12R, G12C or G13D. In another embodiment, the substitution is G13D. By "mutant p53" or "p53 mutation" is meant p53 protein (or gene encoding said protein) incorporating a mutation that inhibits or eliminates its tumor suppressor function. In an embodiment, said p53 mutation is, Y126_splice, K132Q, M133K, R174fs, R175H, R196*, C238S, C242Y, G245S, R248W, R248Q, 1255T, D259V, S261_splice, R267P, R273C, R282W, A159V or R280K. In an embodiment, the foregoing cancer is non-small cell lung cancer (NSLCC), pancreatic cancer, head and neck cancer, gastric cancer, breast cancer, colon cancer or ovarian cancer.

Assay

The ability of compounds of the disclosure to inhibit MAT2A can be measured as described in Biological Example 1 below.

Pharmaceutical Composition

The compounds of Formula (A), Formula (I) or a subembodiment described herein, or a pharmaceutically acceptable salt thereof, may be in the form of compositions suitable for administration to a subject. In general, such compositions are pharmaceutical compositions comprising a compound of Formula (A), Formula (I) or a subembodiment described herein or a pharmaceutically acceptable salt thereof and one or more pharmaceutically acceptable or physiologically acceptable excipients. In certain embodiments, the compound of Formula (A), Formula (I) or a subembodiment described herein, or a pharmaceutically acceptable salt thereof is present in a therapeutically effective amount. The pharmaceutical compositions may be used in the methods disclosed herein; thus, for example, the pharmaceutical compositions can be administered ex vivo or in vivo to a subject in order to practice the therapeutic methods and uses described herein.

The pharmaceutical compositions can be formulated to be compatible with the intended method or route of administration; exemplary routes of administration are set forth herein. Furthermore, the pharmaceutical compositions may be used in combination with other therapeutically active agents or compounds as described herein in order to treat the diseases, disorders and conditions contemplated by the present disclosure.

The pharmaceutical compositions containing the active ingredient (e.g., a compound of Formula (A), Formula (I) or a subembodiment described herein, a pharmaceutically acceptable salt thereof) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets, capsules, and the like. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl di-stearate may be employed. The tablets may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinyl acetate, methylcellulose, carboxymethylcellulose, protamine sulfate, or lactide and glycolide copolymers, polylactide and glycolide copolymers, or ethylene vinyl acetate copolymers in order to control delivery of an administered composition. For example, the oral agent can be entrapped in microcapsules prepared by coacervation techniques or by interfacial polymerization, by the use of hydroxymethyl cellulose or gelatin-microcapsules or poly (methyl methacrylate) microcapsules, respectively, or in a colloid drug delivery system. Colloidal dispersion systems include macromolecule complexes, nanocapsules, microspheres, microbeads, and lipid-based systems, including oil-in-water emulsions, micelles, mixed micelles, and liposomes. Methods for the preparation of the above-mentioned formulations are known in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, (hydroxypropyl)methyl cellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., poly-oxyethylene stearate), or condensation products of ethylene oxide with long chain aliphatic alcohols (e.g., for heptdecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of a compound of Formula (A), Formula (I) or a subembodiment described herein, or a salt thereof, and one or more pharmaceutically acceptable excipient. Suitable pharmaceutically acceptable excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. Any drug delivery apparatus may be used to deliver a compound of Formula (A), Formula (I) or a subembodiment described herein, or a salt thereof, including implants (e.g., implantable pumps) and catheter systems, slow injection pumps and devices, all of which are well known to the skilled artisan.

Depot injections, which are generally administered subcutaneously or intramuscularly, may also be utilized to release the compound of Formula (A), Formula (I) or a subembodiment described herein, or a salt thereof over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. The suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, NJ) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose, any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

A compound of Formula (A), Formula (I) or a subembodiment described herein, or a salt thereof may also be administered in the form of suppositories for rectal administration or sprays for nasal or inhalation use. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

Routes of Administration

Compounds of Formula (A), Formula (I) or a subembodiment described herein, or a salt thereof and compositions containing the same may be administered in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to administer the compounds of Formula (A), Formula (I) or a subembodiment described herein, or a salt thereof over a defined period of time. Particular embodiments of the present invention contemplate oral administration.

Combination Therapy

The present invention contemplates the use of compounds of Formula (A), Formula (I) or a subembodiment described herein, or a salt thereof in combination with one or more active therapeutic agents (e.g., chemotherapeutic agents) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the compounds of Formula (A), Formula (I) or a subembodiment described herein, or a salt thereof are administered or applied sequentially, e.g., where one agent is administered prior to one or more other agents. In other embodiments, the compounds of Formula (A), Formula (I) or a subembodiment described herein, or a salt thereof are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present disclosure.

The compounds of Formula (A), Formula (I) or a subembodiment described herein, or a salt thereof may be used in combination with at least one other (active) agent in any manner appropriate under the circumstances. In one embodiment, treatment with the at least one active agent and at least one compound of Formula (A), Formula (I) or a subembodiment described herein, or a salt thereof is maintained over a period of time. In another embodiment, treatment with the at least one active agent is reduced or discontinued (e.g., when the subject is stable), while treatment with the compound of Formula (A), Formula (I) or a subembodiment described herein, or a salt thereof is maintained at a constant dosing regimen. In a further embodiment, treatment with the at least one active agent is reduced or discontinued (e.g., when the subject is stable), while treatment with a compound of Formula (A), Formula (I) or a subembodiment described herein, or a salt thereof is reduced (e.g., lower dose, less frequent dosing or shorter treatment regimen). In yet another embodiment, treatment with the at least one active agent is reduced or discontinued (e.g., when the subject is stable), and treatment with the compound of Formula (A), Formula (I) or a subembodiment described herein, or a salt thereof is increased (e.g., higher dose, more frequent dosing or longer treatment regimen). In yet another embodiment, treatment with the at least one active agent is maintained and treatment with the compound of Formula (A), Formula (I) or a subembodiment described herein, or a salt thereof is reduced or discontinued (e.g., lower dose, less frequent dosing or shorter treatment regimen). In yet another embodiment, treatment with the at least one active agent and treatment with the compound of Formula (A), Formula (I) or a subembodiment described herein, or a salt thereof are reduced or discontinued (e.g., lower dose, less frequent dosing or shorter treatment regimen).

The present disclosure provides methods for treating cancer with a compound of Formula (A), Formula (I) or a subembodiment described herein, or a salt thereof and at least one additional therapeutic or diagnostic agent.

In some embodiments, the compound of Formula (A), Formula (I) or a subembodiment described herein, or a salt thereof is administered in combination with at least one additional therapeutic agent, selected from Temozolomide, Pemetrexed, Pegylated liposomal doxorubicin (Doxil), Eribulin (Halaven), Ixabepilone (Ixempra), Protein-bound paclitaxel (Abraxane), Oxaliplatin, Irinotecan, Venatoclax (bcl2 inhibitor), 5-azacytadine, Anti-CD20 therapeutics, such as Rituxan and obinutuzumab, Hormonal agents (anastrozole, exemestand, letrozole, zoladex, lupon eligard), CDK4/6 inhibitors, Palbociclib, Abemaciclib, CPI (Avelumab, Cemiplimab-rwlc, and Bevacizumab.

In certain embodiments, the present disclosure provides methods for treating cancer comprising administration of a compound of Formula (A), Formula (I) or a subembodiment described herein, or a salt thereof in combination with a signal transduction inhibitor (STI) to achieve additive or synergistic suppression of tumor growth. As used herein, the term "signal transduction inhibitor" refers to an agent that selectively inhibits one or more steps in a signaling pathway. Examples of signal transduction inhibitors (STIs) useful in methods described herein include, but are not limited to: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in immunomodulation can also be used in combination with one or more compounds of Formula (A), Formula (I) or a subembodiment described herein, or a salt thereof for the suppression of tumor growth in cancer patients.

In certain embodiments, the present disclosure provides methods for treating cancer comprising administration of a compound of Formula (A), Formula (I) or a subembodiment described herein, or a salt thereof in combination with a chemotherapeutic agents. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above. In a particular embodiment, compounds of the present disclosure are coadministered with a cytostatic compound selected from the group consisting of cisplatin, doxorubicin, taxol, taxotere and mitomycin C, In a particular embodiment, the cytostatic compound is doxorubicin.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, enzalutamide, apalutamide, abiraterone acetate, leuprolide, and goserelin; and pharmaceutically acceptable salts, acids or derivatives of any of the above. In certain embodiments, combination therapy comprises administration of a hormone or related hormonal agent.

The present disclosure also contemplates the use of the compounds of Formula (A), Formula (I) or a subembodiment described herein, or a salt thereof in combination with immune checkpoint inhibitors. The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints).

Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism. Examples of immune checkpoint inhibitors include but are not limited to CTLA-4, PD-1, PD-L1, BTLA, TIM3, LAG3, OX40, 41BB, VISTA, CD96, TGFβ, CD73, CD39, A2AR, A2BR, IDO1, TDO2, Arginase, B7-H3, B7-H4. Cell-based modulators of anti-cancer immunity are also contemplated. Examples of such modulators include but are not limited to chimeric antigen receptor T-cells, tumor infiltrating T-cells and dendritic-cells.

The present disclosure contemplates the use of compounds of Formula (A), Formula (I) or a subembodiment described herein, or a salt thereof in combination with inhibitors of the aforementioned immune-checkpoint receptors and ligands, for example ipilimumab, abatacept, nivolumab, pembrolizumab, atezolizumab, nivolumab, and durvalumab.

Additional treatment modalities that may be used in combination with a compound of Formula (A), Formula (I) or a subembodiment described herein, or a salt thereof include radiotherapy, a monoclonal antibody against a tumor antigen, a complex of a monoclonal antibody and toxin, a T-cell adjuvant, bone marrow transplant, or antigen presenting cells (e.g., dendritic cell therapy).

The present disclosure contemplates the use of compounds of Formula (A), Formula (I) or a subembodiment described herein, or a salt thereof for the treatment of glioblastoma either alone or in combination with radiation and/or temozolomide (TMZ), avastin or lomustine.

The present disclosure encompasses pharmaceutically acceptable salts, acids or derivatives of any of the above.

Dosing

The compounds of Formula (A), Formula (I) or a subembodiment described herein, or a salt thereof may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or $ED_{50}$ of an agent is the dose or amount of an agent that produces a therapeutic response or desired effect in 50% of the population to which it is administered. Although the $ED_{50}$ is commonly used as a measure of reasonable expectance of an agent's effect, it is not necessarily the dose that a clinician might deem appropriate taking into consideration all relevant factors. Thus, in some situations the effective amount is more than the calculated $ED_{50}$, in other situations the effective amount is less than the calculated $ED_{50}$, and in still other situations the effective amount is the same as the calculated $ED_{50}$.

In addition, an effective dose of a compound of Formula (A), Formula (I) or a subembodiment described herein, or a salt thereof may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the compounds of Formula (A), Formula (I) or a subembodiment described herein, or a salt thereof may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the compound of Formula (A), Formula (I) or a subembodiment described herein, or a salt thereof is contained in a "unit dosage form". The phrase "unit dosage form" refers to physically discrete units, each unit containing a predetermined amount of the compound of Formula (A), Formula (I) or a subembodiment described herein, or a salt thereof, either alone or in combination with one or more additional agents, sufficient to produce the desired effect. It will be appreciated that the parameters of a unit dosage form will depend on the particular agent and the effect to be achieved.

Kits

The present invention also contemplates kits comprising a compound of Formula (A), Formula (I) or a subembodiment described herein, or a salt thereof, and pharmaceutical compositions thereof. The kits are generally in the form of a physical structure housing various components, as described below, and may be utilized, for example, in practicing the methods described above.

A kit can include one or more of the compound of Formula (A), Formula (I) or a subembodiment described herein, or a salt thereof (provided in, e.g., a sterile container), which may be in the form of a pharmaceutical composition suitable for administration to a subject. The compound of Formula (A), Formula (I) or a subembodiment described herein, or a salt thereof can be provided in a form that is ready for use (e.g., a tablet or capsule) or in a form requiring, for example, reconstitution or dilution (e.g., a powder) prior to administration. When the compounds of Formula (A), Formula (I) or a subembodiment described herein, or a salt thereof are in a form that needs to be reconstituted or diluted by a user, the kit may also include diluents (e.g., sterile water), buffers, pharmaceutically acceptable excipients, and the like, packaged with or separately from the compounds of Formula (A), Formula (I) or a subembodiment described herein, for a salt thereof. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

Particular Embodiments of the Present Disclosure

Embodiment 1. A compound having the Formula (A)

(A)

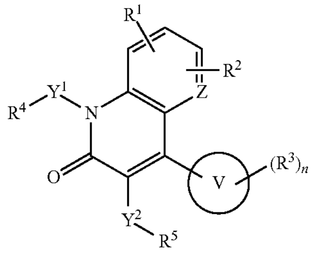

or a pharmaceutically acceptable salt thereof, wherein

Z is selected from the group consisting of CH and N;

$R^1$ and $R^2$ are each independently selected from the group consisting of H, $C_{1-6}$ alkyl, $C_{1-6}$ haloalkyl, $C_{1-6}$ alkoxy, $C_{1-6}$ haloalkoxy, cyano, halo and $C_{3-8}$ cycloalkyl, wherein the cycloalkyl group is substituted with from 0 to 2 groups independently selected from the group consisting of $C_{1-4}$ alkyl and halo;

ring V is a phenyl or a 5- to 6-membered heteroaryl comprising 1 to 3 heteroatom ring vertices independently selected from the group consisting of N, O, and S;

each $R^3$ is independently selected from the group consisting of halo, $C_{1-4}$ alkyl, $C_{1-4}$ haloalkyl, —$OR^z$, and —$X^4$—$OR^z$, wherein each $R^z$ is selected from the group consisting of H, $C_{1-4}$ alkyl, and $C_{1-4}$ haloalkyl, and each $X^4$ is $C_{1-3}$ alkylene;

the subscript n is 0, 1 or 2;

$Y^1$ is selected from the group consisting of a bond and $C_{1-4}$ alkylene;

$R^4$ is selected from the group consisting of H, halo, $C_{1-6}$ alkyl, $C_{1-6}$ haloalkyl, $C_{6-10}$ aryl, —$NR^aR^b$, —$C(O)R^d$, —$C(O)OR^d$, —$C(O)NR^aR^b$, and a 6- to 10-membered heteroaryl ring having 1 to 3 heteroatom ring vertices independently selected from the group consisting of N, O, and S; wherein $R^a$ and $R^b$ are each independently selected from the group consisting of H, $C_{1-6}$ alkyl, $C_{1-6}$ haloalkyl, and phenyl; wherein the phenyl is substituted with 0 to 2 moieties independently selected from the group consisting of $C_{1-4}$ alkyl, —$OR^x$, and —$X^2$—$OR^x$, and wherein each $R^x$ is selected from the group consisting of H, $C_{1-4}$ alkyl, and $C_{1-4}$ haloalkyl, and each $X^2$ is $C_{1-3}$ alkylene;

$R^d$ is selected from the group consisting of H, $C_{1-6}$ alkyl, and $C_{1-6}$ haloalkyl;

$Y^2$ is selected from the group consisting of a bond and $C_{1-4}$ alkylene;

$R^5$ is selected from the group consisting of H, halo, cyano, $C_{1-6}$ alkyl, $C_{1-6}$ haloalkyl, —$OR^c$, —O—$X^1$—$R^c$, —$SR^c$, —S—$X^1$—$R^c$, —$NR^fR^g$, —$S(O)_2R^c$, —$S(O)_2$—$X^1$—$R^c$, —$S(O)_2$—$NR^h$—$R^c$, —$S(O)_2$—$NR^h$—$X^1$—$R^c$, —$NR^h$—$S(O)_2$—$R^c$, —$NR^h$—$S(O)_2$—$X^1$—$R^c$, and a 3- to 6-membered heterocycloalkyl having 1 to 3 heteroatom ring vertices independently selected from the group consisting of N, O, and S;

$X^1$ is selected from the group consisting of a bond and $C_{1-4}$ alkylene;

$R^c$ is selected from the group consisting of H, $C_{1-6}$ alkyl, $C_{1-6}$ haloalkyl, $C_{3-8}$ cycloalkyl, $C_{6-10}$ aryl, a 3- to 6-membered heterocycloalkyl having 1 to 3 heteroatom ring vertices independently selected from N, O, and S, and a 5- to 10-membered heteroaryl having 1 to 4 heteroatom ring vertices independently selected from the group consisting of N, O, and S, wherein the $C_{3-8}$ cycloalkyl, the $C_{6-10}$ aryl, the 3- to 6-membered heterocycloalkyl, and the 5- to 10-membered heteroaryl are substituted with 0 to 2 moieties independently selected from the group consisting of $C_{1-4}$ alkyl, —$OR^y$, —$X^3$—$OR^y$, —$C(O)R^y$, —$X^3$—$C(O)R^y$, —$C(O)OR^y$, and —$X^3$—$C(O)OR^y$, wherein each $R^y$ is selected from the group consisting of H, $C_{1-6}$ alkyl, and $C_{1-6}$ haloalkyl, and each $X^3$ is $C_{1-3}$ alkylene;

$R^f$ and $R^g$ are each independently selected from the group consisting of H, $C_{1-6}$ alkyl, $C_{1-6}$ haloalkyl, and phenyl; or $R^f$ and $R^g$ together with the nitrogen to which they are attached combine to form a 4- to 6-membered heterocycloalkyl ring comprising 0 to 2 additional heteroatoms independently selected from the group consisting of N, O, and S, wherein the phenyl and the 4- to 6-membered heterocycloalkyl are substituted with 0 to 2 moieties independently selected from the group consisting of $C_{1-4}$ alkyl, —$OR^x$, and —$X^2$—$OR^x$, wherein each $R^x$ is selected from the group consisting of H, $C_{1-4}$ alkyl, and $C_{1-4}$ haloalkyl, and each $X^2$ is $C_{1-3}$ alkylene;

$R^h$ is selected from the group consisting of H, $C_{1-6}$ alkyl and $C_{1-6}$ haloalkyl;

provided that the compound of Formula (I) is other than a compound selected from the group consisting of -continued

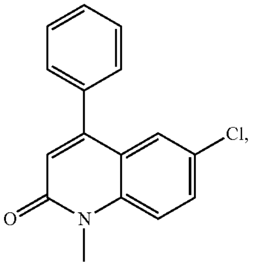

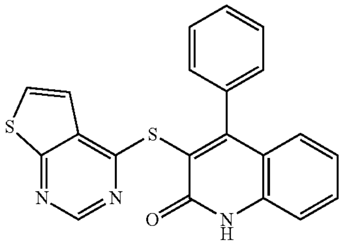

,

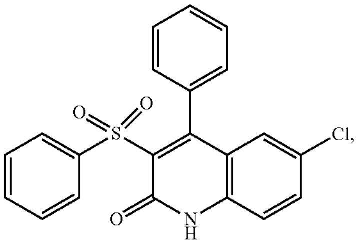

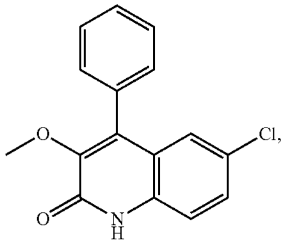

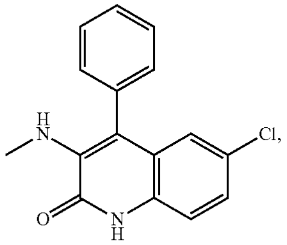

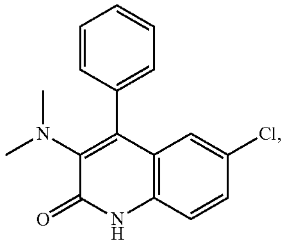

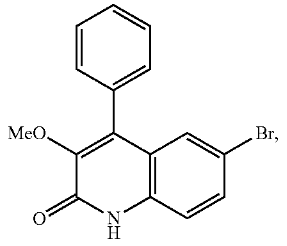

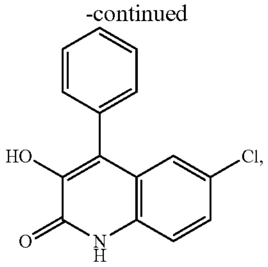

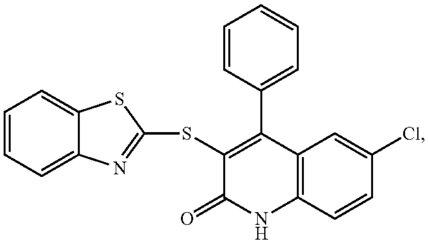

and

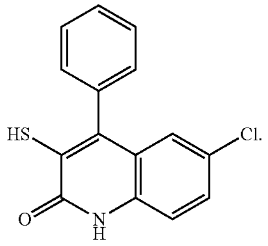

Embodiment 2. A compound having the Formula (I)

(I)

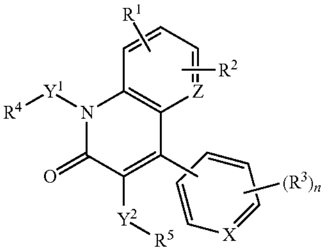

or a pharmaceutically acceptable salt thereof, wherein

Z is selected from the group consisting of CH and N;

$R^1$ and $R^2$ are each independently selected from the group consisting of H, $C_{1-6}$ alkyl, $C_{1-6}$ haloalkyl, $C_{1-6}$ alkoxy, cyano, halo and $C_{3-8}$ cycloalkyl, wherein the cycloalkyl group is substituted with from 0 to 2 groups independently selected from the group consisting of $C_{1-4}$ alkyl and halo;

X is CH, $CR^3$, or N;

each $R^3$ is independently selected from the group consisting of halo, $C_{1-4}$ alkyl, $C_{1-4}$ haloalkyl, —$OR^z$, and —$X^4$—$OR^z$, wherein each $R^z$ is selected from the group consisting of H, $C_{1-4}$ alkyl, and $C_{1-4}$ haloalkyl, and each $X^4$ is $C_{1-3}$ alkylene;

the subscript n is 0, 1 or 2;

$Y^1$ is selected from the group consisting of a bond and $C_{1-4}$ alkylene;

$R^4$ is selected from the group consisting of H, halo, $C_{1-6}$ alkyl, $C_{1-6}$ haloalkyl, $C_{6-10}$ aryl, —$NR^aR^b$, —$C(O)R^d$, —$C(O)OR^d$, —$C(O)NR^aR^b$, and a 6- to 10-membered heteroaryl ring having 1 to 3 heteroatom ring vertices independently selected from the group consisting of N, O, and S; wherein $R^a$ and $R^b$ are each independently selected from the group consisting of H, $C_{1-6}$ alkyl, $C_{1-6}$ haloalkyl, and phenyl; wherein the phenyl is substituted with 0 to 2 moieties independently selected from the group consisting of $C_{1-4}$ alkyl, —$OR^x$, and —$X^2$—$OR^x$, and wherein each $R^x$ is selected from the group consisting of H, $C_{1-4}$ alkyl, and $C_{1-4}$ haloalkyl, and each $X^2$ is $C_{1-3}$ alkylene;

$R^d$ is selected from the group consisting of H, $C_{1-6}$ alkyl, and $C_{1-6}$ haloalkyl;

$Y^2$ is selected from the group consisting of a bond and $C_{1-4}$ alkylene;

$R^5$ is selected from the group consisting of H, halo, cyano, $C_{1-6}$ alkyl, $C_{1-6}$ haloalkyl, —$OR^c$, —O—$X^1$—$R^c$, —$SR^c$, —S—$X^1$—$R^c$, —$NR^fR^g$, —$S(O)_2R^c$, —$S(O)_2$—$X^1$—$R^c$, —$S(O)_2$—$NR^h$—$R^c$, —$S(O)_2$—$NR^h$—$X^1$—$R^c$, —$NR^h$—$S(O)_2$—$R^c$, —$NR^h$—$S(O)_2$—$X^1$—$R^c$, and a 3- to 6-membered heterocycloalkyl having 1 to 3 heteroatom ring vertices independently selected from the group consisting of N, O, and S;

$X^1$ is selected from the group consisting of a bond and $C_{1-4}$ alkylene;

$R^c$ is selected from the group consisting of H, $C_{1-6}$ alkyl, $C_{1-6}$ haloalkyl, $C_{3-8}$ cycloalkyl, $C_{6-10}$ aryl, a 3- to 6-membered heterocycloalkyl having 1 to 3 heteroatom ring vertices independently selected from N, O, and S, and a 5- to 10-membered heteroaryl having 1 to 4 heteroatom ring vertices independently selected from the group consisting of N, O, and S, wherein the $C_{3-8}$ cycloalkyl, the $C_{6-10}$ aryl, the 3- to 6-membered heterocycloalkyl, and the 5- to 10-membered heteroaryl are substituted with 0 to 2 moieties independently selected from the group consisting of $C_{1-4}$ alkyl, —$OR^y$, —$X^3$—$OR^y$, —$C(O)R^y$, —$X^3$—$C(O)R^y$, —$C(O)OR^y$, and —$X^3$—$C(O)OR^y$, wherein each $R^y$ is selected from the group consisting of H, $C_{1-6}$ alkyl, and $C_{1-6}$ haloalkyl, and each $X^3$ is $C_{1-3}$ alkylene;

$R^f$ and $R^g$ are each independently selected from the group consisting of H, $C_{1-6}$ alkyl, $C_{1-6}$ haloalkyl, and phenyl; or $R^f$ and $R^g$ together with the nitrogen to which they are attached combine to form a 4- to 6-membered heterocycloalkyl ring comprising 0 to 2 additional heteroatoms independently selected from the group consisting of N, O, and S, wherein the phenyl and the 4- to 6-membered heterocycloalkyl are substituted with 0 to 2 moieties independently selected from the group consisting of $C_{1-4}$ alkyl, —$OR^x$, and —$X^2$—$OR^x$, wherein each $R^x$ is selected from the group consisting of H, $C_{1-4}$ alkyl, and $C_{1-4}$ haloalkyl, and each $X^2$ is $C_{1-3}$ alkylene;

$R^h$ is selected from the group consisting of H, $C_{1-6}$ alkyl and $C_{1-6}$ haloalkyl;

provided that the compound of Formula (I) is other than a compound selected from the group consisting of

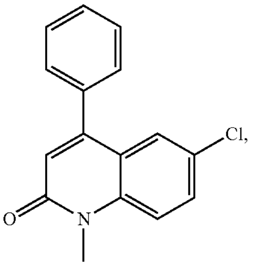

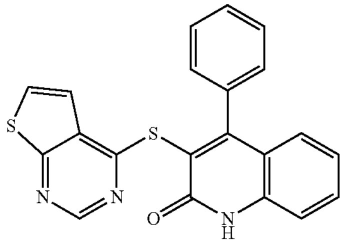
,

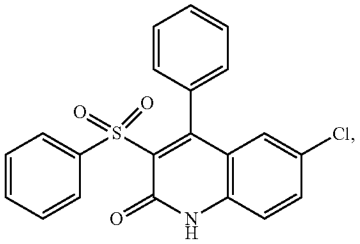

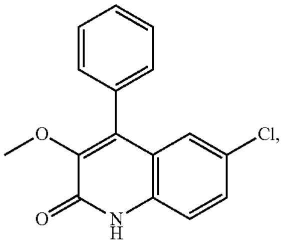

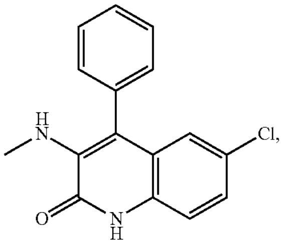

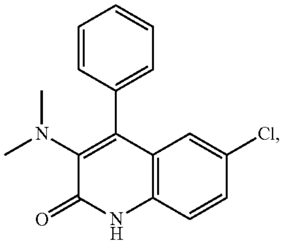

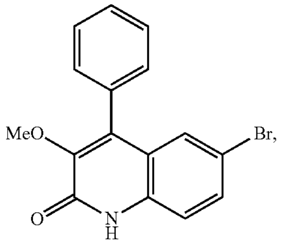

-continued

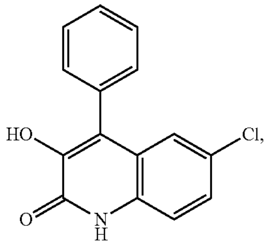

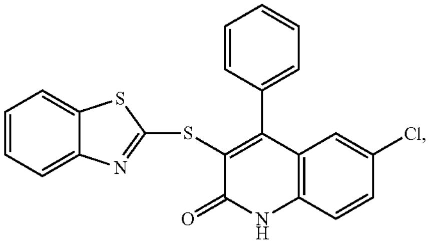

and

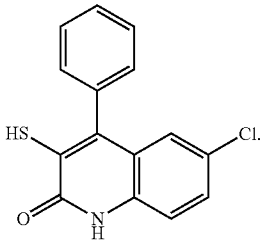

Embodiment 3. The compound of embodiment 1 or embodiment 2, having Formula (Ia)

(Ia)

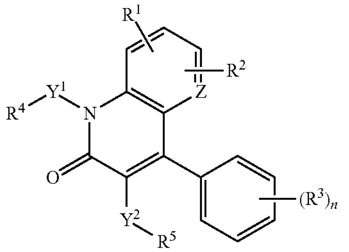

or a pharmaceutically acceptable salt thereof.

Embodiment 4. The compound of embodiment 1 or embodiment 2, having Formula (Ib)

(Ib)

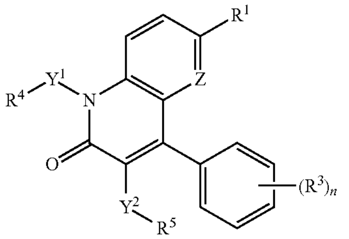

or a pharmaceutically acceptable salt thereof.

Embodiment 5. The compound of embodiment 1 or embodiment 2, having Formula (Ic)

(Ic)

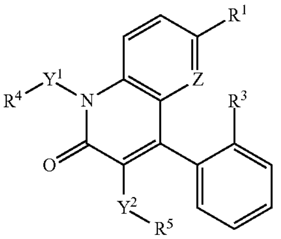

or a pharmaceutically acceptable salt thereof.

Embodiment 6. The compound of embodiment 1 or embodiment 2, having Formula (Id)

(Id)

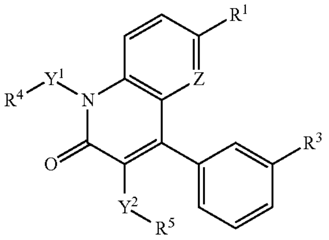

or a pharmaceutically acceptable salt thereof.

Embodiment 7. The compound of embodiment 1 or embodiment 2, having Formula (Ie)

(Ie)

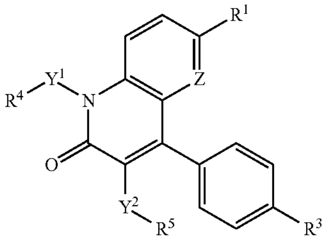

or a pharmaceutically acceptable salt thereof.

Embodiment 8. The compound of embodiment 1 or embodiment 2, having Formula (If)

(If)

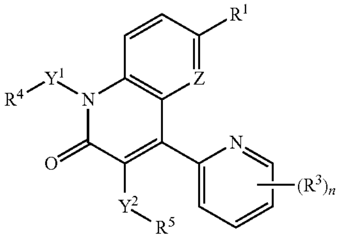

or a pharmaceutically acceptable salt thereof.

Embodiment 9. The compound of embodiment 1 or embodiment 2, having Formula (Ig)

(Ig)

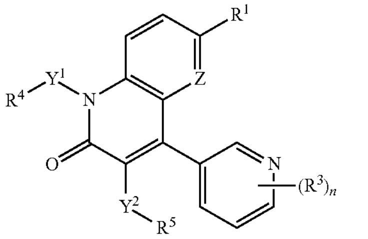

or a pharmaceutically acceptable salt thereof.

Embodiment 10. The compound of embodiment 1 or embodiment 2, having Formula (Ih)

(Ih)

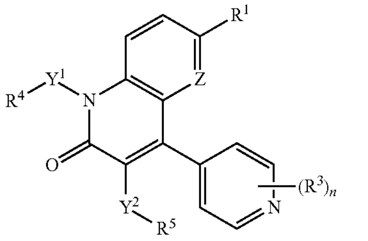

or a pharmaceutically acceptable salt thereof.

Embodiment 11. The compound of any one of embodiments 1 to 10, wherein Z is CH.

Embodiment 12. The compound of any one of embodiments 1 to 10, wherein Z is N.

Embodiment 13. The compound of any one of embodiments 1 to 12, wherein $R^1$ is selected from the group consisting of $C_{1-6}$ alkyl, $C_{1-6}$ haloalkyl, halo, and $C_{3-8}$ cycloalkyl, wherein the cycloalkyl group substituted with from 0 to 2 groups independently selected from the group consisting of $C_{1-4}$ alkyl and halo.

Embodiment 14. The compound of any one of embodiments 1 to 12, wherein $R^1$ is selected from the group consisting of $C_{1-2}$ alkyl, $C_{1-2}$ haloalkyl, and halo.

Embodiment 15. The compound of any one of embodiments 1 to 12, wherein $R^1$ is selected from the group consisting of methyl, trifluoromethyl, chloro, bromo, fluoro, and cyclopropyl.

Embodiment 16. The compound of any one of embodiments 1 to 12, wherein $R^1$ is methyl.

Embodiment 17. The compound of any one of embodiments 1 to 12, wherein $R^1$ is trifluoromethyl.

Embodiment 18. The compound of any one of embodiments 1 to 12, wherein $R^1$ is chloro.

Embodiment 19. The compound of any one of embodiments 1 to 12, wherein $R^1$ is fluoro.

Embodiment 20. The compound of any one of embodiments 1 to 12, wherein $R^1$ is bromo.

Embodiment 21. The compound of any one of embodiments 1 to 12, wherein $R^1$ is cyclopropyl.

Embodiment 22. The compound of any one of embodiments 1, 3, or 11 to 21, wherein $R^2$ is selected from the group consisting of H, $C_{1-2}$ alkyl, halo, and $C_{1-2}$ alkoxy.

Embodiment 23. The compound of any one of embodiments 1, 3, or 11 to 21, wherein $R^2$ is selected from the group consisting of H and methoxy.

Embodiment 24. The compound of any one of embodiments 1, 3, or 11 to 21, wherein $R^2$ is H.

Embodiment 25. The compound of any one of embodiments 1, 3, or 11 to 21, wherein $R^2$ is methoxy.

Embodiment 26. The compound of any one of embodiments 1 to 25, wherein each $R^3$ is independently selected from the group consisting of halo, $C_{1-4}$ alkyl, $C_{1-4}$ haloalkyl.

Embodiment 27. The compound of any one of embodiments 1 to 25, wherein each $R^3$ is independently selected from the group consisting of $—OR^z$, and $—X^4—OR^z$.

Embodiment 28. The compound of embodiment 27, wherein $R^z$ is H.

Embodiment 29. The compound of embodiment 27, wherein $R^z$ is $C_{1-4}$ alkyl.

Embodiment 30. The compound of any one of embodiments 1 to 25, wherein each $R^3$ is independently selected from the group consisting of chloro, bromo, and methyl.

Embodiment 31. The compound of any one of embodiments 1 to 25, wherein each $R^3$ is chloro.

Embodiment 32. The compound of any one of embodiments 1 to 25, wherein each $R^3$ is bromo.

Embodiment 33. The compound of any one of embodiments 1 to 25, wherein each $R^3$ is methyl.

Embodiment 34. The compound of any one of embodiments 1 to 4 or 8 to 33, wherein the subscript n is 1.

Embodiment 35. The compound of any one of embodiments 1 to 4 or 8 to 25, wherein the subscript n is 0.

Embodiment 36. The compound of any one of embodiments 1 to 35, wherein $Y^1$ is a bond.

Embodiment 37. The compound of any one of embodiments 1 to 35, wherein $Y^1$ is $C_{1-4}$ alkylene.

Embodiment 38. The compound of any one of embodiments 1 to 35, wherein $Y^1$ is methylene.

Embodiment 39. The compound of any one of embodiments 1 to 38, wherein $R^4$ is selected from the group consisting of H, $C_{1-6}$ alkyl, $C_{1-6}$ haloalkyl, $C_{6-10}$ aryl, $—NR^aR^b$, $—C(O)NR^aR^b$, and a 6- to 10-membered heteroaryl ring having 1 to 3 heteroatom ring vertices independently selected from the group consisting of N, O, and S.

Embodiment 40. The compound of any one of embodiments 1 to 38, wherein $R^4$ is H.

Embodiment 41. The compound of any one of embodiments 1 to 38, wherein $R^4$ is selected from the group consisting of $C_{1-6}$ alkyl, $C_{1-6}$ haloalkyl, and phenyl.

Embodiment 42. The compound of any one of embodiments 1 to 38, wherein $R^4$ is a 6- to 10-membered heteroaryl ring having 1 to 3 heteroatom ring vertices independently selected from the group consisting of N, O, and S.

Embodiment 43. The compound of embodiment 42, wherein $R^4$ is pyrrole, pyrazole, imidazolyl, triazole, pyridinyl, pyrimidinyl, pyridazinyl, and pyrazinyl.

Embodiment 44. The compound of embodiment 42, wherein $R^4$ is selected from the group consisting of pyridinyl and imidazolyl.

Embodiment 45. The compound of any one of embodiments 1 to 38, wherein $R^4$ is selected from the group consisting of $—NR^aR^b$ and $—C(O)NR^aR^b$.

Embodiment 46. The compound of embodiment 45, wherein $R^a$ and $R^b$ are each independently selected from the group consisting of H, methyl, phenyl, and toluenyl.

Embodiment 47. The compound of embodiment 45, wherein $R^a$ and $R^b$ are each H.

Embodiment 48. The compound of embodiment 45, wherein $R^a$ and $R^b$ are each methyl.

Embodiment 49. The compound of embodiment 45, wherein $R^a$ is H; and $R^b$ is methyl.

Embodiment 50. The compound of embodiment 45, wherein $R^a$ is H; and $R^b$ is phenyl.

Embodiment The compound of embodiment 45, wherein $R^a$ is H; and $R^b$ is toluenyl.

Embodiment 52. The compound of any one of embodiments 1 to 51, wherein $Y^2$ is a bond.

Embodiment 53. The compound of any one of embodiments 1 to 51, wherein $Y^2$ is $C_{1-4}$ alkylene.

Embodiment 54. The compound of any one of embodiments 1 to 51, wherein $Y^2$ is methylene.

Embodiment 55. The compound of any one of embodiments 1 to 54, wherein $R^5$ is selected from the group consisting of H, halo, cyano, $C_{1-6}$ alkyl, and $C_{1-6}$ haloalkyl.

Embodiment 56. The compound of any one of embodiments 1 to 54, wherein $R^5$ is H.

Embodiment 57. The compound of any one of embodiments 1 to 54, wherein $R^5$ is selected from the group consisting of bromo, chloro, and iodo.

Embodiment 58. The compound of any one of embodiments 1 to 54, wherein $R^5$ is cyano.

Embodiment 59. The compound of any one of embodiments 1 to 54, wherein $R^5$ is $—NR^fR^g$.

Embodiment 60. The compound of embodiment 59, wherein $R^f$ and $R^g$ are each independently selected from the group consisting of H, $C_{1-6}$ alkyl, and $C_{1-6}$ haloalkyl.

Embodiment 61. The compound of any one of embodiments 1 to 54, wherein $R^5$ is a 3- to 6-membered heterocycloalkyl having 1 to 3 heteroatom ring vertices independently selected from the group consisting of N, O, and S.

Embodiment 62. The compound of embodiment 61, wherein the 3- to 6-membered heterocycloalkyl is selected from the group consisting of pyrrolidinyl piperidinyl, tetrahydrofuranyl, and tetrahydropyranyl, and morpholinyl.

Embodiment 63. The compound of embodiment 61, wherein the 3- to 6-membered heterocycloalkyl is morpholinyl.

Embodiment 64. The compound of any one of embodiments 1 to 54, wherein $R^5$ is selected from the group consisting of $—OR^c$, $—O—X^1—R^c$, $—SR^c$, $—S—X^1—R^c$, $—NR^fR^g$, $—S(O)_2R^c$, $—S(O)_2—X^1—R^e$, $—S(O)_2—NR^h—R^c$, and $—S(O)_2—NR^h—X^1—R^c$.

Embodiment 65. The compound of any one of embodiments 1 to 54, wherein $R^5$ is selected from the group consisting of $—OR^c$, $—O—X^1—R^c$, $—SR^c$, $—S—X^1—R^c$, $—S(O)_2R^c$, $—S(O)_2—X^1—R^c$, and $—S(O)_2—NH—R^c$.

Embodiment 66. The compound of any one of embodiments 1 to 54, wherein $R^5$ is selected from the group consisting of $—OR^c$ and $—O—X^1—R^c$.

Embodiment 67. The compound of any one of embodiments 1 to 54, wherein $R^5$ is selected from the group consisting of $—SR^c$, $—S—X^1—R^c$, and $—S(O)_2R^c$.

Embodiment 68. The compound of any one of embodiments 1 to 54, wherein $R^5$ is selected from the group consisting of $—S(O)_2R^c$, $—S(O)_2—X^1—R^c$, and $—S(O)_2—NH—R^c$.

Embodiment 69. The compound of any one of embodiments 1 to 54 or 64 to 68, wherein $R^c$ is selected from the group consisting of H, $C_{1-6}$ alkyl, $C_{1-6}$ haloalkyl, $C_{3-8}$ cycloalkyl, $C_{6-10}$ aryl, a 3- to 6-membered heterocycloalkyl having 1 to 3 heteroatom ring vertices independently selected from N, O, and S, and a 5- to 10-membered heteroaryl having 1 to 4 heteroatom ring vertices independently selected from the group consisting of N, O, and S.

Embodiment 70. The compound of any one of embodiments 1 to 54 or 64 to 68, wherein $R^c$ is H.

Embodiment 71. The compound of any one of embodiments 1 to 54 or 64 to 68, wherein $R^c$ is selected from the group consisting of $C_{1-6}$ alkyl and $C_{1-6}$ haloalkyl.

Embodiment 72. The compound of any one of embodiments 1 to 54 or 64 to 68, wherein $R^c$ is selected from the group consisting of $C_{3-6}$ cycloalkyl.

Embodiment 73. The compound of any one of embodiments 1 to 54 or 64 to 68, wherein $R^c$ is phenyl.

Embodiment 74. The compound of any one of embodiments 1 to 54 or 64 to 68, wherein $R^c$ is a 5- to 10-membered heteroaryl having 1 to 4 heteroatom ring vertices independently selected from the group consisting of N, O, and S.

Embodiment 75. The compound of embodiment 74, wherein the 5- to 10-membered heteroaryl is selected from the group consisting of thieno[3,2-d]pyrimidinyl, furo[3,2-d]pyrimidinyl, thio[3,2-b]pyridinyl furo[3,2-b]pyridinyl, benzo[b]thiophenyl, benzo benzothiazolyl, benzothiazolyl, pyrrole, pyrazole, imidazolyl, triazole, pyridinyl, pyrimidinyl, pyridazinyl, and pyrazinyl.

Embodiment 76. The compound of embodiment 74, wherein the 5- to 10-membered heteroaryl is selected from the group consisting of thieno[3,2-d]pyrimidinyl, benzothiazolyl, and triazole.

Embodiment 77. The compound of any one of embodiments 1 to 54 or 64 to 68, wherein $R^c$ is a 3- to 6-membered heterocycloalkyl having 1 to 3 heteroatom ring vertices independently selected from the group consisting of N, O, and S.

Embodiment 78. The compound of embodiment 77, wherein the 3- to 6-membered heterocycloalkyl is selected from the group consisting of pyrrolidinyl piperidinyl, tetrahydrofuranyl, and tetrahydropyranyl, and morpholinyl.

Embodiment 79. The compound of embodiment 77, wherein the 3- to 6-membered heterocycloalkyl is tetrahydrofuranyl.

Embodiment 80. The compound of embodiment 1, wherein the compound is selected from a compound in Table 1 or a pharmaceutically acceptable salt thereof.

Embodiment 81. A pharmaceutical composition comprising a compound of any one of embodiments 1 to 80, or a pharmaceutically acceptable salt thereof at least one pharmaceutically acceptable excipient Embodiment 82. A method for treating a disease mediated by MAT2A in a patient comprising administering to the patient a therapeutically effective amount of: any one of embodiments 1 to 80, or a compound Formula (I).

(I)

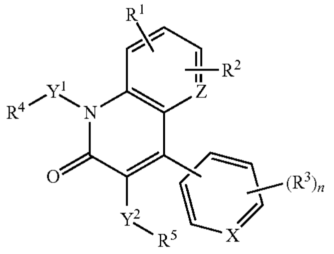

or a pharmaceutically acceptable salt thereof, wherein

Z is selected from the group consisting of CH and N;

$R^1$ and $R^2$ are each independently selected from the group consisting of H, $C_{1-6}$ alkyl, $C_{1-6}$ haloalkyl, $C_{1-6}$ alkoxy, cyano, halo and $C_{3-8}$ cycloalkyl, wherein the cycloalkyl group is substituted with from 0 to 2 groups independently selected from the group consisting of $C_{1-4}$ alkyl and halo;

X is CH, $CR^3$, or N;

each $R^3$ is independently selected from the group consisting of halo, $C_{1-4}$ alkyl, $C_{1-4}$ haloalkyl, —$OR^z$, and —$X^4$—$OR^z$, wherein each $R^z$ is selected from the group consisting of H, $C_{1-4}$ alkyl, and $C_{1-4}$ haloalkyl, and each $X^4$ is $C_{1-3}$ alkylene;

the subscript n is 0, 1 or 2;

$Y^1$ is selected from the group consisting of a bond and $C_{1-4}$ alkylene;

$R^4$ is selected from the group consisting of H, halo, $C_{1-6}$ alkyl, $C_{1-6}$ haloalkyl, $C_{6-10}$ aryl, —$NR^aR^b$, —$C(O)R^d$, —$C(O)OR^d$, —$C(O)NR^aR^b$, and a 6- to 10-membered heteroaryl ring having 1 to 3 heteroatom ring vertices independently selected from the group consisting of N, O, and S; wherein $R^a$ and $R^b$ are each independently selected from the group consisting of H, $C_{1-6}$ alkyl, $C_{1-6}$ haloalkyl, and phenyl; wherein the phenyl is substituted with 0 to 2 moieties independently selected from the group consisting of $C_{1-4}$ alkyl, —$OR^x$, and —$X^2$—$OR^x$, and wherein each $R^x$ is selected from the group consisting of H, $C_{1-4}$ alkyl, and $C_{1-4}$ haloalkyl, and each $X^2$ is $C_{1-3}$ alkylene;

$R^d$ is selected from the group consisting of H, $C_{1-6}$ alkyl, and $C_{1-6}$ haloalkyl;

$Y^2$ is selected from the group consisting of a bond and $C_{1-4}$ alkylene;

$R^5$ is selected from the group consisting of H, halo, cyano, $C_{1-6}$ alkyl; $C_{1-6}$ haloalkyl, —$OR^c$, —O—$X^1$—$R^c$, —$SR^c$, —S—$X^1$—$R^c$, —$NR^fR^g$, —$S(O)_2R^c$, —$S(O)_2$—$X^1$—$R^c$, —$S(O)_2$—$NR^h$—$R^c$, —$S(O)_2$—$NR^h$—$X^1$—$R^c$, —$NR^h$—$S(O)_2$—$R^c$, —$NR^h$—$S(O)_2$—$X^1$—$R^c$, and a 3- to 6-membered heterocycloalkyl having 1 to 3 heteroatom ring vertices independently selected from the group consisting of N, O, and S;

$X^1$ is selected from the group consisting of a bond and $C_{1-4}$ alkylene;

$R^c$ is selected from the group consisting of H, $C_{1-6}$ alkyl, $C_{1-6}$ haloalkyl, $C_{3-8}$ cycloalkyl, $C_{6-10}$ aryl, a 3- to 6-membered heterocycloalkyl having 1 to 3 heteroatom ring vertices independently selected from N, O, and S, and a 5- to 10-membered heteroaryl having 1 to 4 heteroatom ring vertices independently selected from the group consisting of N, O, and S, wherein the $C_{3-8}$ cycloalkyl, the $C_{6\_}o$ aryl, the 3- to 6-membered heterocycloalkyl, and the 5- to 10-membered heteroaryl are substituted with 0 to 2 moieties independently selected from the group consisting of $C_{1-4}$ alkyl, —$OR^y$, —$X^3$—$OR^y$, —$C(O)R^y$, —$X^3$—$C(O)R^y$, —$C(O)OR^y$, and —$X^3$—$C(O)OR^y$, wherein each $R^y$ is selected from the group consisting of H, $C_{1-6}$ alkyl, and $C_{1-6}$ haloalkyl, and each $X^3$ is $C_{1-3}$ alkylene;

$R^f$ and $R^g$ are each independently selected from the group consisting of H, $C_{1-6}$ alkyl, $C_{1-6}$ haloalkyl, and phenyl; or $R^f$ and $R^g$ together with the nitrogen to which they are attached combine to form a 4- to 6-membered heterocycloalkyl ring comprising 0 to 2 additional heteroatoms independently selected from the group consisting of N, O, and S, wherein the phenyl and the 4- to 6-membered heterocycloalkyl are substituted with 0 to 2 moieties independently selected from the group consisting of $C_{1-4}$ alkyl, —$OR^x$, and —$X^2$—$OR^x$, wherein each $R^x$ is selected from the group consisting of H, $C_{1-4}$ alkyl, and $C_{1-4}$ haloalkyl, and each $X^2$ is $C_{1-3}$ alkylene;

$R^h$ is selected from the group consisting of H, $C_{1-6}$ alkyl, $C_{1-6}$ haloalkyl.

Embodiment 83. The method of embodiment 82, wherein the disease is cancer.

Embodiment 84. A method of treating a MTAP null cancer in a patient comprising administering to the patient a therapeutically effective amount of a compound of any one of embodiments 1 to 80; or a compound Formula (A).

(A)

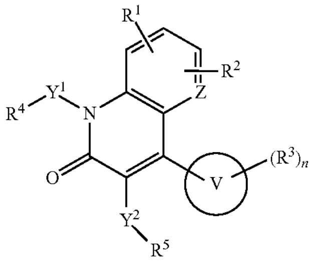

or a pharmaceutically acceptable salt thereof, optionally in a pharmaceutical composition, wherein Z is selected from the group consisting of CH and N;

$R^1$ and $R^2$ are each independently selected from the group consisting of H, $C_{1-6}$ alkyl, $C_{1-6}$ haloalkyl, $C_{1-6}$ alkoxy, cyano, halo and $C_{3-8}$ cycloalkyl, wherein the cycloalkyl group is substituted with from 0 to 2 groups independently selected from the group consisting of $C_{1-4}$ alkyl and halo;

ring V is a phenyl or a 5- to 6-membered heteroaryl comprising 1 to 3 heteroatom ring vertices independently selected from the group consisting of N, O, and S;

each $R^3$ is independently selected from the group consisting of halo, $C_{1-4}$ alkyl, $C_{1-4}$ haloalkyl, —$OR^z$, and —$X^4$—$OR^z$, wherein each $R^z$ is selected from the group consisting of H, $C_{1-4}$ alkyl, and $C_{1-4}$ haloalkyl, and each $X^4$ is $C_{1-3}$ alkylene;

the subscript n is 0, 1 or 2;

$Y^1$ is selected from the group consisting of a bond and $C_{1-4}$ alkylene;

$R^4$ is selected from the group consisting of H, halo, $C_{1-6}$ alkyl, $C_{1-6}$ haloalkyl, $C_{6-10}$ aryl, —$NR^aR^b$, —$C(O)R^d$, —$C(O)OR^d$, —$C(O)NR^aR^b$, and a 6- to 10-membered heteroaryl ring having 1 to 3 heteroatom ring vertices independently selected from the group consisting of N, O, and S; wherein $R^a$ and $R^b$ are each independently selected from the group consisting of H, $C_{1-6}$ alkyl, $C_{1-6}$ haloalkyl, and phenyl; wherein the phenyl is substituted with 0 to 2 moieties independently selected from the group consisting of $C_{1-4}$ alkyl, —$OR^x$, and —$X^2$—$OR^x$, and wherein each $R^x$ is selected from the group consisting of H, $C_{1-4}$ alkyl, and $C_{1-4}$ haloalkyl, and each $X^2$ is $C_{1-3}$ alkylene;

$R^d$ is selected from the group consisting of H, $C_{1-6}$ alkyl, and $C_{1-6}$ haloalkyl;

$Y^2$ is selected from the group consisting of a bond and $C_{1-4}$ alkylene;

$R^5$ is selected from the group consisting of H, halo, cyano, $C_{1-6}$ alkyl; $C_{1-6}$ haloalkyl, —$OR^c$, —O—$X^1$—$R^c$, —$SR^c$, —S—$X^1$—$R^c$, —$NR^fR^g$, —$S(O)_2R^c$, —$S(O)_2$—$X^1$—$R^c$, —$S(O)_2$—$NR^h$—$R^c$, —$S(O)_2$—$NR^h$—$X^1$—$R^c$, —$NR^h$—$S(O)_2$—$R^c$, —$NR^h$—$S(O)_2$—$X^1$—$R^c$, and a 3- to 6-membered heterocycloalkyl having 1 to 3 heteroatom ring vertices independently selected from the group consisting of N, O, and S;

$X^1$ is selected from the group consisting of a bond and $C_{1-4}$ alkylene;

$R^c$ is selected from the group consisting of H, $C_{1-6}$ alkyl, $C_{1-6}$ haloalkyl, $C_{3-8}$ cycloalkyl, $C_{6-10}$ aryl, a 3- to 6-membered heterocycloalkyl having 1 to 3 heteroatom ring vertices independently selected from N, O, and S, and a 5- to 10-membered heteroaryl having 1 to 4 heteroatom ring vertices independently selected from the group consisting of N, O, and S, wherein the $C_{3-8}$ cycloalkyl, the $C_{6-10}$ aryl, the 3- to 6-membered heterocycloalkyl, and the 5- to 10-membered heteroaryl are substituted with 0 to 2 moieties independently selected from the group consisting of $C_{1-4}$ alkyl, —$OR^y$, —$X^3$—$OR^y$, —$C(O)R^y$, —$X^3$—$C(O)R^y$, —$C(O)OR^y$, and —$X^3$—$C(O)OR^y$, wherein each $R^y$ is selected from the group consisting of H, $C_{1-6}$ alkyl, and $C_{1-6}$ haloalkyl, and each $X^3$ is $C_{1-3}$ alkylene;

$R^f$ and $R^g$ are each independently selected from the group consisting of H, $C_{1-6}$ alkyl, $C_{1-6}$ haloalkyl, and phenyl; or $R^f$ and $R^g$ together with the nitrogen to which they are attached combine to form a 4- to 6-membered heterocycloalkyl ring comprising 0 to 2 additional heteroatoms independently selected from the group consisting of N, O, and S, wherein the phenyl and the 4- to 6-membered heterocycloalkyl are substituted with 0 to 2 moieties independently selected from the group consisting of $C_{1-4}$ alkyl, —$OR^x$, and —$X^2$—$OR^x$, wherein each $R^x$ is selected from the group consisting of H, $C_{1-4}$ alkyl, and $C_{1-4}$ haloalkyl, and each $X^2$ is $C_{1-3}$ alkylene;

$R^h$ is selected from the group consisting of H, $C_{1-6}$ alkyl, $C_{1-6}$ haloalkyl.

Embodiment 85. A method for treating a cancer in a patient, wherein the cancer is characterized by a reduction or absence of MTAP gene expression, the absence of the MTAP gene, reduced level of MTAP protein, or reduced function of MTAP protein, comprising administering to the subject a therapeutically effective amount of a compound of any one of embodiments 1 to 80, or a compound Formula (A).

(A)

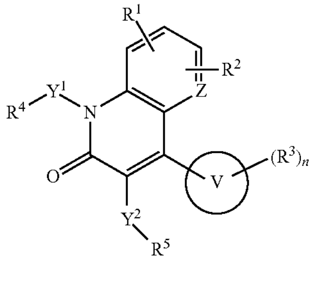

or a pharmaceutically acceptable salt thereof, optionally in a pharmaceutical composition, wherein Z is selected from the group consisting of CH and N;

$R^1$ and $R^2$ are each independently selected from the group consisting of H, $C_{1-6}$ alkyl, $C_{1-6}$ haloalkyl, $C_{1-6}$ alkoxy, cyano, halo and $C_{3-8}$ cycloalkyl, wherein the cycloalkyl group is substituted with from 0 to 2 groups independently selected from the group consisting of $C_{1-4}$ alkyl and halo;

ring V is a phenyl or a 5- to 6-membered heteroaryl comprising 1 to 3 heteroatom ring vertices independently selected from the group consisting of N, O, and S; each $R^3$ is independently selected from the group consisting of halo, $C_{1-4}$ alkyl, $C_{1-4}$ haloalkyl, —$OR^z$, and —$X^4$—$OR^z$, wherein each $R^z$ is selected from the group consisting of H, $C_{1-4}$ alkyl, and $C_{1-4}$ haloalkyl, and each $X^4$ is $C_{1-3}$ alkylene;

the subscript n is 0, 1 or 2;

$Y^1$ is selected from the group consisting of a bond and $C_{1-4}$ alkylene;

$R^4$ is selected from the group consisting of H, halo, $C_{1-6}$ alkyl, $C_{1-6}$ haloalkyl, $C_{6-10}$ aryl, —$NR^aR^b$, —$C(O)R^d$, —$C(O)OR^d$, —$C(O)NR^aR^b$, and a 6- to 10-membered heteroaryl ring having 1 to 3 heteroatom ring vertices independently selected from the group consisting of N, O, and S; wherein $R^a$ and $R^b$ are each independently selected from the group consisting of H, $C_{1-6}$ alkyl, $C_{1-6}$ haloalkyl, and phenyl; wherein the phenyl is substituted with 0 to 2 moieties independently selected from the group consisting of $C_{1-4}$ alkyl, —$OR^x$, and —$X^2$—$OR^x$, and wherein each $R^x$ is selected from the group consisting of H, $C_{1-4}$ alkyl, and $C_{1-4}$ haloalkyl, and each $X^2$ is $C_{1-3}$ alkylene;

$R^d$ is selected from the group consisting of H, $C_{1-6}$ alkyl, and $C_{1-6}$ haloalkyl;

$Y^2$ is selected from the group consisting of a bond and $C_{1-4}$ alkylene;

$R^5$ is selected from the group consisting of H, halo, cyano, $C_{1-6}$ alkyl; $C_{1-6}$ haloalkyl, —$OR^c$, —O—$X^1$—$R^c$, —$SR^c$, —S—$X^1$—$R^c$, —$NR^fR^g$, —$S(O)_2R^c$, —$S(O)_2$—$X^1$—$R^c$, —$S(O)_2$—$NR^h$—$R^c$, —$S(O)_2$—$NR^h$—$X^1$—$R^c$, —$NR^h$—$S(O)_2$—$R^c$, —$NR^h$—$S(O)_2$—$X^1$—$R^c$, and a 3- to 6-membered heterocycloalkyl having 1 to 3 heteroatom ring vertices independently selected from the group consisting of N, O, and S;

$X^1$ is selected from the group consisting of a bond and $C_{1-4}$ alkylene;

$R^c$ is selected from the group consisting of H, $C_{1-6}$ alkyl, $C_{1-6}$ haloalkyl, $C_{3-8}$ cycloalkyl, $C_{6-10}$ aryl, a 3- to 6-membered heterocycloalkyl having 1 to 3 heteroatom ring vertices independently selected from N, O, and S, and a 5- to 10-membered heteroaryl having 1 to 4 heteroatom ring vertices independently selected from the group consisting of N, O, and S, wherein the $C_{3-8}$ cycloalkyl, the $C_{6-10}$ aryl, the 3- to 6-membered heterocycloalkyl, and the 5- to 10-membered heteroaryl are substituted with 0 to 2 moieties independently selected from the group consisting of $C_{1-4}$ alkyl, —$OR^y$, —$X^3$—$OR^y$, —$C(O)R^y$, —$X^3$—$C(O)R^y$, —$C(O)OR^y$, and —$X^3$—$C(O)OR^y$, wherein each $R^y$ is selected from the group consisting of H, $C_{1-6}$ alkyl, and $C_{1-6}$ haloalkyl, and each $X^3$ is $C_{1-3}$ alkylene;

$R^f$ and $R^g$ are each independently selected from the group consisting of H, $C_{1-6}$ alkyl, $C_{1-6}$ haloalkyl, and phenyl; or $R^f$ and $R^g$ together with the nitrogen to which they are attached combine to form a 4- to 6-membered heterocycloalkyl ring comprising 0 to 2 additional heteroatoms independently selected from the group consisting of N, O, and S, wherein the phenyl and the 4- to 6-membered heterocycloalkyl are substituted with 0 to 2 moieties independently selected from the group consisting of $C_{1-4}$ alkyl, —$OR^x$, and —$X^2$—$OR^x$, wherein each $R^x$ is selected from the group consisting of H, $C_{1-4}$ alkyl, and $C_{1-4}$ haloalkyl, and each $X^2$ is $C_{1-3}$ alkylene;

$R^h$ is selected from the group consisting of H, $C_{1-6}$ alkyl, $C_{1-6}$ haloalkyl.

Embodiment 86. A method for treating a cancer in a patient, wherein the cancer is characterized by a reduction or absence of MTAP gene expression, the absence of the MTAP gene, or reduced function of MTAP protein, comprising administering to the subject a therapeutically effective amount of a compound of any one of embodiments 1 to 80, or a compound Formula (A).

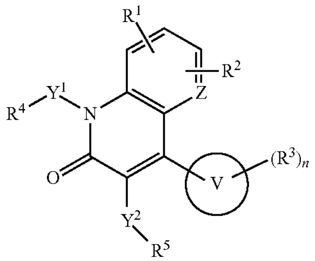

(A)

or a pharmaceutically acceptable salt thereof, optionally in a pharmaceutical composition, wherein Z is selected from the group consisting of CH and N;

$R^1$ and $R^2$ are each independently selected from the group consisting of H, $C_{1-6}$ alkyl, $C_{1-6}$ haloalkyl, $C_{1-6}$ alkoxy, cyano, halo and $C_{3-8}$ cycloalkyl, wherein the cycloalkyl group is substituted with from 0 to 2 groups independently selected from the group consisting of $C_{1-4}$ alkyl and halo;

ring V is a phenyl or a 5- to 6-membered heteroaryl comprising 1 to 3 heteroatom ring vertices independently selected from the group consisting of N, O, and S;

each $R^3$ is independently selected from the group consisting of halo, $C_{1-4}$ alkyl, $C_{1-4}$ haloalkyl, —$OR^z$, and —$X^4$—$OR^z$, wherein each $R^z$ is selected from the group consisting of H, $C_{1-4}$ alkyl, and $C_{1-4}$ haloalkyl, and each $X^4$ is $C_{1-3}$ alkylene;

the subscript n is 0, 1 or 2;

$Y^1$ is selected from the group consisting of a bond and $C_{1-4}$ alkylene;

$R^4$ is selected from the group consisting of H, halo, $C_{1-6}$ alkyl, $C_{1-6}$ haloalkyl, $C_{6-10}$ aryl, —$NR^aR^b$, —$C(O)R^d$, —$C(O)OR^d$, —$C(O)NR^aR^b$, and a 6- to 10-membered heteroaryl ring having 1 to 3 heteroatom ring vertices independently selected from the group consisting of N, O, and S; wherein $R^a$ and $R^b$ are each independently selected from the group consisting of H, $C_{1-6}$ alkyl, $C_{1-6}$ haloalkyl, and phenyl; wherein the phenyl is substituted with 0 to 2 moieties independently selected from the group consisting of $C_{1-4}$ alkyl, —$OR^x$, and —$X^2$—$OR^x$, and wherein each $R^x$ is selected from the group consisting of H, $C_{1-4}$ alkyl, and $C_{1-4}$ haloalkyl, and each $X^2$ is $C_{1-3}$ alkylene;

$R^d$ is selected from the group consisting of H, $C_{1-6}$ alkyl, and $C_{1-6}$ haloalkyl;

$Y^2$ is selected from the group consisting of a bond and $C_{1-4}$ alkylene;

$R^5$ is selected from the group consisting of H, halo, cyano, $C_{1-6}$ alkyl; $C_{1-6}$ haloalkyl, —$OR^c$, —O—$X^1$—$R^c$, —$SR^c$, —S—$X^1$—$R^c$, —$NR^fR^g$, —$S(O)_2R^c$, —$S(O)_2$—$X^1$—$R^c$, —$S(O)_2$—$NR^h$—$R^c$, —$S(O)_2$—$NR^h$—$X^1$—$R^c$, —$NR^h$—$S(O)_2$—$R^c$, —$NR^h$—$S(O)_2$—$X^1$—$R^c$, and a 3- to 6-membered heterocycloalkyl having 1 to 3 heteroatom ring vertices independently selected from the group consisting of N, O, and S;

$X^1$ is selected from the group consisting of a bond and $C_{1-4}$ alkylene;

$R^c$ is selected from the group consisting of H, $C_{1-6}$ alkyl, $C_{1-6}$ haloalkyl, $C_{3-8}$ cycloalkyl, $C_{6-10}$ aryl, a 3- to 6-membered heterocycloalkyl having 1 to 3 heteroatom ring vertices independently selected from N, O, and S, and a 5- to 10-membered heteroaryl having 1 to 4 heteroatom ring vertices independently selected from the group consisting of N, O, and S, wherein the $C_{3-8}$ cycloalkyl, the $C_6$_o aryl, the 3- to 6-membered heterocycloalkyl, and the 5- to 10-membered heteroaryl are substituted with 0 to 2 moieties independently selected from the group consisting of $C_{1-4}$ alkyl, —$OR^y$, —$X^3$—$OR^y$, —$C(O)R^y$, —$X^3$—$C(O)R^y$, —$C(O)OR^y$, and —$X^3$—$C(O)OR^y$, wherein each $R^y$ is selected from the group consisting of H, $C_{1-6}$ alkyl, and $C_{1-6}$ haloalkyl, and each $X^3$ is $C_{1-3}$ alkylene;

$R^f$ and $R^g$ are each independently selected from the group consisting of H, $C_{1-6}$ alkyl, $C_{1-6}$ haloalkyl, and phenyl; or $R^f$ and $R^g$ together with the nitrogen to which they are attached combine to form a 4- to 6-membered heterocycloalkyl ring comprising 0 to 2 additional heteroatoms independently selected from the group consisting of N, O, and S, wherein the phenyl and the 4- to 6-membered heterocycloalkyl are substituted with 0 to 2 moieties independently selected from the group consisting of $C_{1-4}$ alkyl, —$OR^x$, and —$X^2$—$OR^x$, wherein each $R^x$ is selected from the group consisting of H, $C_{1-4}$ alkyl, and $C_{1-4}$ haloalkyl, and each $X^2$ is $C_{1-3}$ alkylene;

$R^h$ is selected from the group consisting of H, $C_{1-6}$ alkyl, $C_{1-6}$ haloalkyl.

Embodiment 87. The method of any one of embodiments 83 to 86, wherein the cancer is selected from the group consisting of leukemia, glioma, melanoma, pancreatic, non-small cell lung cancer, bladder cancer, astrocytoma, osteosarcoma, head and neck cancer, myxoid chondrosarcoma, ovarian cancer, endometrial cancer, breast cancer, soft tissue sarcoma, non-Hodgkin lymphoma and mesothelioma.

EXAMPLES

The following examples and references (intermediates) are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: μg=microgram; μl or μL=microliter; mM=millimolar; M=micromolar; aa=amino acid(s); $Ac_2O$=acetic anhydride; AcCl=acetylchloride; ACN=acetonitrile; AIBN=2,2'-Azobis(2-methylpropionitrile); BID=twice daily; BINAP=2,2'-bis(diphenylphosphino)-1,1'-binaphthyl; $Boc_2O$ or $(Boc)_2O$=di-tert-butyl dicarbonate; bp=base pair(s); BSA=bovine serum albumin; BW=body weight; d=doublet; dd=doublet of doublets; DEAD=diethyl azodicarboxylate; DIBAL=diisobutylaluminium hydride DIEA=N,N-diisopropylethylamine; DIPEA=N,N-diisopropylethylamine; dl or dL=deciliter; DMA=dimethylacetamide; DMAP=dimethylaminopyridine; DME=1,2-dimethoxyethane; DMEM=Dulbeco's Modification of Eagle's Medium; DMF=N,N-dimethylformamide; DMSO=dimethylsulfoxide; dppf=1,1'-Bis(diphenylphosphino)ferrocene; DTT=dithiothreitol; EDTA=ethylenediaminetetraacetic acid; ES=electrospray; EtOAc=ethyl acetate; EtOH=ethanol; g=gram; h or hr=hour(s); HATU=2-(1H-7-azabenzotriazol-1-yl)-1,1,3,3-tetramethyluronium hexafluorophosphate; HEPES=4-(2-hydroxyethyl)-1-piperazineethylanesulfonic acid; HOAc=acetic acid; HPLC=high performance liquid chromatography; HPLC=high pressure liquid chromatography; i.m.=intramuscular(ly); i.p.=intraperitoneal(ly); IHC=immunohistochemistry; IPA=isopropyl alcohol; kb=kilobase(s); kDa=kilodalton; kg=kilogram; 1 or L=liter; LC=liquid chromatography; LCMS=liquid chromatography and mass spectrometry; m/z=mass to charge ratio; M=molar; m=multiplet; MeCN=acetonitrile; MeOH=methanol; $MeSO_2Cl$=methanesulfonylchloride; mg=milligram; min=minute(s); min=minutes; ml or mL=milliliter; mM=millimolar; MS=mass spectrometry; MsCl=methanesulfonylchloride; N=normal; NADPH=nicotinamide adenine dinucleotide phosphate; NBS=N-bromosuccinamide; ng=nanogram; nm=nanometer; nM=nanomolar; NMP=N-methylpyrrolidone; NMR=nuclear magnetic resonance; ns=not statistically significant; nt=nucleotides(s); PBS=phosphate-buffered saline; Pd/C=palladium on carbon; $Pd_2(dba)_3$=Tris (debenzylideneactone) dipalladium; $Pd(dppf)Cl_2$=1,1'-bis (diphenylphosphino)ferrocene-palladium(II)dichloride; PE=petroleum ether; QD=daily; QM=monthly; QW=weekly; rac=racemic; Rt=retention time; s=singlet; s or sec=second(s); sat.=saturated; SC or SQ=subcutaneous (ly); t=triplet; TBAB=tetra-n-butylammonium bromide; TEA=triethylamine; TFA=trifluoroacetic acid; THF=tetrahydrofuran; TLC=thin layer chromatography; TMSCl=trimethylsilylchloride; TsOH=p-toluenesulfonic acid; U=unit; wt=wildtype.

SYNTHETIC EXAMPLES

Example 1: Synthesis of 6-chloro-1-methyl-4-phenylquinolin-2(1H)-one (Compound 1.001)

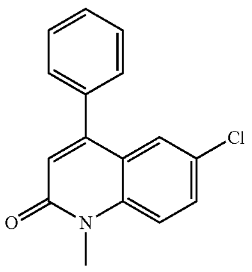 [SMILES: Cn1c(=O)cc(-c2ccccc2)c2cc(Cl)ccc21]

To a solution of 6-chloro-4-phenylquinolin-2-ol (0.1 g, 0.4 mmol, 1.00 equiv) in MeCN (2 mL) were added $K_2CO_3$ (0.11 g, 0.8 mmol, 2.00 equiv.) and $CH_3I$ (0.05 equiv) and the resulting mixture was stirred at RT for 16 h. The reaction mixture was quenched with water (5 mL) and extracted with EtOAc (2×10 mL). The organic layers were combined, washed with brine (10 mL) and dried over anhydrous $Na_2SO_4$. Purification by prep HPLC (mobile Phase A—0.1% aqueous formic acid, mobile phase B—MeCN, column—YMC C8 (150*19) mm, 10u, flow—25 ml/min, method—(T/% of B): 0/80, 10/80)) to afford 6-chloro-1-methyl-4-phenylquinolin-2(1H)-one (90 mg, 85%) as an off white solid.; $^1$HNMR (400 MHz, DMSO-$d_6$) δ 7.73-7.65 (m, 2H), 7.59-7.55 (m, 3H), 7.47 (dd, J=10.0, 3.0 Hz, 1H), 7.32 (d, J=8.5 Hz, 1H), 6.58 (s, 1H), 3.67 (s, 3H). LC-MS (ESI, m/z): 270.18 $[M+H]^+$.

Example 2: Synthesis of 6-chloro-3-methoxy-4-phenylquinolin-2(1H)-one (Compound 1.004)

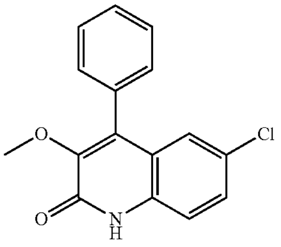

Step 1: Preparation of N-(2-benzoyl-4-chlorophenyl)-2-methoxyacetamide

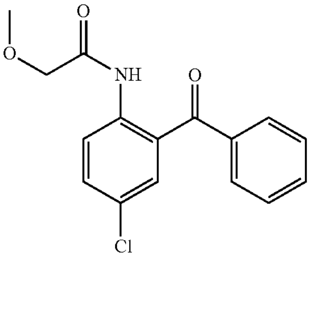 [SMILES: COCC(=O)Nc1ccc(Cl)cc1C(=O)c1ccccc1]

To a stirred solution of (2-amino-5-chlorophenyl)(phenyl) methanone (0.5 g, 2.25 mmol) and DIPEA (0.75 g, 4.31 mmol) in DCM (20 mL) was added 2-methoxyacetyl chloride (0.29 g, 3.23 mmol) at 0° C. The resulting reaction mixture was warm to RT and stirred for 3 h. The reaction mixture was quenched with ice-cold water (50 mL) and extracted with DCM (2×40 mL). The combined organic layers were washed with brine (50 mL), dried over anhydrous $Na_2SO_4$, filtered and concentrated. Purification by silica gel chromatography afforded N-(2-benzoyl-4-chlorophenyl)-2-methoxyacetamide (600 mg, 92%) as an off white solid; LC-MS (ESI, m/z): 304.17 $[M+H]^+$.

Step 2: Preparation of 6-chloro-3-methoxy-4-phenylquinolin-2(1H)-one

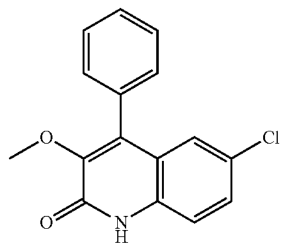

To a solution of N-(2-benzoyl-4-chlorophenyl)-2-methoxyacetamide (0.5 g, 1.6 mmol, 1.00 equiv.) in EtOH (5 mL) was added KOH (0.269 g, 4.8 mmol, 3.0 equiv). The resulting mixture was stirred at 75° C. for 16 hr. The reaction mixture was concentrated to get residue. The residue was quenched by 15 mL of water and the mixture was extracted with ethyl acetate (20 mL). The organic layer was combined, washed with water, brine and dried over anhydrous $Na_2SO_4$ to obtain crude product. The crude product was triturated with DCM (20 mL), solid was filtered and dried under vacuum to afford 6-chloro-3-methoxy-4-phenylquinolin-2(1H)-one (40 mg, 8%) as an off-white solid; $^1$HNMR (500 MHz, DMSO-$d_6$) δ 12.25 (s, 1H), 7.57-7.47 (m, 4H), 7.39-7.33 (m, 3H), 6.87 (d, 2.5 Hz, 1H), 3.71 (s, 3H). LC-MS (ESI, m/z): 286.20 $[M+H]^+$.

Example 3: Synthesis of 6-chloro-3-(methylsulfonyl)-4-phenylquinolin-2(1H)-one (Compound 1.005)

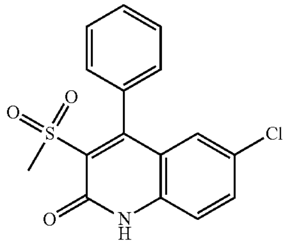 [SMILES: CS(=O)(=O)c1c(-c2ccccc2)c2cc(Cl)ccc2[nH]c1=O]

Step 1: Preparation of N-(2-benzoyl-4-chlorophenyl)-2-bromoacetamide

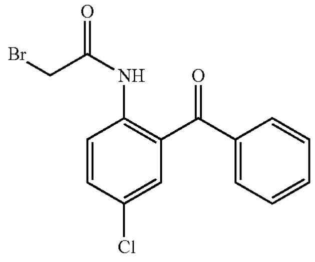 [SMILES: O=C(CBr)Nc1ccc(Cl)cc1C(=O)c1ccccc1]

To a stirred solution of (2-amino-5-chlorophenyl)(phenyl) methanone and N,N-diisopropylethylamine in DCM (20 mL) was added 2-bromoacetyl bromide at 0° C. The reaction mixture was allowed to RT and stirred for 3 h. Ice-cold water (20 mL) was added and the mixture was extracted with DCM (2×40 mL). The combined organic layers were washed with brine (30 mL), dried over anhydrous $Na_2SO_4$, filtered and concentrated. Purification by silica gel chromatography afforded N-(2-benzoyl-4-chlorophenyl)-2-bromoacetamide (500 mg, Yield: 66%) as an off white solid. LC-MS (ESI, m/z): 352.1 $[M+H]^+$.

Step 2: Preparation of 6-chloro-3-(methylthio)-4-phenylquinolin-2(1H)-one

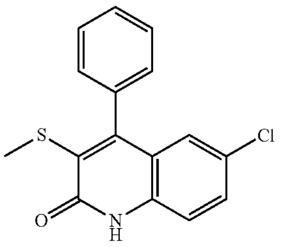

To a stirred solution of N-2(benzoyl-4-chlorophenyl)-2-acetamide (0.5 g, 1.4 mmol) in MeOH (5 ml) was added sodium methanethiolate (0.149 g, 2.1 mmol) at RT. The reaction mixture was stirred at room temperature for 16 h. The reaction mixture was quenched with aqueous NaOH (15 ml, 2.5 M) and extracted with EtOAc (2×10 ml). The combined organic layers were washed with brine (10 ml), dried over anhydrous $Na_2SO_4$, filtered and concentrated. Purification by silica gel chromatography afforded 6-chloro-3-(methylthio)-4-phenylquinolin-2(1H)-one (0.35 g, 82%) as an off white solid. LC-MS (ESI, m/z): 302.1 $[M+H]^+$.

Step 3: Preparation of 6-chloro-3-(methylsulfonyl)-4-phenylquinolin-2(1H)-one

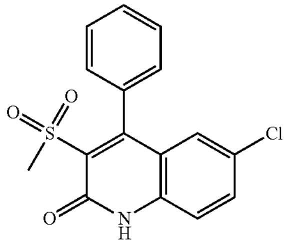 [SMILES: CS(=O)(=O)c1c(-c2ccccc2)c2cc(Cl)ccc2[nH]c1=O]

To a solution of 6-chloro-3-(methylthio)-4-phenylquinolin-2(1H)-one (0.2 g, 0.66 mmol, 1.00 equiv) in DCM (5 mL) was added mCPBA (0.57 g, 3.32 mmol, 5.00 equiv) at RT. The resulting mixture was stirred at RT for 2 hr. The reaction was quenched by addition of saturated aqueous $NaHCO_3$ (20 mL) and the mixture was extracted with DCM (2×15 mL). The organic layers were combined, washed with brine (10 mL) and dried over anhydrous $Na_2SO_4$. Purification by silica gel chromatography afforded 6-chloro-3-(methylsulfonyl)-4-phenylquinolin-2(1H)-one (0.15 g, 68%) as an off white solid; $^1$HNMR (500 MHz, DMSO-$d_6$) δ 12.70 (s, 1H), 7.72 (dd, J=9.0, 2.5 Hz, 1H), 7.49-7.44 (m, 4H), 7.29-7.27 (m, 2H), 6.74 (d, 2.0 Hz, 1H), 3.47 (d, 11.0 Hz, 3H). LC-MS (ESI, m/z): 334.18 $[M+H]^+$.

Example 4: Synthesis of 6-chloro-4-phenyl-3-(thieno[2,3-d]pyrimidin-4-ylthio)quinolin-2(1H)-one (Compound 1.006)

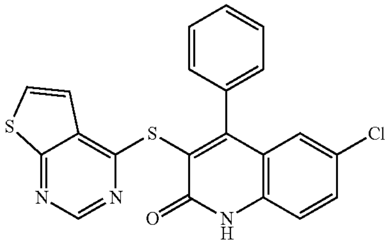 [SMILES: O=c1[nH]c2ccc(Cl)cc2c(-c2ccccc2)c1Sc1ncnc2sccc12]

Step 1: Preparation of 2-(thieno[2,3-d]pyrimidin-4-ylthio)acetic acid

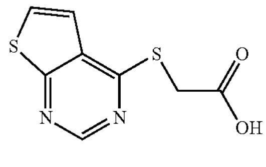 [SMILES: O=C(O)CSc1ncnc2sccc12]

To a stirred solution of 4-chlorothieno[2,3-d]pyrimidine (5.0 g, 29.3 mmol, 1.0 equiv) in DMF (30 mL) were added 2-mercaptoacetic acid (2.07 mL, 29.3 mmol, 1.0 equiv), $K_2CO_3$ (10.1 g, 73.25 mmol, 2.5 equiv) and the reaction mixture was stirred at 100° C. for 1 h. The reaction mixture was acidified with aqueous HCl (30 mL, 1 M) and extracted with EtOAc (3×50 mL). The combined organic layers were dried over $Na_2SO_4$ and concentrated to give 2-(thieno[2,3-d]pyrimidin-4-ylthio)acetic acid (3.5 g, 53%) as a brown solid. LC-MS (ESI, m/z): 227.09 $[M+H]^+$.

Step 2: Preparation of N-(2-benzoyl-4-chlorophenyl)-2-(thieno[2,3-d]pyrimidin-4-ylthio)acetamide

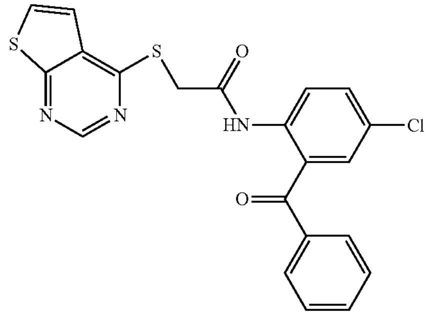 [SMILES: O=C(CSc1ncnc2sccc12)Nc1ccc(Cl)cc1C(=O)c1ccccc1]

To a stirred solution of 2-(thieno[2,3-d]pyrimidin-4-ylthio)acetic acid (0.5 g, 2.2 mmol, 1.0 equiv) in DMF (20 mL) was added (2-amino-5-chlorophenyl)(phenyl)methanone (0.616 g, 2.64 mmol, 1.2 equiv), propylphosphonic anhydride (1.8 mL, 5.7 mmol, 2.6 equiv, 50% in EtOAc), DIPEA (1.8 mL, 11 mmol, 5.0 equiv) and the resulting mixture was stirred at RT for 16 h. The reaction mixture was diluted with water (20 mL) and extracted with ethyl acetate (3×30 mL). The combined organic layers were dried over anhydrous $Na_2SO_4$ and concentrated. Purification by silica gel chromatography afforded N-(2-benzoyl-4-chlorophenyl)-2-(thieno[2,3-d]pyrimidin-4-ylthio)acetamide (0.3 g, 30.8%) as an off white solid. LC-MS (ESI, m/z): 440.1 $[M+H]^+$.

Step 3: Preparation of 6-chloro-4-phenyl-3-(thieno[2,3-d]pyrimidin-4-ylthio)quinolin-2(1H)-one

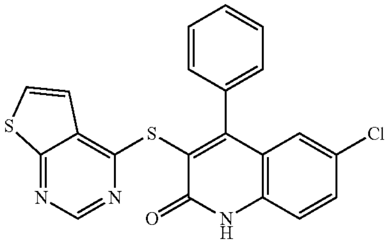 [SMILES: O=c1[nH]c2ccc(Cl)cc2c(-c2ccccc2)c1Sc1ncnc2sccc12]

To a stirred solution of N-(2-benzoyl-4-chlorophenyl)-2-(thieno[2,3-d]pyrimidin-4-ylthio)acetamide (0.3 g, 0.2 mmol, 1.0 equiv) in MeOH (10 mL) was added NaOMe (0.056 g, 1.05 mmol, 5.0 equiv) and the reaction mixture was stirred at RT for 6 hr. The reaction mixture was diluted with water (10 mL) and extracted with DCM (3×10 mL). The combined organic layers were dried over anhydrous $Na_2SO_4$ and concentrated to give 6-chloro-4-phenyl-3-(thieno[2,3-d]pyrimidin-4-ylthio)quinolin-2(1H)-one (0.1 g, 34.8%) as an off white solid; $^1$HNMR (500 MHz, DMSO-$d_6$) δ 12.44 (s, 1H), 8.75 (s, 1H), 7.95 (d, J=6 Hz, 1H), 7.70-7.68 (m, 1H), 7.50-7.46 (m, 5H), 7.33-7.31 (m, 2H), 6.92 (d, J=2.5 Hz, 1H). LC-MS (ESI, m/z): 422.2 $[M+H]^+$.

Example 5: Synthesis of 6-chloro-3-(methylamino)-4-phenylquinolin-2(1H)-one (Compound 1.007)

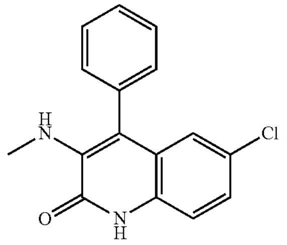

Step 1: Preparation of N-(2-benzoyl-4-chlorophenyl)-2-bromoacetamide

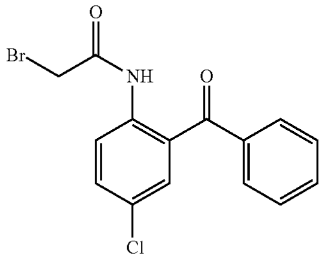 [SMILES: O=C(CBr)Nc1ccc(Cl)cc1C(=O)c1ccccc1]

The synthesis of the title compound was described in Example 3, step 1.

Step 2: Preparation of N-(2-benzoyl-4-chlorophenyl)-2-(methylamino)acetamide

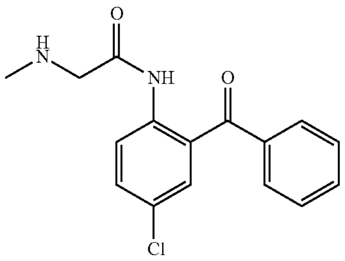 [SMILES: CNCC(=O)Nc1ccc(Cl)cc1C(=O)c1ccccc1]

To a solution of N-(2-benzoyl-4-chlorophenyl)-2-bromoacetamide (0.5 g, 1.4 mmol, 1.00 equiv) in MeCN (10 mL) were added $K_2CO_3$ (0.98 g, 7.1 mmol, 5.00 equiv), $MeNH_2 \cdot HCl$ (0.34 g, 4.2 mmol, 3.00 equiv) and the resulting mixture was stirred at 90° C. for 16 hr. Water (10 mL) was added and the mixture was extracted with EtOAc (3×40 mL). The organic layers were combined, washed with brine (20 mL) and dried over anhydrous $Na_2SO_4$. Purification by silica gel chromatography afforded N-(2-benzoyl-4-chlorophenyl)-2-(methylamino)acetamide as a yellow semi solid (250 mg, 58%). LC-MS (ESI, m/z): 303.26 $[M+H]^+$.

Step 3: Preparation of 6-chloro-3-(methylamino)-4-phenylquinolin-2(1H)-one

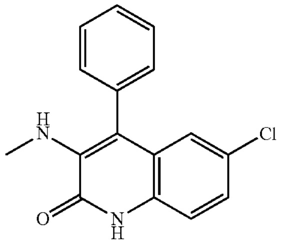

To a solution of N-(2-benzoyl-4-chlorophenyl)-2-(methylamino)acetamide (0.25 g, 0.8 mmol, 1.0 equiv) in MeOH (5 mL) was added NaOMe (0.178 g, 3.3 mmol, 4.00 equiv) at RT and the resulting mixture was stirred at 80° C. for 16 hr. MeOH was evaporated under reduced pressure and the residue was diluted with water (5 mL) and the mixture was extracted with DCM (2×15 mL). The combined organic layers were washed with brine (10 mL) and dried by anhydrous $Na_2SO_4$. Purification by prep HPLC (mobile phase A—0.1% aqueous formic acid, mobile phase B—MeCN, column—KROMASIL C18 (25×150) mm 10u, flow—25 ml/min, gradient method) afforded 6-chloro-3-(methylamino)-4-phenylquinolin-2(1H)-one (40 mg, 17%) as an off white solid; $^1$HNMR (500 MHz, DMSO-$d_6$) δ 12.15 (s, 1H), 7.52-7.44 (m, 3H), 7.37-7.35 (m, 2H), 7.25 (d, J=8.5 Hz, 1H), 7.17 (dd, J=8.5, 2.0 Hz, 1H), 6.65 (d, J=2.0 Hz, 1H), 5.89 (q, J=11.0 Hz, 1H), 2.19 (d, J=6.0 Hz, 3H). LC-MS (ESI, m/z): 285.21 $[M+H]^+$.

Example 6: Synthesis of 6-chloro-3-(dimethylamino)-4-phenylquinolin-2(1H)-one (Compound 1.008)

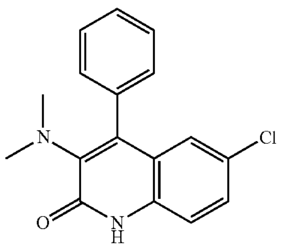

The title compound was prepared by the procedure described in Example 5, by substituting $MeNH_2 \cdot HCl$ with $Me_2NH \cdot HCl$ in step 2; $^1$HNMR (500 MHz, DMSO-$d_6$) δ 11.94 (s, 1H), 7.56-7.52 (m, 2H), 7.47-7.45 (m, 1H), 7.39-7.37 (m, 1H), 7.32-7.29 (m, 3H), 6.87 (d, J=2.5 Hz, 1H), 2.50-2.48 (m, 6H). LC-MS (ESI, m/z): 299.2 $[M+H]^+$.

Example 7: Synthesis of 6-bromo-3-methoxy-4-phenylquinolin-2(1H)-one (Compound 1.009)

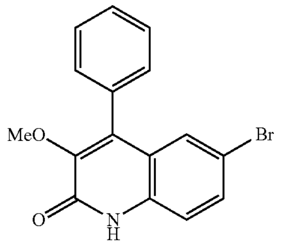 [SMILES: COc1c(-c2ccccc2)c2cc(Br)ccc2[nH]c1=O]

Step 1: Preparation of N-(2-benzoyl-4-bromophenyl)-2-methoxyacetamide

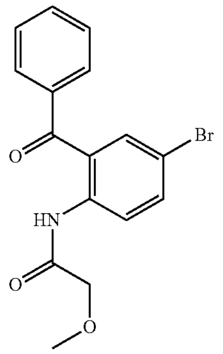 [SMILES: COCC(=O)Nc1ccc(Br)cc1C(=O)c1ccccc1]

The title compound was prepare by the procedure described in Example 2, by substituting (2-amino-5-chlorophenyl)(phenyl)methanone with (2-amino-5-bromophenyl)(phenyl)methanone in step 1.

Step 2: Preparation of 6-bromo-3-methoxy-4-phenylquinolin-2(1H)-one

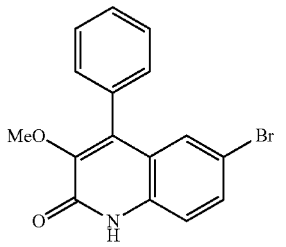 [SMILES: COc1c(-c2ccccc2)c2cc(Br)ccc2[nH]c1=O]

To a solution of N-(2-benzoyl-4-bromophenyl)-2-methoxyacetamide ((1 g, 2.9 mmol, 1.00 equiv) in EtOH (20 mL) at RT was added NaOH (0.232 g, 5.8 mmol, 2.00 equiv) and the resulting mixture was stirred at 80° C. for 1 hr. The solvent was evaporated under reduced pressure to obtain the crude compound. Purification by prep HPLC (mobile phase A—10 mM ammonium bicarbonate in water, mobile phase B—MeCN, column—KROMASIL C18 (25×150) mm 10u, flow—25 ml/min, gradient method) afforded 6-bromo-3-methoxy-4-phenylquinolin-2(1H)-one (150 mg, 16%) as an off white solid; $^1$HNMR (500 MHz, DMSO-$d_6$) δ 12.25 (s, 1H), 7.60-7.54 (m, 3H), 7.51-7.48 (m, 1H), 7.35-7.32 (m, 3H), 7.01 (d, J=2.0 Hz, 1H), 3.71 (s, 3H). LC-MS (ESI, m/z): 330.25 $[M+H]^+$.

Example 8: Synthesis of 6-chloro-3-hydroxy-4-phenylquinolin-2(1H)-one (Compound 1.010)

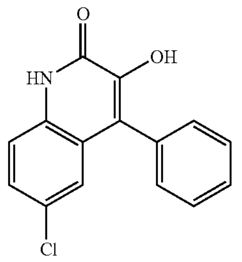 [SMILES: O=c1[nH]c2ccc(Cl)cc2c(-c2ccccc2)c1O]

Step 1: Preparation of N-(2-benzoyl-4-chlorophenyl)-2-bromoacetamide

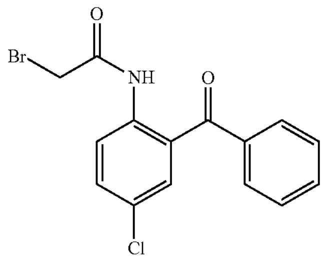 [SMILES: O=C(CBr)Nc1ccc(Cl)cc1C(=O)c1ccccc1]

The synthesis of the title compound was described in Example 3, step 1.

Step 2: Preparation of 6-chloro-3-hydroxy-4-phenylquinolin-2(1H)-one

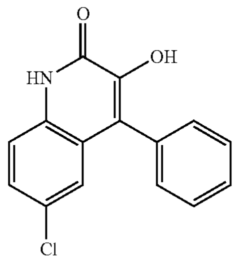 [SMILES: O=c1[nH]c2ccc(Cl)cc2c(-c2ccccc2)c1O]

To a solution of N-(2-benzoyl-4-chlorophenyl)-2-bromoacetamide (0.3 g, 0.9 mmol, 1.00 equiv) in MeOH (10 mL) at 0° C. was added NaOMe (0.194 g, 3.6 mmol, 4.00 equiv) and the resulting mixture was stirred at RT for 16 hr. Water (10 mL) was added and the mixture was extracted with EtOAc (2×20 mL). The combined organic layers were washed with brine (10 mL) and dried over anhydrous $Na_2SO_4$. Purification by prep HPLC (mobile phase A—10 mM aqueous ammonium bicarbonate, mobile phase B—MeCN, column—KROMASIL C18 (25×150) mm 10u, flow—25 ml/min, gradient method) afforded 6-chloro-3-hydroxy-4-phenylquinolin-2(1H)-one (0.028 g, 12%) as an off white solid; $^1$HNMR (500 MHz, DMSO-$d_6$) δ 12.41 (s, 1H), 9.56 (s, 1H), 7.54-7.51 (m, 2H), 7.44-7.46 (m, 1H), 7.38-7.33 (m, 4H), 6.93 (t, 1.5 Hz, 1H). LC-MS (ESI, m/z): 272.24 $[M+H]^+$.

Example 9: Synthesis of 6-cyclopropyl-3-methoxy-4-phenylquinolin-2(1H)-one (Compound 1.011)

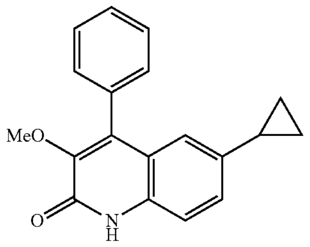 [SMILES: COc1c(-c2ccccc2)c2cc(C3CC3)ccc2[nH]c1=O]

Step 1: Preparation of (2-amino-5-cyclopropylphenyl)(phenyl)methanone

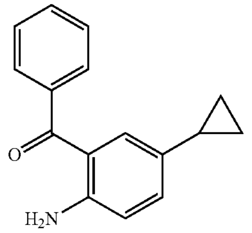 [SMILES: Nc1ccc(C2CC2)cc1C(=O)c1ccccc1]

A mixture of (2-amino-5-bromophenyl)(phenyl)methanone (1.0 g, 3.6 mmol, 1.00 equiv), cyclopropylboronic acid (0.3711 g, 4.32 mmol, 1.20 equiv) and $K_2CO_3$ (1.49 g, 10.8 mmol, 3.00 equiv) in 3:1 v/v dioxane and water (40 mL) was degassed with argon for 10 min. Pd(dppf)$Cl_2$·$CH_2Cl_2$ (0.147 g, 0.18 mmol, 0.05 equiv) was added and the resulting mixture was stirred at 100° C. for 3 hr. Water (30 mL) was added and the mixture was extracted with EtOAC (3×50 mL). The combined organic layers were washed with brine (10 mL) and dried over anhydrous $Na_2SO_4$. Purification by silica gel chromatography afforded (2-amino-5-cyclopropylphenyl)(phenyl)methanone as a pale yellow solid (650 mg, 75.6%); LC-MS (ESI, m/z): 238.35 $[M+H]^+$.

Step 2: Preparation of 6-cyclopropyl-3-methoxy-4-phenylquinolin-2(1H)-one

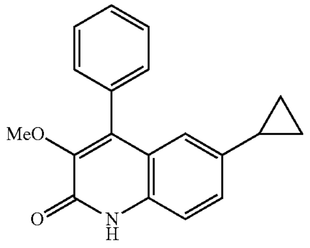 [SMILES: COc1c(-c2ccccc2)c2cc(C3CC3)ccc2[nH]c1=O]

The title compound was prepared by following the procedure described in Experiment 4, by replacing (2-amino-5-chlorophenyl)(phenyl)methanone with (2-amino-5-cyclopropylphenyl)(phenyl)methanone in step 1. $^1$HNMR (500 MHz, DMSO-$d_6$) δ 12.01 (s, 1H), 7.55-7.52 (m, 2H), 7.49-7.46 (m, 1H), 7.33-7.30 (m, 2H), 7.26 (d, J=8.5 Hz, 1H), 7.10 (dd, J=8.5, 2.0 Hz, 1H), 6.72 (d, J=2.0 Hz, 1H), 3.67 (s, 3H), 1.82-1.77 (m, 1H), 0.85-0.81 (m, 2H), 0.47-0.46 (m, 2H). LC-MS (ESI, m/z): 292.42 $[M+H]^+$.

Example 10: Synthesis of 6-chloro-3-methoxy-4-(pyridin-3-yl)quinolin-2(1H)-one (Compound 1.012)

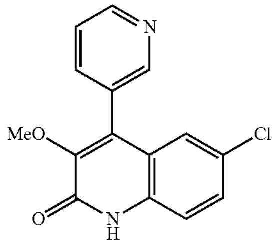 [SMILES: COc1c(-c2cccnc2)c2cc(Cl)ccc2[nH]c1=O]

Step 1: Preparation of 2-amino-5-chloro-N-methoxy-N-methylbenzamide

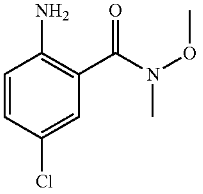

To a solution of 2-amino-5-chlorobenzoic acid (10 g, 58.3 mmol, 1.0 equiv) in DMF (100 mL) were added DIPEA (45.1 g, 349.8 mmol, 6.0 equiv), HATU (33.2 g, 87.4 mmol, 1.5 equiv) at RT and the mixture was stirred for 30 min. N,O-dimethylhydroxylamine (27.8 g, 291.5 mmol, 5.00 equiv) was added and the resulting mixture was stirred at RT for 16 hr. All the volatiles were evaporated under reduced pressure and water (100 mL) was added to the crude residue and extracted with EtOAc (2×100 mL). The organic layers were combined, washed with brine (20 mL) and dried over anhydrous $Na_2SO_4$. Purification by silica gel chromatography afforded 2-amino-5-chloro-N-methoxy-N-methylbenzamide as an off white solid (8.0 g, 65%); LC-MS (ESI, m/z): 215.26 $[M+H]^+$.

Step 2: Preparation of (2-amino-5-chlorophenyl)(pyridin-3-yl)methanone

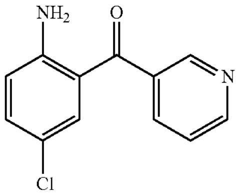 [SMILES: Nc1ccc(Cl)cc1C(=O)c1cccnc1]

To a solution of 3-bromo pyridine (1.0 g, 6.9 mmol, 3.00 equiv) in THF (10 mL) at 0° C. was added isopropylmagnesium bromide (3.4 mL, 1.7 mmol, 1.00 equiv, 2.0 M in THF) and stirred at RT for 1 hr. To the above mixture was added a solution of 2-amino-5-chloro-N-methoxy-N-methylbenzamide (0.5 g, 2.3 mmol, 1.00 equiv) in THF (5 mL) dropwise at 0° C. and the resulting mixture was stirred at RT for 1 hr. The reaction mixture was cooled to 0° C., saturated $NH_4Cl$ (10 mL) was added and extracted with EtOAc (2×30 mL). The combined organic layers were washed with brine (10 mL), dried over anhydrous $Na_2SO_4$, filtered and concentrated. Purification by silica gel chromatography afforded (2-amino-5-chlorophenyl)(pyridin-3-yl)methanone as a thick oil (200 mg, 36%); LC-MS (ESI, m/z): 233.21 $[M+H]^+$.

Step 3: Preparation of 6-chloro-3-methoxy-4-(pyridin-3-yl)quinolin-2(1H)-one

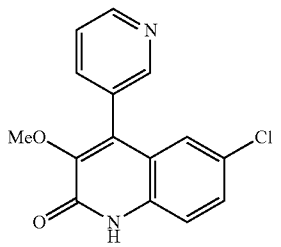

The title compound was prepared by following the procedure described in Experiment 4, by replacing (2-amino-5-chlorophenyl)(phenyl)methanone with (2-amino-5-chlorophenyl)(pyridin-3-yl)methanone in step 1; $^1$HNMR (500 MHz, DMSO-$d_6$) δ 12.35 (s, 1H), 8.70 (dd, J=5.0, 1.5 Hz, 1H), 8.57 (d, J=1.5 Hz, 1H), 7.85-7.82 (m, 1H), 7.60-7.58 (m, 11H), 7.51 (dd, J=9.0, 2.5 Hz, 1H), 7.41 (d, J=9.0 Hz, 1H), 6.88 (d, 2.5 Hz, 1H), 3.76 (s, 3H). LC-MS (ESI, m/z): 287.36 $[M+H]^+$.

Example 11: Synthesis of 3-(benzo[d]thiazol-2-ylthio)-6-chloro-4-phenylquinolin-2(1H)-one (Compound 1.013)

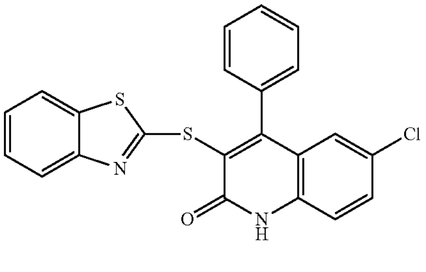 [SMILES: O=c1[nH]c2ccc(Cl)cc2c(-c2ccccc2)c1Sc1nc2ccccc2s1]

Step 1: Preparation of N-(2-benzoyl-4-chlorophenyl)-2-bromoacetamide

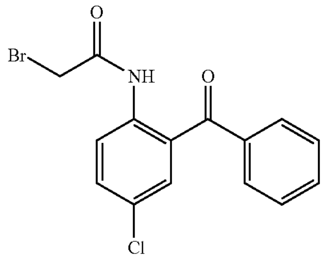 [SMILES: O=C(CBr)Nc1ccc(Cl)cc1C(=O)c1ccccc1]

The synthesis of the title compound was described in Example 3, step 1.

Step 2: Preparation of 3-(benzo[d]thiazol-2-ylthio)-6-chloro-4-phenylquinolin-2(1H)-one

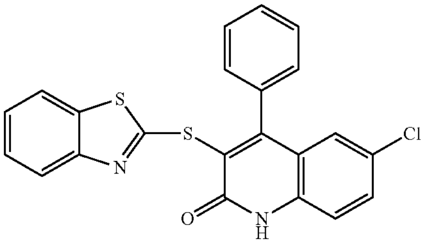 [SMILES: O=c1[nH]c2ccc(Cl)cc2c(-c2ccccc2)c1Sc1nc2ccccc2s1]

To a solution of benzo[d]thiazole-2-thiol (1.04 g, 6.27 mmol, 1.00 equiv) in MeOH (20 mL) was added NaOMe (0.369 g, 6.84 mmol, 1.20 equiv), heated to 60° C. and stirred for 30 min. Then N-(2-benzoyl-4-chlorophenyl)-2-bromoacetamide (2.0 g, 5.7 mmol, 1.10 equiv) was added at 60° C. and the resulting mixture was stirred at 60° C. for 16 hr. Water (20 mL) was added and the mixture was extracted with EtOAc (2×50 mL). The combined organic layers were dried over $Na_2SO_4$, filtered and concentrated. Purification by prep HPLC (mobile phase A—0.10% aqueous formic acid, mobile phase B—MeCN, column—KROMASIL C18 (25×150) mm 10u, flow—25 ml/min, gradient method) afforded 3-(benzo[d]thiazol-2-ylthio)-6-chloro-4-phenylquinolin-2(1H)-one as an off white solid (21 mg, 17.5%); $^1$HNMR (500 MHz, DMSO-$d_6$) δ 12.85-12.51 (m, 1H), 7.93 (d, J=0.5 Hz, 1H), 7.91 (d, J=0.5 Hz, 1H), 7.80-7.70 (m, 1H), 7.56-7.50 (m, 4H), 7.49-7.42 (m, 1H), 7.42-7.30 (m, H), 6.92 (d, J=2.0 Hz, 1H). LC-MS (ESI, m/z): 421.36 $[M+H]^+$.

Example 12: Synthesis of 6-chloro-N-methyl-2-oxo-4-phenyl-1,2-dihydroquinoline-3-sulfonamide (Compound 1.014)

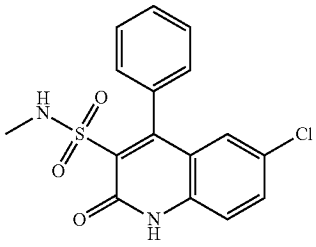 [SMILES: CNS(=O)(=O)c1c(-c2ccccc2)c2cc(Cl)ccc2[nH]c1=O]

Step 1: Preparation of 6-chloro-3-mercapto-4-phenylquinolin-2(1H)-one

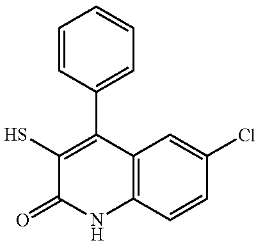 [SMILES: O=c1[nH]c2ccc(Cl)cc2c(-c2ccccc2)c1S]

The synthesis of the title compound is described in Example 13.

Step 2: Preparation of 6-chloro-N-methyl-2-oxo-4-phenyl-1,2-dihydroquinoline-3-sulfonamide

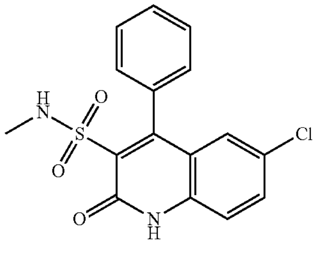 [SMILES: CNS(=O)(=O)c1c(-c2ccccc2)c2cc(Cl)ccc2[nH]c1=O]

To a stirred solution of 6-chloro-3-mercapto-4-phenylquinolin-2(1H)-one (0.1 g, 0.3 mmol, 1.0 equiv) in MeCN (10 mL) was added $H_2O_2$ (0.2 mL, 1.2 mmol, 4.0 equiv, 30% in water), thionyl chloride (0.02 ml, 0.3 mmol, 1.0 equiv) at 0° C. and reaction mixture was stirred at RT for 6 h. Methyl amine (1 mL) and pyridine (1 mL) were added and reaction was heated at 70° C. for 3 hr. The reaction mixture was diluted with water (20 mL) and extracted with EtOAc (2×20 mL). The combined organic layers were washed with brine (10 mL), dried over anhydrous sodium sulphate, filtered and concentrated. Purification by prep HPLC (mobile phase A—10 mM aqueous ammonium bicarbonate, mobile phase B—MeCN, column—X-Select C18 (19×250) mm 5u, flow—18 ml/min, gradient method) gave 6-chloro-N-methyl-2-oxo-4-phenyl-1,2-dihydroquinoline-3-sulfonamide (18 mg, 18%) as an off white solid.; $^1$HNMR (500 MHz, DMSO-$d_6$) δ 12.68 (br s, 1H), 7.69 (dd, J=9.0, 2.5 Hz, 1H), 7.51-7.44 (m, 4H), 7.26-7.24 (m, 2H), 6.88-6.86 (m, 1H), 6.72 (d, J=2.5 Hz, 1H), 2.44 (d, J=5.0 Hz, 1H). LC-MS (ESI, m/z): 349.35 $[M+H]^+$.

Example 13: Synthesis of 6-chloro-3-mercapto-4-phenylquinolin-2(1H)-one (Compound 1.015)

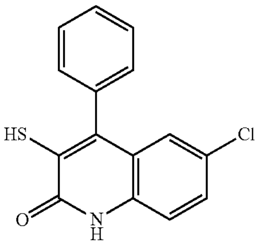 [SMILES: O=c1[nH]c2ccc(Cl)cc2c(-c2ccccc2)c1S]

Step 1: Preparation of 3-(tert-butylthio)-6-chloro-4-phenylquinolin-2(1H)-one

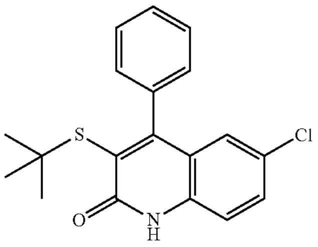 [SMILES: CC(C)(C)Sc1c(-c2ccccc2)c2cc(Cl)ccc2[nH]c1=O]

The title compound was prepared by the procedure described in Example 11, by replacing benzo[d]thiazole-2-thiol with tert-butylthiol in step 2. LC-MS (ESI, m/z): 344.36 $[M+H]^+$.

Step 2: Preparation of 6-chloro-3-mercapto-4-phenylquinolin-2(1H)-one

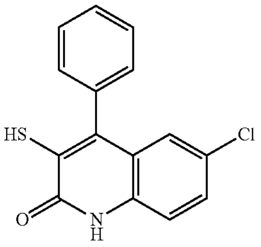 [SMILES: O=c1[nH]c2ccc(Cl)cc2c(-c2ccccc2)c1S]

To a solution of 3-(tert-butylthio)-6-chloro-4-phenylquinolin-2(1H)-one (0.3 g, 0.9 mmol, 1.00 equiv) in TFA (0.2 ml, 2.7 mmol, 3.00 equiv). The resulting mixture was stirred at 65° C. for 16 hr. The reaction mixture was quenched addition of water (5 mL) and the mixture was extracted with EtOAc (2×20 mL). The organic layers were combined, washed with brine (20 mL) and dried over anhydrous $Na_2SO_4$. Purification by prep HPLC (mobile phase A—0.10% aqueous formic acid, mobile phase B—MeCN, column—XBRIDGE C18 (19×250) mm 5u, flow—18 ml/min, gradient method) afforded 6-chloro-3-mercapto-4-phenylquinolin-2(1H)-one as a pale green solid (38 mg, 15%); $^1$HNMR (500 MHz, DMSO-$d_6$) δ 12.48 (S, 1H), 7.68-7.55 (m, 2H), 7.55-7.50 (m, 1H), 7.50-7.44 (m, 1H), 7.41 (d, J=8.5 Hz, 1H), 7.33 (dd, J=8.5, 1.5 Hz, 2H), 6.77 (d, J=2.0 Hz, 1H). LC-MS (ESI, m/z): 288.32 $[M+H]^+$.

Example 14: Synthesis of 6-chloro-2-oxo-4-phenyl-N-propyl-1,2-dihydroquinoline-3-sulfonamide (Compound 1.016)

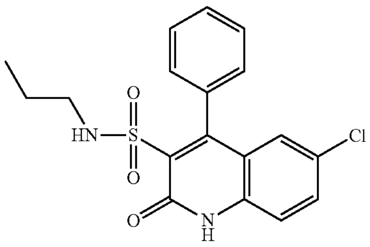 [SMILES: CCCNS(=O)(=O)c1c(-c2ccccc2)c2cc(Cl)ccc2[nH]c1=O]

The title compound was prepared by the procedure described in Example 12, by replacing methylamine with n-propylamine in step 2; $^1$HNMR (500 MHz, DMSO-$d_6$) δ 12.69 (s, 11H), 7.67 (dd, J=9.0, 2.0 Hz, 1H), 7.52-7.43 (m, 4H), 7.23 (dd, J=7.5, 1.5 Hz, 2H), 7.07 (br s, 1H), 6.72 (d, J=2.5 Hz, 1H), 2.77-2.73 (m, 2H), 1.40-1.34 (m, 2H), 0.78 (t, J=7.0 Hz, 3H). LC-MS (ESI, m/z): 377.38 $[M+H]^+$.

Example 15: Synthesis of 6-chloro-3-hydroxy-4-(o-tolyl)quinolin-2(1H)-one (Compound 1.017)

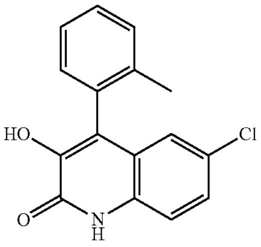

A mixture of 2-methylbenzaldehyde (0.1322 g, 1.1 mmol, 1.10 equiv) and 4-methylbenzenesulfonohydrazide (0.2047 g, 1.1 mmol, 1.10 equiv) in EtOH (5 mL) was stirred at RT until TLC showed complete conversion of the starting materials. 5-chloroindoline-2,3-dione (0.2 g, 1.1 mmol, 1.10 equiv) and $K_2CO_3$ (0.304 g, 2.2 mmol, 2.00 equiv) were added and the resulting mixture was stirred at 80° C. for 8 hr. The solvent was evaporated and water (5 mL) and EtOAc (10 mL) were added. The two layers were separated and the aqueous layer was further extracted with EtOAc (2×10 mL). The combined organic layers were washed with brine (10 mL), dried over anhydrous $Na_2SO_4$, filtered and concentrated. Purification by prep HPLC (mobile Phase A—0.1% aqueous formic acid, mobile phase B—MeCN, column—X-Select C18 (19×250) mm 5u, flow—18 ml/min, gradient method) afforded 6-chloro-3-hydroxy-4-(o-tolyl)quinolin-2 (1H)-one as an off white solid (130 mg, 41%); $^1$HNMR (500 MHz, DMSO-$d_6$) δ 12.39 (S, 1H), 9.56 (s, 1H), 7.40-7.31 (m, 5H), 7.13 (d, 7.5 Hz, 1H), 6.67 (s, 1H), 2.02 (s, 3H). LC-MS (ESI, m/z): 286.16 $[M+H]^+$.

Example 16: Synthesis of 3-hydroxy-4-(o-tolyl)-6-(trifluoromethyl)quinolin-2(1H)-one (Compound 1.018)

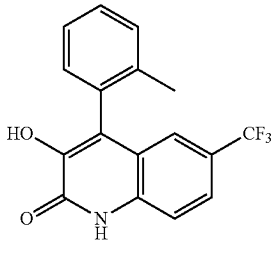 [SMILES: Cc1ccccc1-c1c(O)c(=O)[nH]c2ccc(C(F)(F)F)cc12]

The title compound was prepared by the procedure described in Example 15, by replacing 5-chloroindoline-2,3-dione with 5-(trifluoromethyl)indoline-2,3-dione; $^1$HNMR (500 MHz, DMSO-$d_6$) δ 12.57 (s, 11H), 9.68 (s, 11H), 7.66-7.64 (m, 1H) 7.41-7.40 (m, 11H), 7.38-7.33 (m, 3H), 7.16 (d, 7.5 Hz, 1H), 7.00 (s, 1H), 2.02 (s, 3H). LC-MS (ESI, m/z): 320.30 $[M+H]^+$.

Example 17: Synthesis of 3-methoxy-4-phenyl-6-(trifluoromethyl)quinolin-2(1H)-one (Compound 1.019)

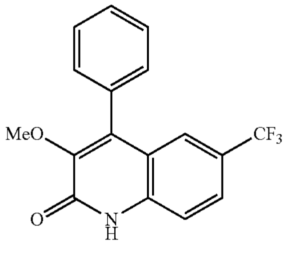 [SMILES: COc1c(-c2ccccc2)c2cc(C(F)(F)F)ccc2[nH]c1=O]

Step 1: Preparation of tert-butyl (2-benzoyl-4-(trifluoromethyl)phenyl)carbamate

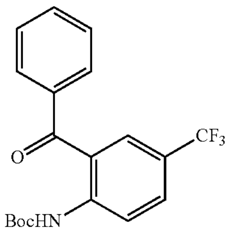 [SMILES: CC(C)(C)OC(=O)Nc1ccc(C(F)(F)F)cc1C(=O)c1ccccc1]

To a solution of tert-butyl (4-(trifluoromethyl)phenyl) carbamate (0.5 g, 1.9 mmol, 1.00 equiv) in THF (10 mL) was added tert-butyllithium (3.6 mL, 5.7 mmol, 3.00 equiv) dropwise at −78° C. and the resulting suspension was stirred for 15 min. The reaction mixture was allowed to warm to −45° C. and stirred for 2 h. Then reaction mixture was cooled to −78° C. and added methyl benzoate (0.284 g, 2.1 mmol, 1.1 equiv) was added. The resulting solution was warmed to −45° C. and stirred at the same temperature for 1 h. Saturated $NH_4Cl$ (10 mL) was added and the mixture was diluted with water (20 ml) and extracted with EtOAc (2×20 mL). The combined organic layers were washed with brine (15 mL) and dried over anhydrous $Na_2SO_4$. Purification by silica gel chromatography afforded tert-butyl (2-benzoyl-4-(trifluoromethyl)phenyl)carbamate as a white solid (0.4 g, 60%). LC-MS (ESI, m/z): 364.22 $[M-H]^+$.

Step 2: Preparation of (2-amino-5-(trifluoromethyl) phenyl)(phenyl)methanone

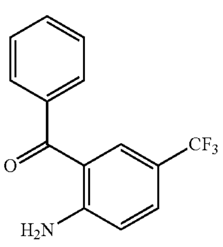 [SMILES: Nc1ccc(C(F)(F)F)cc1C(=O)c1ccccc1]

To a solution of tert-butyl (2-benzoyl-4-(trifluoromethyl) phenyl) carbamate (0.4 g, 1.1 mmol, 1.0 equiv) in 1,4-dioxane (2 mL) was added HCl (0.55 mL, 2.2 mmol, 2 equiv, 4 M in dioxane) at RT, then the reaction mixture was stirred for 2 h. All the volatiles were evaporated under reduced pressure and the compound obtained was washed with pentane (2×10 mL) to afford (2-amino-5-(trifluoromethyl) phenyl)(phenyl)methanone as a pale yellow liquid (0.22 g). Ionization was not observed in mass spectrum.

Step 3: Preparation of N-(2-benzoyl-4-(trifluoromethyl)phenyl)-2-methoxyacetamide

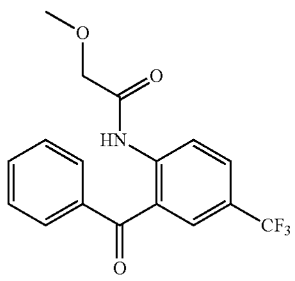 [SMILES: COCC(=O)Nc1ccc(C(F)(F)F)cc1C(=O)c1ccccc1]

To a solution of (2-amino-5-(trifluoromethyl)phenyl) (phenyl)methanone (0.22 g, 0.8 mmol, 1.0 equiv) in DCM (5 mL) was added DIPEA (0.206 g, 1.6 mmol, 2.0 equiv) followed by the addition of 2-bromoacetyl bromide (0.172 g, 1.6 mmol, 2.0 equiv) at RT. The resulting mixture was stirred at RT for 2 h. The reaction mixture was diluted with water (10 mL) and extracted with EtOAc (2×20 mL). The combined organic layers were washed with brine (10 mL) and dried over anhydrous $Na_2SO_4$. Evaporation under reduced pressure afforded N-(2-benzoyl-4-(trifluoromethyl) phenyl)-2-methoxyacetamide as pale yellow liquid (0.22 g, 81%); LC-MS (ESI, m/z): 338.19 $[M+H]^+$.

Step 4: Preparation of 3-methoxy-4-phenyl-6-(trifluoromethyl)quinolin-2(1H)-one

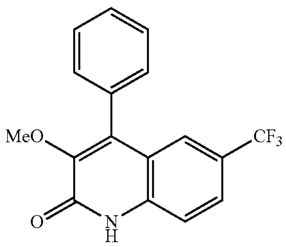 [SMILES: COc1c(-c2ccccc2)c2cc(C(F)(F)F)ccc2[nH]c1=O]

To a solution of N-(2-benzoyl-4-(trifluoromethyl)phenyl)-2-methoxyacetamide (0.1 g, 0.3 mmol, 1.00 equiv) in EtOH (3 mL) was added KOH (34 mg, 0.6 mmol, 1.5 equiv) at room temperature and the reaction mixture was heated to 80° C. for 1 h. Water (10 mL) was added to the reaction mixture and it was extracted with EtOAc (2×20 mL). The combined organic layers were washed with brine (10 mL) and dried over anhydrous $Na_2SO_4$. Purification by prep HPLC (mobile phase—0.10% aqueous formic acid, mobile phase B—MeCN, column—X-BRIDGE C18 (19×250) mm 5u, flow—18 ml/min, gradient method) to afford 3-methoxy-4-phenyl-6-(trifluoromethyl)quinolin-2(1H)-one as a white solid (5 mg, 6%); $^1$HNMR (500 MHz, DMSO-$d_6$) δ 12.473 (s, 1H), 7.77 (d, J=1.5 Hz, 1H), 7.58-7.50 (m, 4H), 7.380-7.36 (m, 2H), 7.2 (s, 1H), 3.73 (s, 3H). LC-MS (ESI, m/z): 320.30 $[M+H]^+$.

Example 18: Synthesis of 3-hydroxy-4-phenyl-6-(trifluoromethyl)quinolin-2(1H)-one (Compound 1.020)

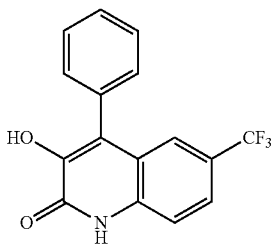 [SMILES: O=c1[nH]c2ccc(C(F)(F)F)cc2c(-c2ccccc2)c1O]

The title compound was prepared by the procedure described in Example 16, by replacing 2-methylbenzaldehyde with benzaldehyde. $^1$HNMR (500 MHz, DMSO-$d_6$) δ 12.80-12.41 (m, 1H), 9.89-9.45 (m, 1H), 7.66 (d, J=9.0 2.0 Hz, 1H), 7.56-7.45 (m, 4H), 7.37-7.35 (m, 2H), 7.27 (d, J=1.5 Hz, 1H). LC-MS (ESI, m/z): 306.23 $[M+H]^+$.

Example 19: Synthesis of 6-chloro-4-(2-chlorophenyl)-3-hydroxyquinolin-2(1H)-one (Compound 1.021)

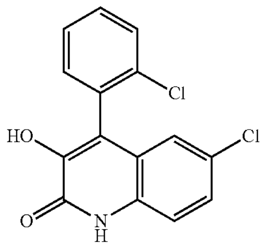

The title compound was prepared by the procedure described in Example 15, by replacing 2-methylbenzaldehyde with 2-chlorobenzaldehyde; $^1$HNMR (500 MHz, DMSO-$d_6$) δ 12.42-12.41 (m, 1H), 9.85-9.83 (m, 1H), 7.66-7.64 (m, 1H), 7.53-7.48 (m, 2H), 7.38-7.36 (m, 3H), 6.65 (d, J=1.5 Hz, 1H). LC-MS (ESI, m/z): 306.17 $[M+H]^+$.

Example 20: Synthesis of 3-Hydroxy-4-(1-methyl-1H-pyrazol-5-yl)-6-(trifluoromethyl)quinolin-2(1H)-one (Compound 1.022)

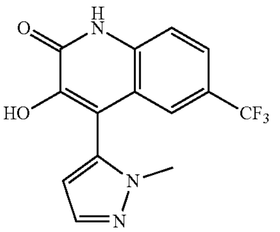 [SMILES: Cn1nccc1-c1c(O)c(=O)[nH]c2ccc(C(F)(F)F)cc12]

To a stirred solution of 1-methyl-1H-pyrazole-5-carbaldehyde (0.102 g, 0.93 mmol, 1.00 equiv) in EtOH (10 mL) was added 4-methylbenzenesulfonohydrazide (0.17 g, 0.93 mmol, 1.00 equiv) and stirred at RT for 1 h. 5-(Trifluoromethyl)indoline-2,3-dione (0.20 g, 0.93 mmol, 1.00 equiv) and potassium carbonate (0.26 g, 1.85 mmol, 2.00 equiv) were added and the reaction mixture was stirred at 80° C. for 16 h. The reaction mixture was diluted with water (10 mL) and extracted with EtOAc (2×30 mL). The combined organic layers were washed with brine (20 mL), dried over $Na_2SO_4$, filtered and concentrated. Purification by prep-HPLC (mobile phase A—0.10% aqueous formic acid; mobile phase B—MeCN; column—X-Bridge $C_{18}$ (19×250) mm, 5 mic; flow—18 mL/min; gradient method) afforded 3-hydroxy-4-(1-methyl-1H-pyrazol-5-yl)-6-(trifluoromethyl)quinolin-2(1H)-one (60 mg, 20.8%) as an off white solid. $^1$HNMR (500 MHz, DMSO-$d_6$) δ 12.65 (s, 1H), 10.47 (br s, 11H), 7.68 (d, J=8.5 Hz, 1H), 7.61 (d, J=2.0 Hz, 11H), 7.52 (d, J=8.5 Hz, 1H), 7.35 (s, 1H), 6.42 (d, J=1.5 Hz, 1H), 3.32 (s, 3H). LC-MS (ESI, m/z): 310 $[M+H]^+$.

Example 21: Synthesis of 3-Hydroxy-4-(2-methylpyridin-3-yl)-6-(trifluoromethyl)quinolin-2(1H)-one (Compound 1.023)

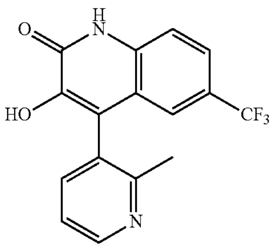 [SMILES: Cc1ncccc1-c1c(O)c(=O)[nH]c2ccc(C(F)(F)F)cc12]

The title compound was prepared by the procedure described in Example 20, by substituting 1-methyl-1H-pyrazole-5-carbaldehyde with 2-methylnicotinaldehyde. $^1$HNMR (400 MHz, DMSO-$d_6$) δ 12.64 (s, 1H), 9.98 (br s, 1H), 8.57 (d, J=3.6 Hz, 1H), 8.14 (s, 1H), 7.68 (d, J=8.4 Hz, 1H), 7.63 (d, J=7.6 Hz, 1H), 7.54 (d, J=8.4 Hz, 1H), 7.40-7.35 (m, 1H), 6.98 (s, 1H), 2.23 (s, 3H). LC-MS (ESI, m/z): 321.1 $[M+H]^+$.

Example 22: Synthesis of 3-Hydroxy-8-methoxy-4-(o-tolyl)-6-(trifluoromethyl)quinolin-2(1H)-one (Compound 1.024)

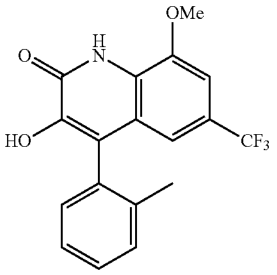 [SMILES: COc1cc(C(F)(F)F)cc2c(-c3ccccc3C)c(O)c(=O)[nH]c12]

Step 1: Preparation of 2-Methoxy-1-nitro-4-(trifluoromethyl)benzene

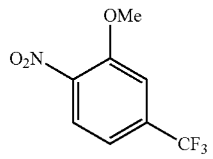

To a stirred solution of NaH (344 mg, 14.3 mmol, 1.50 equiv) in THF (20 mL) at 0° C. was added MeOH (0.40 mL, 11.5 mmol, 1.20 equiv) and the resulting mixture was stirred at 0° C. for 20 min. A solution of 2-fluoro-4-nitro-1-(trifluoromethyl)benzene (2.0 g, 9.56 mmol, 1.00 equiv) in THF (5 mL) was then added to the above mixture at 0° C. The reaction mixture was stirred at RT for 6 h. The reaction mixture was diluted with water (20 mL) and extracted with EtOAc (2×50 mL). The combined organic layers were washed with brine (30 mL), dried over $Na_2SO_4$, filtered and concentrated. Purification by silica gel chromatography afforded 2-methoxy-1-nitro-4-(trifluoromethyl)benzene (1.9 g, 89%) as a white solid.

Step-2: Preparation of 2-Methoxy-4-(trifluoromethyl)aniline

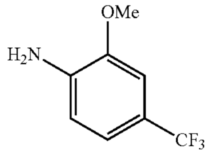

To a stirred solution of 2-methoxy-1-nitro-4-(trifluoromethyl)benzene (3.0 g, 13.6 mmol, 1.00 equiv) in MeOH (32 mL) was added 10% Pd/C (4.3 g, 4.07 mmol) at RT. The reaction mixture was stirred at RT under $H_2$ (1 atm, balloon) for 12 h. The reaction mixture was filtered through a pad of Celite by washing with MeOH and the filtrate was concentrated. Purification by silica gel chromatography afforded 2-methoxy-4-(trifluoromethyl)aniline (2.1 g, 80%) as a brown oil. LC-MS (ESI, m/z): 192.10 $[M+H]^+$.

Step-3: Preparation of 2-(Hydroxyimino)-N-(2-methoxy-4-(trifluoromethyl)phenyl)acetamide

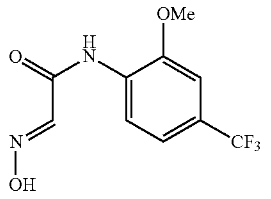 [SMILES: COc1cc(C(F)(F)F)ccc1NC(=O)/C=N/O]

To a stirred solution of chloral hydrate (1.91 g, 11.6 mmol, 1.30 equiv) and 2-methoxy-4-(trifluoromethyl) aniline (1.7 g, 8.89 mmol, 1.00 equiv) in water (60 mL) was added a solution of $Na_2SO_4$ (18 g, 133.4 mmol, 15.0 equiv) in water (70 mL) at RT. The reaction mixture was stirred at RT for 25 min and a solution of hydroxylamine hydrochloride (4.3 g, 62.2 mmol, 7.00 equiv) in water (20 mL) was added. The reaction mixture was stirred at 100° C. for 2 h. The reaction mixture was cooled to RT and extracted with EtOAc (2×100 mL). The combined organic layers were washed with brine (1×50 mL), dried over $Na_2SO_4$, filtered and concentrated. Purification by silica gel chromatography afforded 2-(Hydroxyimino)-N-(2-methoxy-4-(trifluoromethyl)phenyl)acetamide (1.3 g, 55%) as a white solid. LC-MS (ESI, m/z): 263.2 $[M+H]^+$.

Step-4: Preparation of 7-Methoxy-5-(trifluoromethyl)indoline-2,3-dione

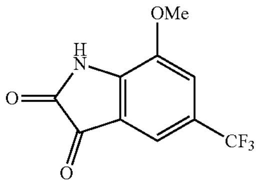 [SMILES: COc1cc(C(F)(F)F)cc2c1NC(=O)C2=O]

2-(Hydroxyimino)-N-(2-methoxy-4-(trifluoromethyl) phenyl)acetamide (130 mg, 0.496 mmol) was added to concentrated $H_2SO_4$ (0.34 mL) at 50° C. and the mixture was stirred at the same temperature for 10 min followed by 15 min at 80° C. The reaction mixture was diluted with ice-cold water (5 mL) and extracted with EtOAc (2×20 mL). The combined organic layers were washed with brine (20 mL), dried over $Na_2SO_4$, filtered and concentrated. Purification by silica gel chromatography afforded 7-methoxy-5-(trifluoromethyl)indoline-2,3-dione (40 mg, 7%) as an yellow solid. LC-MS (ESI, m/z): 244.09 $[M-H]^-$.

Step-5: Preparation of 3-Hydroxy-8-methoxy-4-(o-tolyl)-6-(trifluoromethyl)quinolin-2(1H)-one

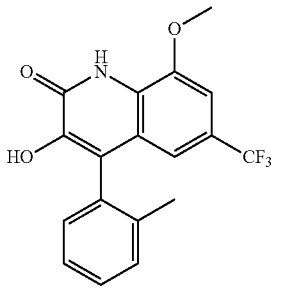 [SMILES: COc1cc(C(F)(F)F)cc2c(-c3ccccc3C)c(O)c(=O)[nH]c12]

The title compound was prepared by the procedure described in Example 20, by substituting 1-methyl-1H-pyrazole-5-carbaldehyde with 2-methylbenzaldehyde and 5-(trifluoromethyl)indoline-2,3-dione with 7-methoxy-5-(trifluoromethyl)indoline-2,3-dione. $^1$HNMR (400 MHz, DMSO-$d_6$) δ 11.82 (s, 1H), 9.66 (s, 1H), 7.39-7.29 (m, 3H), 7.22-7.20 (m, 1H), 7.13 (d, J=8 Hz, 1H), 6.62 (s, 1H), 3.98 (s, 3H), 1.99 (s, 3H). LC-MS (ESI, m/z): 350.1 $[M+H]^+$.

Example 23: Synthesis of 6-Bromo-3-hydroxy-4-(2-methylpyridin-3-yl)quinolin-2(1H)-one (Compound 1.025)

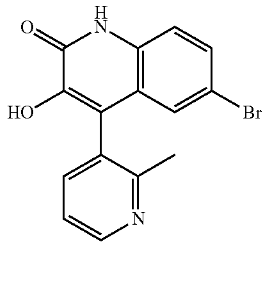

The title compound was prepared by the procedure described in Example 20, by substituting 1-methyl-1H-pyrazole-5-carbaldehyde with 2-methylnicotinaldehyde and 5-(trifluoromethyl)indoline-2,3-dione with 5-bromoindoline-2,3-dione. $^1$HNMR (400 MHz, DMSO-$d_6$) δ 12.38 (br s, 1H), 9.90 (br s, 1H), 8.54 (dd, J=4.8, 1.6 Hz, 1H), 7.58 (dd, J=7.6 Hz, 1.6 Hz, 1H), 7.47 (d, J=8.0 Hz, 1H), 7.36 (dd, J=7.6, 4.8 Hz, 1H), 7.30 (d, J=8.0 Hz, 1H), 6.79 (d, J=2 Hz, 1H), 2.23 (s, 3H). LC-MS (ESI, m/z): 331.0 $[M+H]^+$.

Example 24: Synthesis of 6-Chloro-3-hydroxy-4-(2-methylpyridin-3-yl)quinolin-2(1H)-one (Compound 1.026)

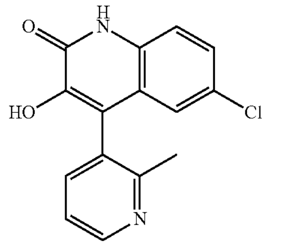 [SMILES: Cc1ncccc1-c1c(O)c(=O)[nH]c2ccc(Br)cc12]

The title compound was prepared by the procedure described in Example 20, by substituting 1-methyl-1H-pyrazole-5-carbaldehyde with 2-methylnicotinaldehyde and 5-(trifluoromethyl)indoline-2,3-dione with 5-chloroindoline-2,3-dione. $^1$HNMR (400 MHz, DMSO-$d_6$) δ 12.42 (s, 1H), 9.84 (br s, 1H), 8.55 (dd, J=4.8, 1.6 Hz, 1H), 7.60 (dd, J=7.6, 1.6 Hz, 1H), 7.42-7.35 (m, 3H), 6.67 (s, 1H), 2.23 (s, 3H). LC-MS (ESI, m/z): 287.1 $[M+H]^+$.

Example 25: Synthesis of 6-Bromo-4-(1-ethyl-1H-pyrazol-5-yl)-3-hydroxyquinolin-2(1H)-one (Compound 1.027)

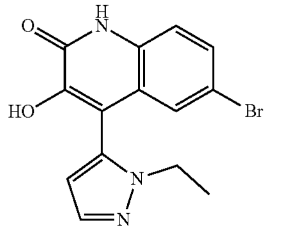 [SMILES: CCn1nccc1-c1c(O)c(=O)[nH]c2ccc(Br)cc12]

The title compound was prepared by the procedure described in Example 20, by substituting 1-methyl-1H-pyrazole-5-carbaldehyde with 1-ethyl-1H-pyrazole-5-carbaldehyde and 5-(trifluoromethyl)indoline-2,3-dione with 5-bromoindoline-2,3-dione. $^1$HNMR (400 MHz, DMSO-$d_6$) δ 12.32 (br s, 1H), 7.61 (s, 1H), 7.43 (dd, J=8.4 Hz, 1H), 7.25 (d, J=8.4 Hz, 1H), 7.03 (s, 1H), 6.30 (s, 1H), 3.87 (q, J=7.2 Hz, 2H), 1.19 (t, J=7.2 Hz, 3H). LC-MS (ESI, m/z): 334.1 $[M+H]^+$.

Example 26: Synthesis of 6-Bromo-3-methoxy-4-(2-methylpyridin-3-yl)quinolin-2(1H)-one (Compound 1.028)

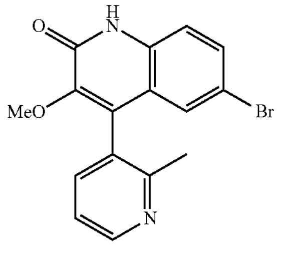 [SMILES: COc1c(-c2cccnc2C)c2cc(Br)ccc2[nH]c1=O]

Step 1: Preparation of 5-Bromo-1-((2-(trimethylsilyl)ethoxy)methyl)indoline-2,3-dione

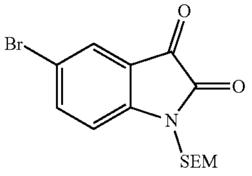 [SMILES: C[Si](C)(C)CCOCN1C(=O)C(=O)c2cc(Br)ccc21]

To a stirred solution of 5-bromoindoline-2,3-dione (1.00 g, 4.42 mmol, 1.00 equiv) in THF (20 mL) were added NaH (212 mg, 8.85 mmol, 2.00 equiv, 60% in mineral oil) and 2-(trimethylsilyl)ethoxymethyl chloride (0.94 mL, 5.30 mmol, 1.20 equiv) at 0° C. and the resulting mixture was stirred at RT for 12 h. Ice-cold water (40 mL) was added at 0° C. and THF was removed under reduced pressure. The obtained residue was diluted with water (20 ml) and extracted with EtOAc (2×50 mL). The combined organic layers were washed with brine (50 mL), dried over $Na_2SO_4$, filtered and concentrated. Purification by silica gel chromatography afforded 5-bromo-1-((2-(trimethylsilyl)ethoxy)methyl)indoline-2,3-dione (1.1 g, 69%) as an orange solid. $^1$HNMR (500 MHz, DMSO-$d_6$) δ 7.90 (d, J=8.5 Hz, 1H), 7.79 (s, 1H), 7.21 (d, J=8.5 Hz, 1H), 5.13 (s, 2H), 3.60 (t, J=8 Hz, 2H), 0.90 (t, J=8 Hz, 2H), 0.0 (s, 9H).

Step-2: Preparation of 6-Bromo-3-hydroxy-4-(2-methylpyridin-3-yl)-1-((2-(trimethylsilyl)ethoxy)methyl)quinolin-2(1H)-one

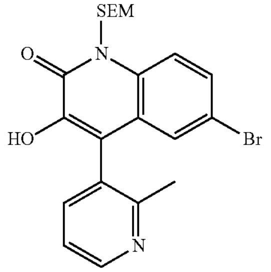 [SMILES: Cc1ncccc1-c1c(O)c(=O)n(COCC[Si](C)(C)C)c2ccc(Br)cc12]

To a stirred solution of 2-methylnicotinaldehyde (136 mg, 1.12 mmol, 1.00 equiv) in EtOH (10 mL) was added 4-methylbenzenesulfonohydrazide (208 mg, 1.12 mmol, 1.00 equiv) and the resulting mixture was stirred at RT for 1 h. 5-Bromo-1-((2-(trimethylsilyl)ethoxy)methyl)indoline-2,3-dione (400 mg, 1.12 mmol, 1.00 equiv) and $K_2CO_3$ (310 mg, 2.24 mmol, 2.00 equiv) were added successively and the mixture was heated to 80° C. for 15 h. Ethanol was removed under reduced pressure and the obtained residue was diluted with water (20 ml) and extracted with EtOAc (2×50 mL). The combined organic layers were washed with brine (20 mL), dried over $Na_2SO_4$, filtered and concentrated. Purification by silica gel chromatography afforded 6-bromo-3-hydroxy-4-(2-methylpyridin-3-yl)-1-((2 (trimethylsilyl)ethoxy)methyl)quinolin-2(1H)-one (280 mg, 54%) as a yellow solid. LC-MS (ESI, m/z): 461 $[M+H]^+$.

Step 3: Preparation of 6-Bromo-3-methoxy-4-(2-methylpyridin-3-yl)-1-((2-(trimethylsilyl)ethoxy)methyl)quinolin-2(1H)-one

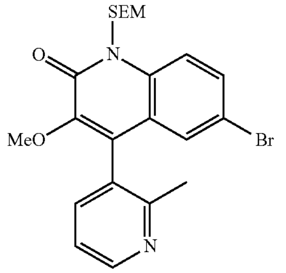 [SMILES: COc1c(-c2cccnc2C)c2cc(Br)ccc2n(COCC[Si](C)(C)C)c1=O]

To a stirred solution of 6-bromo-3-hydroxy-4-(2-methylpyridin-3-yl)-1-((2-(trimethylsilyl)ethoxy)methyl)quinolin-2(1H)-one (250 mg, 0.54 mmol, 1.00 equiv) in THF (10 mL) were added potassium carbonate (74.5 mg, 0.54 mmol, 1.00 equiv) and dimethyl sulphate (81.9 mg, 0.65 mmol, 1.20 equiv) at RT and the reaction mixture was stirred for 30 min. The reaction mixture was diluted with ice-cold water (10 mL) and extracted with EtOAc (2×30 mL). The combined organic layers were washed with brine (10 mL), dried over $Na_2SO_4$, filtered and concentrated. Purification by silica gel chromatography afforded 6-bromo-3-methoxy-4-(2-methylpyridin-3-yl)-1-((2-(trimethylsilyl)ethoxy)methyl)quinolin-2(1H)-one (158 mg, 61%) as a yellow solid. LC-MS (ESI, m/z): 475 $[M+H]^+$.

Step 4: Preparation of 6-Bromo-3-methoxy-4-(2-methylpyridin-3-yl)quinolin-2(1H)-one

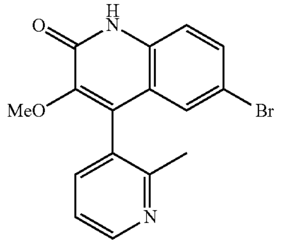 [SMILES: COc1c(-c2cccnc2C)c2cc(Br)ccc2[nH]c1=O]

To a stirred solution of 6-bromo-3-methoxy-4-(2-methylpyridin-3-yl)-1-((2-(trimethylsilyl)ethoxy)methyl)quinolin-2(1H)-one (140 mg, 0.29 mmol, 1.00 equiv) in DCM (5 mL) was added TFA (1.4 mL, 1.5 mmol, 5.00 equiv) at 0° C. and the resulting mixture was stirred at RT for 12 h. The reaction mixture was diluted with water (20 mL) and extracted with EtOAc (2×20 mL). The combined organic layers were washed with saturated aqueous $NaHCO_3$ (20 ml), brine (20 mL), dried over $Na_2SO_4$, filtered and concentrated. Purification by prep-HPLC (mobile phase A—0.10% aqueous formic acid; mobile phase B—MeCN; column—X-BRIDGE C18 (19×250) mm, 5 mic; flow—18 mL/min; gradient method) afforded 6-bromo-3-methoxy-4-(2-methylpyridin-3-yl)quinolin-2(1H)-one (24 mg, 24%) as an off-white solid. $^1$HNMR (400 MHz, DMSO-$d_6$) δ 12.3 (br s, 1H), 8.59 (d, J=4.8, 1.6 Hz, 1H), 7.65-7.58 (m, 2H), 7.42-7.32 (m, 2H), 7.79 (s, 1H), 3.73 (s, 3H), 2.22 (s, 3H). LC-MS (ESI, m/z): 345.2 $[M+H]^+$.

Biological Examples

The ability of the compound of present disclosure to inhibit MAT2A enzyme was determined using a Phosphate Sensor Fluorescence Assay described below.

Biologic Example A. Phosphate Sensor Fluorescence Assay

MAT2A enzyme is incubated with a test compound in DMSO or DMSO and its substrates (L-methionine and ATP) in a microtiter plate. The enzymatic reaction is stopped by the addition of Working Phosphate Sensor Mixture. The plate is analyzed for fluorescence at 450 nm. The high control (DMSO with enzyme and its substrates) gives high fluorescence which represents no inhibition of enzymatic activity while the low control (DMSO with MAT2A substrates and no enzyme) gives low fluorescence which represents full inhibition of enzymatic activity.

Materials

Human MAT2A: Cepter, amino acids 1-395
Tris, pH 7.5: Invitrogen cat #15567-027
KCl: Ambion cat #AM9640G
MgCl2: Ambion cat #AM9530G
Brij-35: Sigma cat B4184-10ML
DTT: Goldbio cat #DTT100
BGG: Sigma cat #G5009-25G
PNP: Novus Biologicals cat #NBP1-50872
7-MEG: Cayman Chemical cat #15988
L-Methionine: Alfa Aesar cat #J61904
ATP: Alfa Aesar cat #J60336
Phosphate Sensor: Thermo Fisher cat #PV4407
EDTA: Life Tech cat #15575-038
Assay plate: 384-well black polypropylene plate: Thomas Scientific cat #1149Q35

Final Assay Conditions:

Assay Buffer: 50 mM Tris, pH 7.5/50 mM KCl/10 mM $MgCl_2$/0.01% Brij-35/1 mM DTT/0.1% BGG/40 nM PNP/6 uM 7-MEG MAT2A: 10 nM for Cepter clone ID 329, lot 00023-123 before the addition of Working Phosphate Sensor Mixture 5 nM for Cepter clone ID 334, lot 00023-148 before the addition of Working Phosphate Sensor Mixture L-methionine: 500 uM before the addition of Working Phosphate Sensor Mixture ATP: 500 uM before the addition of Working Phosphate Sensor Mixture Procedure:

For the assay, a mixture of 1 mM L-methionine/1 mM ATP (2× final pre-stopped concentration) in assay buffer; MAT2A (2× final pre-stopped concentration) in Assay Buffer and Working Phosphate Sensor Mixture (1.5 uM Phosphate Sensor/30 mM EDTA in Assay Buffer, which is 3× final concentrations) were prepared. Test compounds or DMSO were added to the appropriate well suing D300e digital dispenser. 5 μl/well of Assay Buffer was added to the wells corresponding to the negative control and 5 μl/well of MAT2A was added to all the wells except for those corresponding to the negative control. After incubating the plate at room temperature for 15 minutes, 5 μl/well of the 1 mM L-methionine/1 mM ATP mixture was added to all wells. The plate was centrifuged at 1000 rpm for 1 minute and then incubated at room temperature for 1 hour. 5 μl of the Working Phosphate Sensor Mixture was added to all wells and the plate was centrifuged at 1000 rpm for 1 minute. The plate was read for fluorescence at 450 nm after exciting at 430 nm.

Data Analysis:

Percent inhibition was calculated in Chemical and Biological Information System (CBIS), (ChemInnovation Software Inc.). Curves were fitted by CBIS as % inhibition vs. log [compound concentration] using a 4-parameter inhibition model.

$$Fit=(A+((B-A)/(1+((C/x)^D))))$$

$$Res=(y-fit)$$

Biologic Example B. Phosphate Sensor Fluorescence Assay

MAT2A enzyme is incubated with a test compound in DMSO or DMSO and its substrates (L-methionine and ATP) in a microtiter plate. The enzymatic reaction is stopped by the addition of Working Phosphate Sensor Mixture. The plate is analyzed for fluorescence at 450 nm. The high control (DMSO with enzyme and its substrates) gives high fluorescence which represents no inhibition of enzymatic activity while the low control (DMSO with MAT2A substrates and no enzyme) gives low fluorescence which represents full inhibition of enzymatic activity.

Materials

- Human MAT2A: Cepter, amino acids 1-395 Clone ID 334, lot 00023-148
- Tris, pH 7.5: Invitrogen cat #15567-027
- KCl: Ambion cat #AM9640G
- $MgCl_2$: Ambion cat #AM9530G
- Brij-35: Sigma cat B4184-10ML
- DTT: Goldbio cat #DTT100
- BGG: Sigma cat #G5009-25G
- PNP: Novus Biologicals cat #NBP1-50872
- 7-MEG: Cayman Chemical cat #15988
- L-Methionine: JTBaker P/N 2085-05
- ATP: Promega P/N V915B
- Phosphate Sensor: Invitrogen cat #PV4407
- EDTA: Life Tech cat #15575-038
- Assay plate: 384-well black polypropylene plate: Corning P/N 3573

Final Assay Conditions:

- Assay Buffer: 50 mM Tris, pH 7.5/50 mM KCl/10 mM MgCl2/0.01% Brij-35/1 mM DTT/0.01% BGG/40 nM PNP/6 uM 7-MEG
- MAT2A: 5.8 nM MAT2A (1-395), Cepter, clone ID 334, lot 00023-148 before the addition of Working Phosphate Sensor Mixture
- L-methionine: 500 uM before the addition of Working Phosphate Sensor Mixture
- ATP: 500 uM before the addition of Working Phosphate Sensor Mixture Procedure:

For the assay, a mixture of 1 mM L-methionine/1 mM ATP (2× final pre-stopped concentration) in assay buffer; MAT2A (2× final pre-stopped concentration) in Assay Buffer and Working Phosphate Sensor Mixture (1.5 uM Phosphate Sensor/30 mM EDTA in Assay Buffer, which is 3× final concentrations) were prepared. Test compounds or DMSO were added to the appropriate well using a Beckman Coulter Echo 550 acoustic liquid handler. 10 L/well of Assay Buffer was added to the wells corresponding to the negative control and 10 L/well of MAT2A was added to all the wells except for those corresponding to the negative control. After incubating the plate at room temperature for 15 minutes, 10 μL/well of the 1 mM L-methionine/1 mM ATP mixture was added to all wells. The plate was centrifuged at 1000 rpm for 1 minute and then incubated at room temperature for 1 hour. 10 μL of the Working Phosphate Sensor Mixture was added to all wells and the plate was centrifuged at 1000 rpm for 1 minute. The plate was read for fluorescence at 450 nm after exciting at 430 nm on a Tecan Spark microplate reader.

Data Analysis:

Percent inhibition was calculated in Chemical and Biological Information System (CBIS), (ChemInnovation Software Inc.). Curves were fitted by CBIS as % inhibition vs. log [compound concentration] using a 4-parameter inhibition model.

$$Fit=(A+((B-A)/(1+((C/x)^D))))$$

$$Res=(y-fit)$$

The $IC_{50}$ of a representative number of compounds in Table 1 above are disclosed in Table 2 below. Compounds 1.001-1.021 were tested using the procedure described in Biological Example A, described above. Compounds 1.022-1.026 were tested using the procedure described in Biological Example B, described above.

(+) $IC_{50}$=10 μM−1 μM; 1 μM>(++) $IC_{50}$≥500 nM; 500 nM>(+++) $IC_{50}$≥200 nM; 200 nM>(++++) $IC_{50}$≥10 nM; 10 nM>(+++++)

TABLE 2

| Cpd. No. (Table 1) | $IC_{50}$ |
|---|---|
| 1.001 | >10 μM |
| 1.002 | ++ |
| 1.003 | + |
| 1.004 | +++ |
| 1.005 | + |
| 1.006 | + |
| 1.007 | >10 |
| 1.008 | + |
| 1.009 | ++++ |
| 1.010 | ++++ |
| 1.011 | ++++ |
| 1.012 | +++ |
| 1.013 | + |
| 1.014 | + |
| 1.015 | ++++ |
| 1.016 | + |
| 1.017 | ++++ |
| 1.018 | ++++ |
| 1.019 | ++++ |
| 1.020 | ++++ |
| 1.021 | ++++ |
| 1.022 | ++++ |
| 1.023 | +++++ |
| 1.024 | ++++ |
| 1.025 | ++++ |
| 1.026 | ++++ |

What is claimed:

1. A compound having the Formula (Ig)

(Ig)

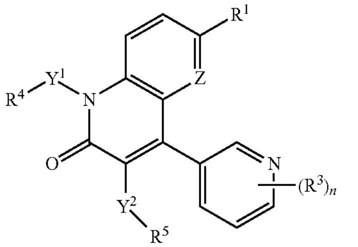

or a pharmaceutically acceptable salt thereof, wherein

Z is CH;

$R^1$ is selected from the group consisting of $C_{1-6}$ alkyl, $C_{1-6}$ haloalkyl, $C_{1-6}$ alkoxy, $C_{1-6}$ haloalkoxy, cyano, halo, and $C_{3-8}$ cycloalkyl, wherein the cycloalkyl group is substituted with from 0 to 2 groups independently selected from the group consisting of $C_{1-4}$ alkyl and halo;

each $R^3$ is independently selected from the group consisting of halo, $C_{1-4}$ alkyl, $C_{1-4}$ haloalkyl, —$OR^z$, and —$X^4$—$OR^z$, wherein each $R^z$ is selected from the group consisting of H, $C_{1-4}$ alkyl, and $C_{1-4}$ haloalkyl, and each $X^4$ is $C_{1-3}$ alkylene;

the subscript n is 0, 1 or 2;

$Y^1$ is a bond;

$R^4$is H;

$Y^2$ is selected from the group consisting of a bond and $C_{1-4}$ alkylene;

$R^5$ is selected from the group consisting of halo, cyano, $C_{1-6}$ alkyl, $C_{1-6}$ haloalkyl, —$OR^c$, —O—$X^1$—$R^c$, —$SR^c$, —S—$X^1$—$R^c$, —$S(O)_2R^c$, —$S(O)_2$—$X^1$—$R^c$, —$S(O)_2$—$NR^h$—$R^c$, —$S(O)_2$—$NR^h$—$X^1$—$R^c$, —$NR^h$—$S(O)_2$—$R^c$, —$NR^h$—$S(O)_2$—$X^1$—$R^c$, and a 3- to 6-membered heterocycloalkyl having 1 to 3 heteroatom ring vertices independently selected from the group consisting of N, O, and S;

$X^1$ is selected from the group consisting of a bond and $C_{1-4}$ alkylene;

$R^c$ is selected from the group consisting of H, $C_{1-6}$ alkyl, $C_{1-6}$ haloalkyl, $C_{3-8}$ cycloalkyl, $C_{6-10}$ aryl, a 3- to 6-membered heterocycloalkyl having 1 to 3 heteroatom ring vertices independently selected from N, O, and S, and a 5- to 10-membered heteroaryl having 1 to 4 heteroatom ring vertices independently selected from the group consisting of N, O, and S, wherein the $C_{3-8}$ cycloalkyl, the $C_{6-10}$ aryl, the 3- to 6-membered heterocycloalkyl, and the 5- to 10-membered heteroaryl are substituted with 0 to 2 moieties independently selected from the group consisting of $C_{1-4}$ alkyl, —$OR^y$, —$X^3$—$OR^y$, —$C(O)R^y$, —$X^3$—$C(O)R^y$, —$C(O)OR^y$, and —$X^3$—$C(O)OR^y$, wherein each $R^y$ is selected from the group consisting of H, $C_{1-6}$ alkyl, and $C_{1-6}$ haloalkyl, and each $X^3$ is $C_{1-3}$ alkylene; and $R^h$ is selected from the group consisting of H, $C_{1-6}$ alkyl and $C_{1-6}$ haloalkyl.

2. The compound of claim 1 or a pharmaceutically acceptable salt thereof, wherein $R^1$ is selected from the group consisting of $C_{1-6}$ alkyl, $C_{1-6}$ haloalkyl, halo, and $C_{3-8}$ cycloalkyl, wherein the cycloalkyl group is substituted with from 0 to 2 groups independently selected from the group consisting of $C_{1-4}$ alkyl and halo.

3. The compound of claim 1 or a pharmaceutically acceptable salt thereof, wherein each $R^3$ is independently selected from the group consisting of halo, $C_{1-4}$ alkyl, and $C_{1-4}$ haloalkyl.

4. The compound of claim 1 or a pharmaceutically acceptable salt thereof, wherein each $R^3$ is independently selected from the group consisting of —$OR^z$ and —$X^4$—$OR^z$, wherein each $R^z$ is H or $C_{1-4}$ alkyl, and each $X^4$ is $C_{1-3}$ alkylene.

5. The compound of claim 1 or a pharmaceutically acceptable salt thereof, wherein the subscript n is 1 or 0.

6. The compound of claim 1 or a pharmaceutically acceptable salt thereof, wherein $Y^2$ is a bond or methylene.

7. The compound of claim 1 or a pharmaceutically acceptable salt thereof, wherein $R^5$ is selected from the group consisting of halo, cyano $C_{1-6}$ alkyl, and $C_{1-6}$ haloalkyl.

8. The compound of claim 1 or a pharmaceutically acceptable salt thereof, wherein $R^5$ is selected from the group consisting of —$OR^c$ and —O—$X^1$—$R^c$.

9. The compound of claim 1 or a pharmaceutically acceptable salt thereof, wherein the compound is selected from the group consisting of:

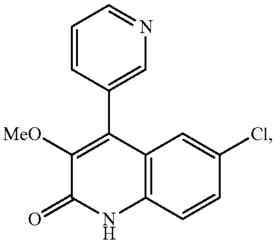,

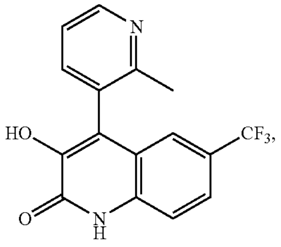,

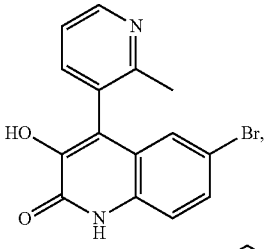,

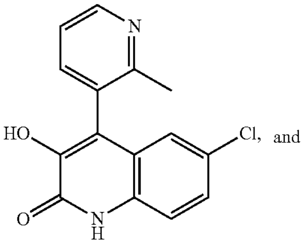, and

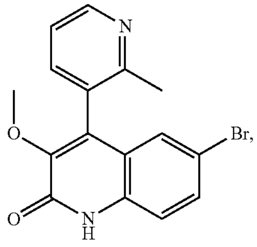, or a pharmaceutically acceptable salt thereof.

10. A pharmaceutical composition comprising a compound of claim 1 or a pharmaceutically acceptable salt thereof and at least one pharmaceutically acceptable excipient.

* * * * *